(12) United States Patent
Pappin et al.

(10) Patent No.: US 7,195,751 B2
(45) Date of Patent: *Mar. 27, 2007

(54) COMPOSITIONS AND KITS PERTAINING TO ANALYTE DETERMINATION

(75) Inventors: Darryl J. C. Pappin, Boxborough, MA (US); Michael Bartlet-Jones, Worcester Park (GB)

(73) Assignee: Applera Corporation, Framingham, MA (US)

( * ) Notice: Subject to any disclaimer, the term of this patent is extended or adjusted under 35 U.S.C. 154(b) by 43 days.

This patent is subject to a terminal disclaimer.

(21) Appl. No.: 10/765,267

(22) Filed: Jan. 27, 2004

(65) Prior Publication Data

US 2004/0220412 A1    Nov. 4, 2004

Related U.S. Application Data

(60) Provisional application No. 60/443,612, filed on Jan. 30, 2003.

(51) Int. Cl.
*C07D 413/12* (2006.01)
*C07D 403/12* (2006.01)
*C07D 401/12* (2006.01)
*C07D 265/30* (2006.01)
*C07D 241/04* (2006.01)
*C07D 211/34* (2006.01)
*A61K 51/04* (2006.01)
*C07D 403/02* (2006.01)
*C12Q 1/37* (2006.01)

(52) U.S. Cl. ............... 424/1.81; 424/1.85; 424/1.89; 435/6; 435/23; 544/141; 544/172; 544/372; 544/399; 546/208; 546/238

(58) Field of Classification Search ............... 544/64, 544/112, 141, 172, 372, 399; 546/2, 208, 546/238; 424/1.37, 1.81; 435/6, 23
See application file for complete search history.

(56) References Cited

U.S. PATENT DOCUMENTS

| | | | |
|---|---|---|---|
| 3,860,581 A | 1/1975 | Nudelman et al. ... 260/239.3 D |
| 5,087,815 A | 2/1992 | Schultz et al. ............... 250/309 |
| 5,780,232 A | 7/1998 | Arlinghaus et al. ............ 435/6 |
| 6,027,890 A | 2/2000 | Ness et al. ...................... 435/6 |
| 6,156,527 A | 12/2000 | Schmidt et al. ............... 435/24 |
| 6,312,893 B1 | 11/2001 | Van Ness et al. ............... 435/6 |
| 6,319,476 B1 | 11/2001 | Victor, Jr. et al. .......... 422/103 |
| 6,329,180 B1 | 12/2001 | Garvin ....................... 435/91.2 |
| 6,383,754 B1 | 5/2002 | Kaufman et al. ............... 435/6 |
| 6,395,474 B1 | 5/2002 | Buchardt et al. ............... 435/6 |
| 6,403,309 B1 | 6/2002 | Iris et al. ........................ 435/6 |
| 6,428,956 B1 | 8/2002 | Crooke et al. .................. 435/6 |
| 6,472,156 B1 | 10/2002 | Wittwer et al. ................. 435/6 |
| 6,475,807 B1 | 11/2002 | Geysen et al. ............... 436/518 |
| 6,613,508 B1 | 9/2003 | Ness et al. ...................... 435/6 |
| 6,629,040 B1 | 9/2003 | Goodlett et al. ............... 702/23 |
| 6,750,061 B2 | 6/2004 | Chait et al. ................... 436/89 |
| 6,824,981 B2 | 11/2004 | Chait et al. ..................... 435/6 |
| 2002/0119456 A1 | 8/2002 | Ness et al. ...................... 435/6 |
| 2002/0192720 A1 | 12/2002 | Parker et al. |
| 2003/0077595 A1 | 4/2003 | Van Ness et al. ............... 435/6 |
| 2004/0033625 A1 | 2/2004 | Aebersold ................... 436/518 |
| 2004/0219685 A1* | 11/2004 | Pappin et al. ............... 436/173 |
| 2004/0219686 A1* | 11/2004 | Pappin et al. ............... 436/173 |
| 2005/0049406 A1 | 3/2005 | Lerchen et al. |
| 2005/0147982 A1* | 7/2005 | Pappin et al. ................... 435/6 |
| 2005/0147985 A1* | 7/2005 | Pappin et al. ................... 435/6 |
| 2005/0148087 A1* | 7/2005 | Pappin et al. ................. 436/86 |
| 2005/0148771 A1* | 7/2005 | Dey et al. ................... 544/182 |
| 2005/0148773 A1* | 7/2005 | Pappin et al. ............... 544/358 |
| 2005/0148774 A1* | 7/2005 | Dey et al. ................... 544/399 |
| 2006/0105416 A1* | 5/2006 | Pappin et al. ................. 435/23 |
| 2006/0172319 A1* | 8/2006 | Yan et al. ....................... 435/6 |

FOREIGN PATENT DOCUMENTS

| | | |
|---|---|---|
| EP | 209763 A1 * | 1/1987 |
| EP | 0261804 | 8/1987 |
| EP | 1027454 | 1/1998 |
| EP | 0990047 B1 | 2/1999 |
| JP | 01125357 A2 * | 5/1989 |
| WO | WO94/15944 | 7/1994 |
| WO | WO98/15648 | 12/1996 |
| WO | WO97/11958 | 4/1997 |
| WO | WO98/15652 | 4/1998 |
| WO | WO98/26095 | 6/1998 |
| WO | WO98/31830 | 6/1998 |

(Continued)

OTHER PUBLICATIONS

Berry et al., Journal of Lipid Research (2005), 46(5), 1038-1046.*

(Continued)

*Primary Examiner*—Joseph K. McKane
*Assistant Examiner*—Nyeemah Grazier
(74) *Attorney, Agent, or Firm*—Brian D. Gildea

(57) ABSTRACT

This invention pertains to methods, mixtures, kits and/or compositions for the determination of analytes by mass analysis using unique labeling reagents or sets of unique labeling reagents. The labeling reagents can be isomeric or isobaric and can be used to produce mixtures suitable for multiplex analysis of the labeled analytes.

49 Claims, 13 Drawing Sheets

FOREIGN PATENT DOCUMENTS

| WO | WO98/32876 | 7/1998 |
|---|---|---|
| WO | WO99/02728 | 1/1999 |
| WO | WO99/13103 | 3/1999 |
| WO | WO99/14362 | 3/1999 |
| WO | WO99/05319 | 5/1999 |
| WO | WO00/11208 | 3/2000 |
| WO | WO00/20112 | 4/2000 |
| WO | WO01/68664 | 9/2001 |
| WO | WO01/86296 | 11/2001 |
| WO | WO02/14867 | 2/2002 |
| WO | WO03/001206 | 1/2003 |
| WO | WO03/025576 | 3/2003 |
| WO | WO2003/056343 A2 | 7/2003 |
| WO | WO03/077851 | 9/2003 |
| WO | WO03/078584 A2 | 9/2003 |
| WO | WO03/102220 | 12/2003 |
| WO | WO04/086050 A2 | 10/2004 |
| WO | WO 2004086050 A2 * | 10/2004 |

OTHER PUBLICATIONS

Aebersold, R. et al. "Mass Spectrometry in Proteomics". Chem Rev. 101, 269-295 (2001).

Al-Shahrour, F. et al. "FatiGO: A Web Tool For Finding Significant Associations of Gene Ontology Terms With Groups of Genes (fatigo.bioinfo.cnio.es)". Bioinformatics, 20, 578-580 (2004).

Alving, K. et al. "Characterization of O-Glycosylation Sites in MUC2 Glycopeptides by NanoElectrospray QTOF Mass Spectrometry". Journal of Mass Spectrometry, 34, 395-407 (1999).

Anderegg, R. et al. "Mass Spectrometric Characterization of a Protein-Ligand Interaction". J. Am. Chem. Soc., 117, 1374-1377 (1995).

Banks, R.E. et al. "Evidence for the existence of a novel pregnancy-associated soluble variant of the vascular endothelial growth factor receptor, Flt-1". Molecular Human Reproduction, 4, 377-386 (1998).

Bates, G. et al, Selective and Direct Activation of O-Esters. Conversion of Phenyl and 2,2,2-Trifluoroethyl Esters Into Acyl Imidazolides. Tetrahedron Letters, 49, 4423-4426 (1976).

Beck-Sickinger, A. et al. "Epitope mapping: synthetic approaches to the understanding of molecular recognition in the immune system". Pharmaceutical ACTA Helvetiac, 68, 3-20 (1993).

Benard, P. et al. "Homogeneous Multiplex Genotyping of Hemochromatosis Mutations with Fluorescent Hybridization Probes" American Journal of Pathology, 4, 1055-1061 (1998).

Biemann, K. et al. "Primary Structure of Peptides and Proteins". Biological Mass Spectrometry, 275-297 (1994).

Biswas, A. et al, "Rearrangement of N-(p-Toluenesulfonyloxy)-2-Pyrrolidinone". Heterocycles, 11, 2849-2851 (1987).

Chase, B.H. et al, "The Synthesis of C-Labelled Diethylcarbamazine, 1-Diethylcarbamyl-4-methylpiperazine ("Hetrazan")". The Journal of The Chemical Society, 3874-3877 (1953).

Chu, Y. et al. "Affinity Capillary Electrophoresis-Mass Spectrometry for Screening Combinatorial Libraries". J. Am. Chem. Soc. 118, 7827-7835 (1996).

Chu, Y. et al. "Free Solution Identification of Candidate Peptides from Combinatorial Libraries by Affinity Capillary Electrophoresis/Mass Spectrometry". J. Am. Chem. Soc. 117, 5419-5420 (1995).

Chu, Y. et al. "Using Affinity Capillary Electrophoresis To Identify the Peptide in a Peptide Library that Binds Most Tightly to Vancomycin". J. Org. Chem. 58, 648-652 (1993).

Cotterill, L. et al. "Qa-1 interaction and T cell recognition of the Qa-1 determinant modifier peptide". Eur. J. Immunol,- 27, 2123-2132 (1997).

Dunayevskiy, Y. et al, "Application of capillary electrophoresis-electrospray ionization mass spectrometry in the determination of molecular diversity". Proc. Natl. Acad. Sci. USA, 93, 6152-6157 (1996).

Ecker, D. et al. "Combinatorial Drug Discovery: Which Methods Will Produce the Greatest Value?" Biotechnology, 13, 351-360 (1995).

Eng, J. et at. "An Approach to Correlate Tandem Mass Spectral Data of Peptides With Amino Acid Sequences in a Protein Database". J. Am. Soc. Mass Spectrom, 5, 976-989 (1994).

Epton, R. "Peptides. Synthesis. Solid Phase Methods". Innovation and Perseptives in Solid Phase Synthesis. 57-63 (1990).

Fatica, A. et al. "Making Ribosomes". Curr. Opin. Cell Biol., 14, 313-318 (2002).

Gao, J. et al. "Screening Derived Peptide Libraries for Tight Binding Inhibitors to Carbonic Anhydrase II by Electrospray Ionization-Mass Spectrometry." J. Med. Chem. 39, 1949-1955 (1996).

Geysen, H. et al. "Isotope or mass encoding of combinatorial libraries". Chemistry & Biology, 3, 679-688 (1996).

Gerber, S.A. et al. "Absolute Quantification of Proteins and Phosphoproteins From Cell Lysates by Tandem MS". Proc. Natl. Acad. Sci., 100, 6940-6945 (2003).

Goodlett, D. et al. "Reduced Elution Speed Detection for Capillary Electrophoresis/Mass Spectrometry". J. Microl Sep, 5, 57-62 (1993).

Gonzalez, C.I. et al. "Nonsense-mediated mRNA Decay in Saccharomyces Cerevisiae". Gene, 274, 15-25 (2001).

Goshe, M.B. et al. "Stable Isotope-Coded Proteomic Mass Spectrometry". Curr Opin Biotechnol., 14, 101-109 (2003).

Griffin, T.J. et al. "Complementary Profiling of Gene Expression at the Transcriptome and Proteome Levels in Saccharomyces Cerevisiae". Mol. Cell Proteomics, 1, 323-333 (2002).

Gygi, S.P. et al. "Correlation Between Protein and mRNA Abundance In Yeast". Mol. Cell Biol., 19, 1720-1730 (1999).

Gygi S.P. et al. "Quantitative Analysis of Complex Protein Mixtures Using Isotope-Coded Affinity Tags". Nat. Biotechnol., 17, 994-999 (1999).

Ham, S. et al. "HLA-DO is a negative modulator of HLA-DM-mediated MHC class II peptide loading". Current Biology, 7, 950-957 (1997).

Han, D.K. et al. "Quantitative Profiling of Differentiation-induced Microsomal Proteins Using Isotope-Coded Affinity Tags and Mass Spectrometry". Natl. Biotechnol., 19, 946-951 (2001).

Hanley, S. et al. "Re-evaluation of the primary structure of *Ralstonia* eutropha phasing and implifications for polyhydroxylakanoic acid granule binding". FEBS Letters, 447, 99-105 (1999).

Harris et al. "An Improved Synthesis of 1-Methyl-2,5-piperazinedione". J. Heterocyclic Chem. 18, 423-424 (1981).

He, F. et al. Genome-Wide Analysis of mRNA's Regulated by the Nonsense-mediated and 5' to 3' mRNA Decay Pathways in Yeast. Mol. Cell, 12, 1439-1452 (2003).

Henion, J. et al. "Mass Spectrometric Investigations of Drug-Receptor Interactions". Therapeutic Drug Monitoring, 15, 563-569 (1993).

Henry, N.L. et al, Purification and Characterization of Yeast RNA Polymerase II General Initiation Factor g. J. Biol. Chem. 267, 23388-23392 (1992).

Hentze, M.W. et al. "A Perfect Message: RNA Surveillance And Nonsense-Mediated Decay". Cell, 96, 307-310 (1999).

Hermanson, G. et al. "The Chemistry of Reactive Groups". Bioconjugate Techniques, Chapter 2, 137-165.

Heyes, M. et al. "($^{18}$O) Quinolinic Acid: Its Esterification without Back Exchange for Use as Internal Standard in the Quantification of Brain and CSF Quinolinic Acid".

Höss, M. et al. "A human DNA editing enzyme homologous to the *Escherichia coli* DnaQ/MutD protein". The EMBO Journal, 18, 3868-3875 (1999).

Hughs, I. Et al. "Design of Self-Coded Combinatorial Libraries To Facilitate Direct Analysis of Ligands by Mass Spectrometry". J. Med. Chem., 41, 3804-3811 (1998).

Hsu, C. et al. Yeast cells lacking 5'-3' Exoribonuclease 1 Contain mRNA Species That are Poly (A) Deficient and Partially Lack The 5' Cap Structure. Mol. Cell. Biol., 13, 4826-4835 (1993).

Ibarrola, N. et al. A Novel Proteomic Approach For Specific Identification of Tyrosine Kinase Substrates Using 13C-Labeled Tyrosine. J. Biol. Chem. In press (2004).

Ju, Q. et al. "REB1, a Yeast DNA-Binding Protein With Many Targets, is Essential For Growth and Bears Some Resemblance to the Oncogene myb". Mol. Cell Biol., 10, 5226-5234 (1990).

Jung, g. et al. "Multiple Peptide Synthesis Methods and Their Applications". Angewandte Chemie, 31, 367-486 (1992).

Karimi-Busheri, F. et al. "Molecular Characterization of a Human DNA Kinase". The Journal of Biological Chemistry, 274, 24187-24194 (1999).

Kondo, H. et al. "p47 is a cofactor for p97-mediated membrane fusion". Nature, 388, 75-78 (1997).

Köster, H. et al. "A strategy for rapid and efficient DNA sequencing by mass spectrometry". Nature Biotechnology, 14, 1123-1128 (1996).

Krusic, P. et al. "Electron Spin Resonance Studies of Fluoroalkyl Radicals in Solution. III. Photolysis of Perfluoroketones and Adduct Formation". The Journal of Physical Chemistry, 78, 2036-2041 (1974).

Kurihara, T. et al. "Sec24p and Iss1p Function Interchangeably in Transport Vesicle Formation From The Endoplasmic Reticulum in Saccharomyces Cerevisiae". Mol. Biol. Cell, 11, 983-998 (2000).

Maderazo, A.B. et al. "Upf1p Control of Nonsense mRNA Translation is Regulated by Nmd2p and Upf3p". Mol. Cell Biol., 20, 4591-4603 (2000).

Mak, M. et al, "Stability of Asp-Pro Bond Under High and Low Energy Collision Induced Dissociation Conditions in the Immunodominant Epitope Region of Herpes Simplex Virion Glycoprotein D". Rapid Commun. Mass Spectrom, 12, 837-842 (1998).

Mangus, D.A. et al. "Pbp 1, A Factor Interacting With Saccharomyces Cerevisiae Poly(A)-Binding Protein, Regulates Polyadenylation". Mol. Cell Biol. 18, 7383-7396 (1998).

Martinovic S. et al. "Selective Incorporation of Isotopically Labeled Amino Acids For Identification of Intact Proteins on a Proteome-Wide Level". J. Mass Spectrom., 37, 99-107 (2002).

Masselon, C. et al. "Accurate Mass Multiplexed Tandem Mass Spectrometry for High-Throughput Polypeptide Identification from Mixtures". Anal. Chem., 72, 1918-1924 (2000).

Metzger, J. et al. "Analytical methods for the characterization of synthetic peptide libraries". Peptides, 481-482 (1992).

Metzger, J. et al. "Electrospray Mass Spectrmetry and Tandem Mass Spectrometry of Synthetic Multicomponent Peptide Mixtures: Determination of Composition and Purity". Analytical Biochemistry, 219, 261-277 (1994).

Metzger, J. et al. "Ion-Spray Mass Spectrometry and High-Performance Liquid Chromatography-Mass Spectrometry of Synthetic Peptide Libraries". Angew. Chem. Int. Ed. Engl., 6, 894-896 (1993).

Moore, R. et al. "A Microscale Electrospray Interface Incorporating a Monolithic, Poly(styrene-divinylbenzene) Support for On-Line Liquid Chromatography/Tandem Mass Spectrometry Analysis of Peptides and Proteins". Anal. Chem. 70, 4879-4884 (1998).

Nawrocki, J. et al, "Analysis of Combinatorial Libraries Using Electrospray Fourier Transform Ion Cyckotron Resonance Mass Spectrometry". Rapid Communication In Mass Spectrometry, 10, 1860-1864 (1996).

Nazarpack-Kandlousy, N. et al. "Regiochemical Tagging: A New Tool for Structural Characterization of Isomeric Components in Combinatorial Mixtures". J. Am. Chem. Soc., 122, 3358-3366 (2000).

Needels M. et al. "Generation and screening of an oligonucleotide-encoded synthetic peptide library". Proc. Natl. Acad. Sci. USA, 90, 10700-10704 (1993).

Nestler, H. et al. "A General Method for Molecular Tagging of Encoded Combinatorial Chemistry Libraries". J. Org. Chem, 59, 4723-4724 (1994).

Nikolaiev, V. et al. "Peptide-Encoding For Structure Determination of Nonsequence-able Polymers Within Libraries Synthesized and Tested on Solid-Phase Supports". Peptide Research, 3, 161-170, (1994).

Nutiu, R. et al. "Tripartite Molecular Beacons". Nucleic Acids Research, 18, 1-9 (2002).

Ohlmeyer, M. et al. "Complex synthetic chemical libraries indexed with molecular tags". Proc. Natl. Acad. Sci, USA, 90, 10922-10926 (1993).

Olejnik, J. et al. "Photocleavable biotin phosphoramidite for 5'-end labeling, affinity purification and phosphorylation of synthetic oligonucleotides". Nucleic Acids Research, 24, 361-366 (1996).

Olejnik, J. et al. "Photocleavable peptide-DNA conjugates: synthesis and applications to DNA analysis using MALDI-MS". Nucleic Acids Research, 23, 4626-4631 (1999).

Ong, S.E. et al. "Properties of 13C-Substituted Arginine in Stable Isotope Labeling By Amino Acids In Cell Culture (SILAC)". J. Proteome Res. 2, 173-181 (2003).

Ong, S.E. et al. "Stable Isotope Labeling By Amino Acids In Cell Culture SILAC, as a Simple And Accurate Approach to Expression Proteomics". Mol. Cell Proteomics, 1, 376-386 (2002).

Parker, K.C. et al. "Depth of Proteome Issues: A Yeast ICAT Reagent Study". Mol. Cell Proteomics, In Press (2004).

Pitha, J. et al. "Synthetic Analogs of Nucleic Acids". Biomedical Polymers, 271-297 (1980).

Perkins, D.N. et al. "Probability-Based Protein Identification By Searching Sequence Databases Using Mass Spectrometry Data". Electrophoresis, 20, 3551-3567 (1999).

Peterson, C.L. et al. "Characterization of the Yeast Swi1, SWI2, and SWI3 Genes, Which encode a Global Activator of Transcription". Cell, 68, 573-583 (1992).

Przybylski, M. et al, "Mass spectrometric approaches to molecular characterization of protein-nucleic acid interactions". Toxicology Letters, 82/83, 567-575 (1995).

Qiu, Y. et al. "Acid-Labile Isotype-Coded Extractants: A Class of Reagents for Quantitative Mass Spectrometric Analysis of Complex Protein Mixtures". Analytical Chemistry, 19, 4969-4979.

Rao, T. et al, TFA-NHS as bifunctional protecting agent: simultaneous protection and activation of amino carboxylic acids. Tetrahedron Letters, 43, 7793-7795 (2002).

Rautio, J. et al. "Synthesis And In Vitro Evaluation Of Novel Morpholinyl- and Methylpiperazinylacyloxyalkyl Prodrugs of 2-(6-Methoxy-2-naphthyl)propionic Acid (Naproxen) for Topical Drug Delivery". J. Med. Chem., 115, 1489-1494 (2000).

Ross, C. et al. "Two Dimensional Fourier Transform Ion Cyclotron Resonance Mass Spectrometry/Mass Spectrometry with Stored-Waveform Ion Radius Modulation". J. Am. Chem. Soc., 115, 7854-7861 (1993).

Sadler, I. et al. "A Yeast Gene Important For Protein Assembly Into the Endoplasmic Reticulum and the Nucleus Has Homology to Dnaj, an *Escherichia coli* Heat Shock Protein". J. Cell Biol. 109, 2665-2675 (1989).

Saghatelian, A. et al. "DNA Detection and Signal Amplification via an Engineered Allosteric Enzyme". J. Am. Chem. Soc. 125, 344-345 (2003).

Sakakibara S. et al., "A New Reagent For The P-Nitrophenylation of Carboxylic Acids". Bulletin of The Chemical Society of Japan, 8, 1231-1232 (1964).

Sakakibara, S. et al., "The Trifluoroacetate Method of Peptide Synthesis I. The Synthesis and Use of Trifluoroacetate Reagents". The Synthesis and Use of Trifluoroacetate Reagents, 11, 1979-1983 (1965).

Schröter, M. et al. "Genotyping of Hepatitis C Virus Types 1,2,3 and 4 by a One-Step LightCycler Method Using Three Different Pairs of Hybridization Probes". Journal of Clinical Microbiology, 6, 2046-2050 (2002).

Shevchenko, A. et al. "MALDI Quadrupole Time-of-Flight Mass Spectrometry: A Powerful Tool for Proteomic Research". Anal. Chem., 72, 2132-2141 (2000).

Shevchenko, A. et al. "Rapid 'de Novo' Peptide Sequencing By a Combination of Nanoelectrospray, Isotopic Labeling and a Quadrupole/Time-of-Flight Mass Spectrometer". Rapid Comm. In Mass Spectro., 11, 1015-1024 (1997).

Sickinger, A. et al. "Epitope mapping: synthetic approaches to the understanding of molecular regognition in the immune system". Pharmaceutical ACTA Helvetiac, 68, 3-20 (1993).

Stacey, M. et al, "A General Method of Esterification Using Trifluoracetic Anhydride". Nature, 8, 705.

Stevanovic, S. et al. "Multiple Sequence Analysis: Pool Sequencing of Synthetic and Natural Peptide Libraries". Analytical Biochemistry, 212, 212-220 (1993).

Stevanovic, S. et al. "Natural and Synthetic Peptide Pools: Characterization by Sequencing and Electrospray Mass Spectrometry". Bioorganic & Medical Chemistry Letters, 3, 431-436 (1993).

Stevens, A. et al. "Fragments of the Internal Transcribed Spacer 1 or Pre-rRNA Accumulate in Saccharomyces Cerevisiae Lacking 5'-3'Exoribonuclease 1". J. Bacteriol, 173, 7024-7028 (1991).

Tao, W.A. et al. "Advances in Quantitative Proteomics Via Stable Isotope Tagging and Mass Spectrometry". Curr Opin Biotechnol., 14, 110-118 (2003).

Thomas, D. et al. "Y SAM2 Encodes The Second Methionine S-Adenosyl Transferase in Saccharomyces Cerevisiae: Physiology and Regulation of Both Enzymes". Mol. Cell Biol., 8, 5132-5139 (1988).

Thompson, A. et al. "Tandem Mass Tags: A Novel Quantification Strategy for Comparative Analysis of Complex Protein Mixtures by MS/MS". Anal. Chem, 75, 1895-1904 (2003).

Tugal, T. et al. "The Orc4p and Orc5p Subunits of the Xenopus and the Human Origin Recognition Complex Are Related to Orc1p and Cdc6p". Journal of Biological Chemistry, 49, 32421-32429 (1998).

Veenstra, T. et al. "Proteome Analysis Using Selective Incorporation of Isotopically Labeled Amino Acids". American Soc. For Mass. Spect., 11, 78-82 (2000).

Wagner, D. et al. "Ratio Encoding Combinatorial Libraries with Stable Isotopes and their Utility in Pharmaceutical Research". Combinational Chemistry & High Throughput Screening, 3, 143-153 (1998).

Washburn, M.P. et al. "Reproducibility of Quantiative Proteomic Analyses of Complex Biological Mixtures by Multidimensional Protein Identification Technology". Anal. Chem., 75, 5054-5061 (2003).

Wentworth, P. et al. "Generating and analyzing combinatorial chemistry libraries". Analytical Chemistry, 9, 109-115 (1998).

Wegierski, T. et al. Bms1p, a G-domain-containig protein, Associates with Rcl1p and is Required For 18S rRNA Biogenesis in Yeast. RNA, 7, 1254-1267 (2001).

Wieboldt, R. et al. "Immunoaffinity Ultrafiltration with Ion Spray HPLC/MS for Screening Small-Molecule Libraries". Analytical Chemistry, 69, 1683-1691 (1997).

Williams, E. et al. "Hadamard Transform Measurement of Tandem Fourier-Transform Mass Spectra". Anal. Chem. 62, 698-703 (1990).

Winger, B. et al. "Characterization of Combinatorial Peptide Libraries by Electrospray Ionization Fourier Transform Mass Spectrometry". Rapid Comm. In Mass Spectrometry. 10, 1811-1813 (1996).

Wissner, A. et al, "Reaction of tert-Butyldimethylsilyl Esters with Oxalyl Chloride-DimethylformideL Preparation of Carboxylic Acid Chlorides Under Neutral Conditions". J. Org. Chem. 43, 3972-3974 (1978).

Yates, J.R. "Mass Spectrometry From genetics To Proteomics". TIG, 16, 5-8 (2000).

Yates, J.R. "Database Searching Using Mass Spectrometry Data". Electrophoresis, 19, 893-900 (1998).

Yates, N.E et al. "A novel N-terminal derivative designed to simplify peptide fragmentation". Proceedings of the 43$^{rd}$ ASMS Conference of Mass Spectrometry and Allied Topics, Atlanta, Georgia (May 21-26, 1996).

Young, J.D. et al. "Thymosin β 4 sulfoxide is an anti-inflammatory agent generated by monocytesin the presence of glucocorticoids". Nature Medicine, 12, 1424-1427.

Young, P. et al. "Alternative Mobile Phases For Enhanced HPLC Peptide Mapping". Millipore Bioforum, 4, (1993).

Zhang, X. et al. "B=N-Terminal peptide labeling strategy for incorporation of isotopic tags: a method for the determination of site-specific absolute phosphorylation stoichiometry". Rapid Comm. In Mass Spec., 16, 2325-2332 (2002).

Zhong, T. et al. The Yeast SIS 1 Protein, a DnaJ Homolog, is Required For The Initiation of Translation. Cell, 73, 1175-1186 (1993).

Zhou, H. et al. "Quantitive proteome analysis by solid-phase isotype tagging and mass spectrometry". Nature Biotechnology, 19, 512-515 (2002).

Barlett Jones, M., et al., "Peptide Ladder Sequencing by Mass Spectrometry Using a Novel, Volatile Degradation Reagent", Rapid Communications in Mass Spectrometry, vol. 8, 737-742 (1994).

Day, Richard et al, "N-Terminal Groups in Mass Spectrometry of Peptides. A Study Including Some New and Useful Derivatives", J. Org. Chem., vol. 38, No. 4, 1975 782-788.

Duffield, A. et al., "Mass Spectrometry in Structural and Stereochemical Problems LVIII. A Study of the Fragmentation Processes of Some Lactams", Contribution from the Department of Chemistry of Stanford University, Stanford, CA, Aug. 5, 1964, pp. 5536-5541.

Gatlin, C et al, "Copper (II) Amino Acid Complexes in the Bas Phase", J. Am. Chem. Soc. 1995, 117, 3637-3638.

Gatlin, C et al, Carboxylate and Amine Terminus Directed Fragmentations in Gaseous Dipeptide Complexes with Copper (II) and Diimine Ligands Formed by Electrospray, Anal. Chem. 1996, 68, 263-270.

Haralambidou, E., et al., "Effect of Distal Positional Isomerism on Peptide Fragmentation. A Comparison of Dimethylaminobenzylidene and Benzoyl Derivatives", Organic Mass Spectrometry, 10: 683-697 (1975).

Medzihradszky, Katalin et al, "Peptide Sequence Determination by Matrix-Assisted Laser Desorption Ionization Employing a Tandem Double Focusing Magnetic-Orthogonal Acceleration Time-of-Flight Mass Spectrometer", American Society for Mass Spectrometry, 1996, 7, 1-10.

Spengler, R et al, "Peptide Sequencing of Charged Derivatives by Postsource Decay MALDI Mass Spectrometry", International Journal of Mass Spectrometry and Ion Processes, 169/170 (1997) 127-140.

SuBmuth, R., et al, "Impact of Mass Spectrometry on Combinatorial Chemistry", Journal of Chromatography B, 725 (1999) 49-65.

Roth, Kenneth et al, "Charge Derivatization of Peptides for Analysis by Mass Spectrometry", Mass Spectrometry Reviews, 1998, 17, 255-274.

Zhu, Xuegong et al, "Peptide Quantification by Tandem Mass Spectrometry", Mass Spectrometry Reviews, 1996, 15, 213-240.

Peng, Junmin et al, "Proteomics: the move to mixtures", Journal of Mass Spectrometry, 2001: 36, 1083-1091.

Ross, Philip et al, "Investigation of Chemical Derivatization for Peptide CID Using LC-MALDI TOF MS/MS", Applied Biosystems Poster No. ThPF 250.

Huang, Yulin et al, "A Method for High Efficiency Peptide Sequencing Using Combined Enzymatic Digestion and Chemical Derivatization on MALDI MSMS", Applied Biosystems Poster No. 1159.

Sherman, Nicholas et al, "A Novel N-Terminal Derivative Designed to Simplify Peptide Fragmentation", Proceedings of the 43$^{rd}$ ASMS Conference on Mass Spectrometry and Allied Topics, Atlanta, Georgia, May 21-26, 1995, pp. 626-627.

Theodora W. Greene & Peter G.M. Wuts, Protective Groups in Organic Synthesis 3$^{rd}$ ed./John Wiley & Sons, Inc. © 1999, ISBN 0-471-16019-9.

Shetty, Umesha H. et al, "Piperazine Ring Cleavage in the Electron Impact Induced Fragmentation of Piperazine Type Phenothiazine Antipsychotic Agents", Biomedical Mass Spectrometry, vol. 10, No. 11, 1983, pp. 601-607.

Ross, Philip et al, "Investigation of Chemical Derivatization for Peptide CID Using LC-MALDI TOF MS/MS", Applied Biosystems Poster No. ThPF 250, ASMS Conference Jun. 8-Jun. 12, 2003.

Huang, Yulin et al, "A Method for High Efficiency Peptide Sequencing Using Combined Enzymatic Digestion and Chemical Derivatization on MALDI MSMS", Applied Biosystems Poster No. 1159, 6$^{th}$ International Symposium on Mass Spectrometry in the Health and Life Sciences, Aug. 24-28, 2003, San Francisco.

Brenner, S. et al. "Encoded Combinatorial Chemistry". Proc. Natl. Acad. Sci. USA 89, 5831-5383 (1992).

Gallop, M. et al. "Applications of Combinatorial Technologies to Drug Discovery. I. Background And Peptide Combinatoria Libraries". Journal of Medicinal Chemistry 9, 1233-1251 (1994).

Geysen, H. et al. "Strategies For Epitope Analysis Using Peptide Synthesis". Journal of Immunological Methods 102, 259-274 (1987).

Gordon, E. et al. "Applications of Combinatorial Technologies to Drug Discovery. 2. Combinatorial Organic Synthesis, Library Screening Strategies, and Future Directions". Journal of Medicinal Chemistry 10, 1385-1401 (1994).

Kerr, J. et al. "Encoded Combinatorial Peptide Libraries Containing Non-Natural Amino Acids". J. Am. Chem. Soc. 115, 2529-2531 (1993).

Kurth, M. et al. "Library-Based Lead Compound Discovery: Antoxidants By An Analogous Synthesis/Deconvolutive Assay Strategy". J. Org. Chem. 59, 5862-5864 (1994).

Moran E. J. et al. "Radio Frequency Tag Encoded Combinatorial Library Method For The Discovery of Tripeptide-Substituted Cinnamic Acid Inhibitors of The Protein Tyrosine Phosphates PTPIB". J. Am. Chem. Soc. 117, 10787-10788 (1995).

Needels, M. et al. "Generation And Screening Of An Oligonucleotide-Encoded Synthetic Peptide Library". Proc. Natl. Acad. Sci. USA 90, 10700-10704 (1993).

Nielsen, J. et al. "Synthetic Methods For The Implementation of Encoded Combinatorial Chemistry". J. Am. Chem. Soc. 115, 9812-9813 (1993).

Ohlmeyer, M. et al. "Complex Synthetic Chemical Libraries Indexed With Molecular Tags". Proc. Natl. Acad. Sci. USA 90, 10922-10926 (1993).

* cited by examiner

Mass Of Compounds X-XIII = 131.144

Mass Of Compounds XV and XVI = 129.151

Mass Of Compounds XVII and XVIII = 129.138

Note: The Mass Stated Is Only For The Reporter/Linker Combination

COMPOSITIONS AND KITS PERTAINING TO ANALYTE DETERMINATION

CROSS REFERENCE TO RELATED APPLICATIONS

This application claims the benefit of U.S. Provisional Patent Application Ser. No. 60/443,612, filed on Jan. 30, 2003, incorporated herein by reference.

FIELD OF THE INVENTION

This invention pertains to the field of analyte determination by mass analysis.

1. INTRODUCTION

Figure 1A:
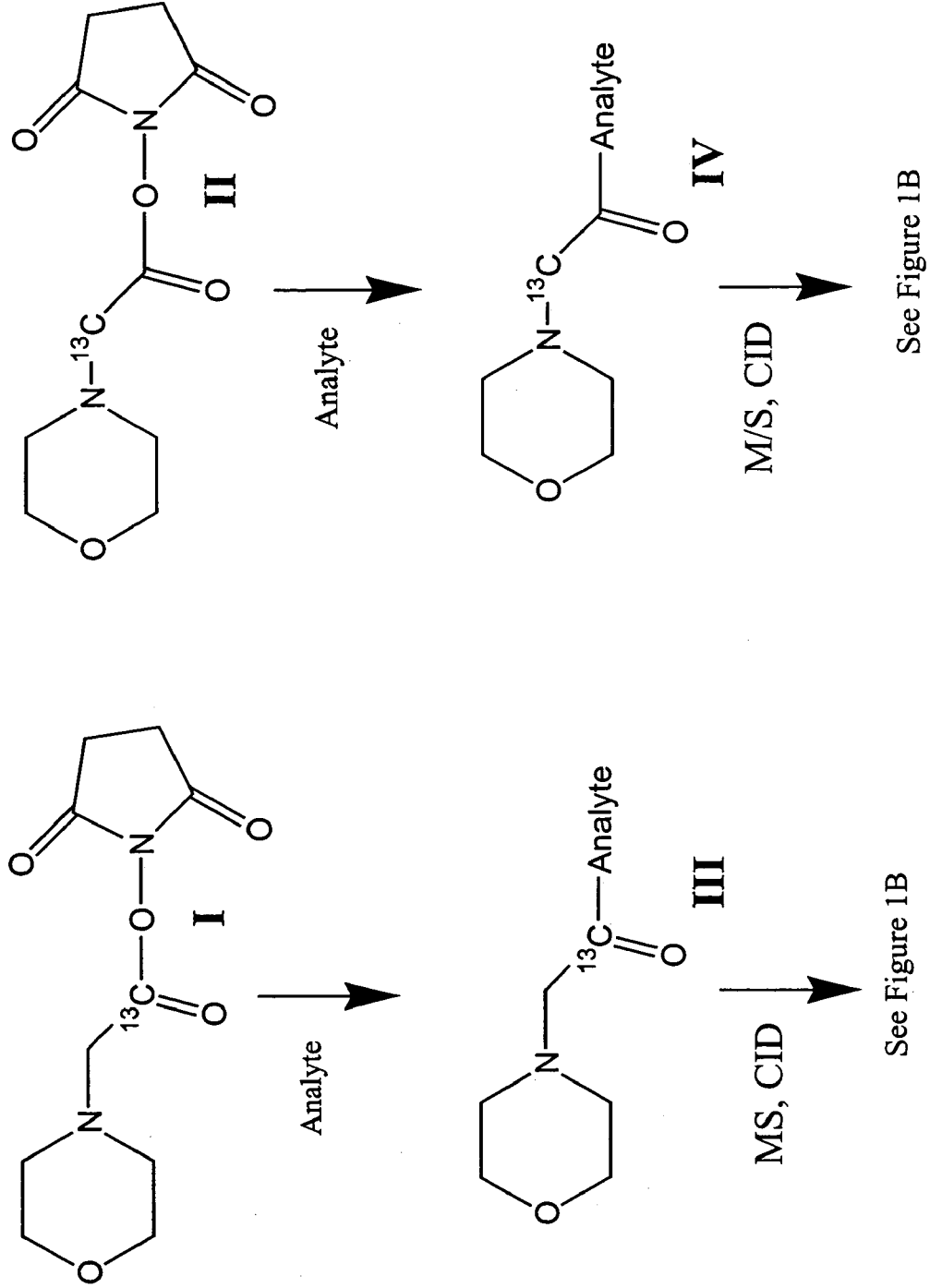
FIG. 1A illustrates the reaction of an analyte with two different isobaric labeling reagents (e.g. compounds I and II).

This invention pertains to methods, mixtures, kits and/or compositions for the determination of an analyte or analytes by mass analysis. An analyte can be any molecule of interest. Non-limiting examples of analytes include, but are not limited to, proteins, peptides, nucleic acids, carbohydrates, lipids, steroids and small molecules of less than 1500 daltons.

Analytes can be labeled by reaction of the analyte with a labeling reagent of the formula: RP—X—LK—Y—RG, or a salt thereof, wherein RG is a reactive group that reacts with the analyte and RP, X, LK and Y are described in more detail below. A labeled analyte therefore can have the general formula: RP—X—LK—Y-Analyte. Sets of isomeric or isobaric labeling reagents can be used to label the analytes of two or more different samples wherein the labeling reagent can be different for each different sample and wherein the labeling reagent can comprise a unique reporter, "RP", that can be associated with the sample from which the labeled analyte originated.

Hence, information, such as the presence and/or amount of the reporter, can be correlated with the presence and/or amount (often expressed as a concentration and/or quantity) of the analyte in a sample even from the analysis of a complex mixture of labeled analytes derived by mixing the products of the labeling of different samples. Analysis of such complex sample mixtures can be performed in a manner that allows for the determination of one or a plurality of analytes from the same or from multiple samples in a multiplex manner. Thus, the methods, mixtures, kits and/or compositions of this invention are particularly well suited for the multiplex analysis of complex sample mixtures. For example, they can be used in proteomic analysis and/or genomic analysis as well as for correlation studies related to genomic and proteomic analysis.

2. DEFINITIONS

For the purposes of interpreting of this specification, the following definitions will apply and whenever appropriate, terms used in the singular will also include the plural and vice versa:

a. As used herein, "analyte" refers to a molecule of interest that may be determined. Non-limiting examples of analytes can include, but are not limited to, proteins, peptides, nucleic acids (both DNA or RNA), carbohydrates, lipids, steroids and/or other small molecules with a molecular weight of less than 1500 daltons. The source of the analyte, or the sample comprising the analyte, is not a limitation as it can come from any source. The analyte or analytes can be natural or synthetic. Non-limiting examples of sources for the analyte, or the sample comprising the analyte, include but are not limited to cells or tissues, or cultures (or subcultures) thereof. Non-limiting examples of analyte sources include, but are not limited to, crude or processed cell lysates (including whole cell lysates), body fluids, tissue extracts or cell extracts. Still other non-limiting examples of sources for the analyte include but are not limited to fractions from a separations process such as a chromatographic separation or an electrophoretic separation. Body fluids include, but are not limited to, blood, urine, feces, spinal fluid, cerebral fluid, amniotic fluid, lymph fluid or a fluid from a glandular secretion. By processed cell lysate we mean that the cell lysate is treated, in addition to the treatments needed to lyse the cell, to thereby perform additional processing of the collected material. For example, the sample can be a cell lysate comprising one or more analytes that are peptides formed by treatment of the total protein component of a crude cell lysate with a proteolytic enzyme to thereby digest precursor protein or proteins.

b. As used herein, "fragmentation" refers to the breaking of a covalent bond.

c. As used herein, "fragment" refers to a product of fragmentation (noun) or the operation of causing fragmentation (verb).

d. It is well accepted that the mass of an atom or molecule can be approximated, often to the nearest whole number atomic mass unit or the nearest tenth or hundredth of an atomic mass unit. As used herein, "gross mass" refers to the absolute mass as well as to the approximate mass within a range where the use of isotopes of different atom types are so close in mass that they are the functional equivalent for the purpose of balancing the mass of the reporter and/or linker moieties (so that the gross mass of the reporter/linker combination is the same within a set or kit of isobaric or isomeric labeling reagents) whether or not the very small difference in mass of the different isotopes types used can be detected.

For example, the common isotopes of oxygen have a gross mass of 16.0 (actual mass 15.9949) and 18.0 (actual mass 17.9992), the common isotopes of carbon have a gross mass of 12.0 (actual mass 12.00000) and 13.0 (actual mass 13.00336) and the common isotopes of nitrogen have a gross mass of 14.0 (actual mass 14.0031) and 15.0 (actual mass 15.0001). Whilst these values are approximate, one of skill in the art will appreciate that if one uses the $^{18}O$ isotope in one reporter of a set, the additional 2 mass units (over the isotope of oxygen having a gross mass of 16.0) can, for example, be compensated for in a different reporter of the set comprising $^{16}O$ by incorporating, elsewhere in the reporter, two carbon $^{13}C$ atoms, instead of two $^{12}C$ atoms, two $^{15}N$ atoms, instead of two $^{14}N$ atoms or even one $^{13}C$ atom and one $^{15}N$ atom, instead of a $^{12}C$ and a $^{14}N$, to compensate for the $^{18}O$. In this way the two different reporters of the set are the functional mass equivalent (i.e. have the same gross mass) since the very small actual differences in mass between the use of two $^{13}C$ atoms (instead of two $^{12}C$ atoms), two $^{15}N$ atoms (instead of two $^{14}N$ atoms), one $^{13}C$ and one $^{15}N$ (instead of a $^{12}C$ and $^{14}N$) or one $^{18}O$ atom (instead of one $^{16}O$ atom), to thereby achieve an increase in mass of two Daltons, in all of the labels of the set or kit, is not an impediment to the nature of the analysis.

Figure 8:
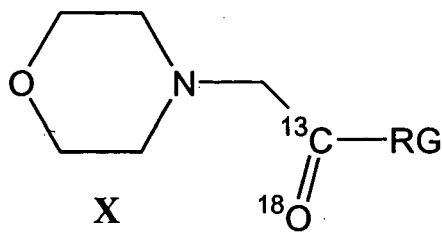
FIG. 8 is an illustration of two sets of isobaric labeling reagents wherein the same isotopes (compounds X–XIII) and different isotopes (compounds XV–XVIII) are used within the set to thereby achieve reporter/linker moieties of the same gross mass but each with a reporter moiety of a different gross mass within the set.
Figure 8:
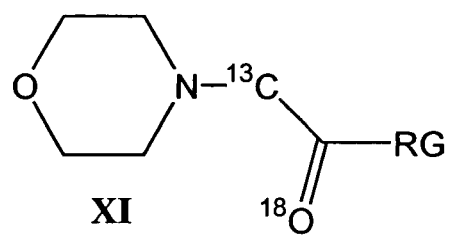
Figure 8:
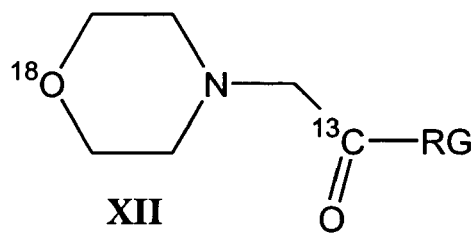
Figure 8:
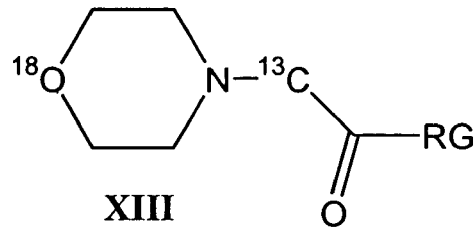
Figure 8:
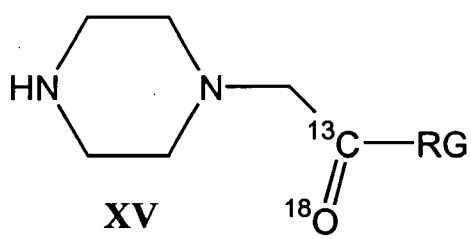
Figure 8:
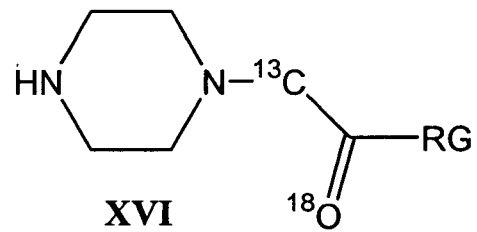
Figure 8:
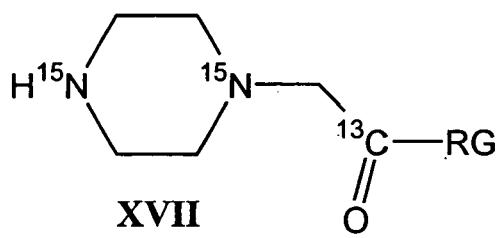
Figure 8:
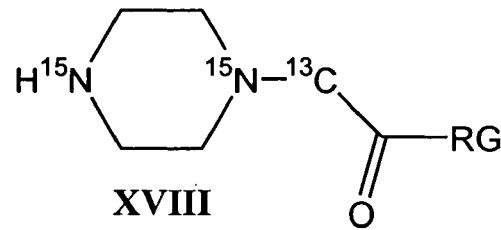

This can be illustrated with reference to FIG. 8. In FIG. 8, the reporter/linker combination of compound XVII (FIG. 8; chemical formula: $C_5{}^{13}CH_{10}{}^{15}N_2O$) has two $^{15}N$ atoms and one $^{13}C$ atom and a total theoretical mass of 129.138. By comparison, isobar XV (FIG. 8; chemical formula $C_5{}^{13}CH_{10}N_2{}^{18}O$) has one $^{18}O$ atom and one $^{13}C$ atom and a total theoretical mass of 129.151. Compounds XVII and XV are isobars that are structurally and chemically indistinguishable, except for heavy atom isotope content, although there is a slight absolute mass difference (mass 129.138 vs. mass 129.151 respectively). However, the gross mass of compounds XVII and XV is 129.1 for the purposes of this invention since this is not an impediment to the analysis whether or not the mass spectrometer is sensitive enough to measure the small difference between the absolute mass of isobars XVII and XV.

From FIG. 8, it is clear that the distribution of the same heavy atom isotopes within a structure is not the only consideration for the creation of sets of isomeric and/or isobaric labeling reagents. It is possible to mix heavy atom isotope types to achieve isomers or isobars of a desired gross mass. In this way, both the selection (combination) of heavy atom isotopes as well as their distribution is available for consideration in the production of the isomeric and/or isobaric labeling reagents useful for embodiments of this invention.

e. As used herein, "isotopically enriched" refers to a compound (e.g. labeling reagent) that has been enriched synthetically with one or more heavy atom isotopes (e.g. stable isotopes such as Deuterium, $^{13}C$, $^{15}N$, $^{18}O$, $^{37}Cl$ or $^{81}Br$). Because isotopic enrichment is not 100% effective, there can be impurities of the compound that are of lesser states of enrichment and these will have a lower mass. Likewise, because of over-enrichment (undesired enrichment) and because of natural isotopic abundance, there can be impurities of greater mass.

f. As used herein, "labeling reagent" refers to a moiety suitable to mark an analyte for determination. The term label is synonymous with the terms tag and mark and other equivalent terms and phrases. For example, a labeled analyte can also be referred to as a tagged analyte or a marked analyte. Accordingly the terms "label", "tag", "mark" and derivatives of these terms, are interchangeable and refer to a moiety suitable to mark, or that has marked, an analyte for determination.

g. As used herein, "support", "solid support" or "solid carrier" means any solid phase material upon which a labeling reagent can be immobilized. Immobilization can, for example, be used to label analytes or be used to prepare a labeling reagent, whether or not the labeling occurs on the support. Solid support encompasses terms such as "resin", "synthesis support", "solid phase", "surface" "membrane" and/or "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled-pore-glass (CPG), or reverse-phase silica. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression or other container, vessel, feature or location. A plurality of solid supports can be configured in an array at various locations, addressable for robotic delivery of reagents, or by detection methods and/or instruments.

h. As used herein, "natural isotopic abundance" refers to the level (or distribution) of one or more isotopes found in a compound based upon the natural prevalence of an isotope or isotopes in nature. For example, a natural compound obtained from living plant matter will typically contain about 0.6% $^{13}C$.

3. GENERAL

The Reactive Group:

The reactive group "RG" of the labeling reagent or reagents used in the method, mixture, kit and/or composition embodiments can be either an electrophile or a nucleophile that is capable of reacting with one or more reactive analytes of a sample. The reactive group can be preexisting or it can be prepared in-situ. In-situ preparation of the reactive group can proceed in the absence of the reactive analyte or it can proceed in the presence of the reactive analyte. For example, a carboxylic acid group can be modified in-situ with water-soluble carbodiimide (e.g. 1-(3-dimethylaminopropyl)-3- ethylcarbodiimide hydrochloride; EDC) to thereby prepare an electrophilic group that can be reacted with a nucleophile such as an amine group. In some embodiments, activation of the carboxylic acid group of a labeling reagent with EDC can be performed in the presence of an amine (nucleophile) containing analyte. In some embodiments, the amine (nucleophile) containing analyte can also be added after the initial reaction with EDC is performed. In other embodiments, the reactive group can be generated in-situ by the in-situ removal of a protecting group. Consequently, any existing or newly created reagent or reagents that can effect the derivatization of analytes by the reaction of nucleophiles and/or electrophiles are contemplated by the method, mixture, kit and/or composition embodiments of this invention.

Where the reactive group of the labeling reagent is an electrophile, it can react with a suitable nucleophilic group of the analyte or analytes. Where the reactive group of the labeling reagent is a nucleophile, it can react with a suitable electrophilic group of the analyte or analytes. Numerous pairs of suitable nucleophilic groups and electrophilic groups are known and often used in the chemical and biochemical arts. Non-limiting examples of reagents comprising suitable nucleophilic or electrophilic groups that can be coupled to analytes (e.g. such as proteins, peptides, nucleic acids, carbohydrates, lipids, steroids or other small molecules of less that 1500 daltons) to effect their derivatization, are described in the Pierce Life Science & Analytical Research Products Catalog & Handbook (a Perstorp Biotec Company), Rockford, Ill. 61105, USA. Other suitable reagents are well known in the art and are commercially available from numerous other vendors such as Sigma-Aldrich.

The reactive group of a labeling reagent can be an amine reactive group. For example the amine reactive group can be an active ester. Active esters are well known in peptide synthesis and refer to certain esters that are easily reacted with the N-α amine of an amino acid under conditions commonly used in peptide synthesis. The amine reactive active ester can be an N-hydroxysuccinimidyl ester, a N-hydroxysulfosuccininiidyl ester, a pentafluorophenyl ester, a 2-nitrophenyl ester, a 4-nitrophenyl ester, a 2,4-dinitrophenylester or a 2,4-dihalophenyl ester. For example, the alcohol or thiol group of an active ester can have the formula:

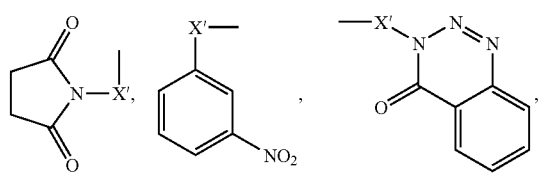

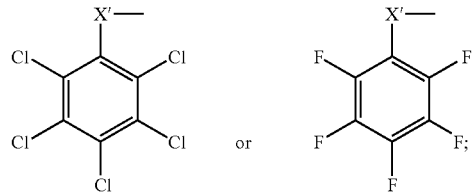

wherein X' is O or S, but preferably O. All of the foregoing being alcohol or thiol groups known to form active esters in the field of peptide chemistry wherein said alcohol or thiol group is displaced by the reaction of the N-α-amine of the amino acid with the carbonyl carbon of the ester. It should be apparent that the active ester (e.g. N-hydroxysuccinimidyl ester) of any suitable labelling/tagging reagent described herein could be prepared using well-known procedures (See: Greg T. Hermanson(1996). "The Chemistry of Reactive Groups" in "Bioconjugate Techniques" Chapter 2 pages 137–165, Academic Press, (New York); also see: Innovation And Perspectives In Solid Phase Synthesis, Editor: Roger Epton, SPCC (UK) Ltd, Birmingham, 1990). Methods for the formation of active esters of N-substituted piperazine acetic acids compounds that are representative examples of labelling reagents of the general formula: RP—X—LK—Y—RG, are described in co-pending and commonly owned U.S. patent application Ser. No. 10/751,354, incorporated herein by reference.

In another embodiment, the reactive group of the labeling reagent can be a mixed anhydride since mixed anhydrides are known to efficiently react with amine groups to thereby produce amide bonds.

The reactive group of a labeling reagent can be a thiol reactive group. For example, the thiol reactive group can be a malemide, an alkyl halide, an aryl halide of an α-halo-acyl. By halide or halo we mean atoms of fluorine, chlorine, bromine or iodine.

The reactive group of a labeling reagent can be a hydroxyl reactive group. For example, the hydroxyl reactive group can be a trityl-halide or a silyl-halide reactive moiety. The trityl-halide reactive moieties can be substituted (e.g. Y-methoxytrityl, Y-dimethoxytrityl, Y-trimethoxytrityl, etc) or unsubstituted wherein Y is defined below. The silyl reactive moieties can be alkyl substituted silyl halides, such as Y-dimethylsilyl, Y-ditriethylsilyl, Y-dipropylsilyl, Y-diisopropylsilyl, etc.) wherein Y is defined below.

The reactive group of the labeling reagent can be a nucleophile such as an amine group, a hydroxyl group or a thiol group.

The Reporter Moiety:

The reporter moiety of the labeling reagent or reagents used in the method, mixture, kit and/or composition embodiments is a group that has a unique mass (or mass to charge ratio) that can be determined. Accordingly, each reporter of a set can have a unique gross mass. Different reporters can comprise one or more heavy atom isotopes to achieve their unique mass. For example, isotopes of carbon ($^{12}C$, $^{13}C$ and $^{14}C$), nitrogen ($^{14}N$ and $^{15}N$), oxygen ($^{16}O$ and $^{18}O$) or hydrogen (hydrogen, deuterium and tritium) exist and can be used in the preparation of a diverse group of reporter moieties. Examples of stable heavy atom isotopes include $^{13}C$, $^{15}N$, $^{18}O$ and deuterium. These are not limiting as other light and heavy atom isotopes can also be used in the reporter. Basic starting materials suitable for preparing reporters comprising light and heavy atom isotopes are available from various commercial sources such as Cambridge Isotope Laboratories, Andover, Mass. (See: list or "basic starting materials" at www.isotope.com) and Isotec (a division of Sigma-Aldrich). Cambridge Isotope Laboratories and Isotec will also prepare desired compounds under custom synthesis contracts. Id.

A unique reporter can be associated with a sample of interest thereby labeling one or multiple analytes of that sample with the reporter. In this way information about the reporter can be associated with information about one or all of the analytes of the sample. However, the reporter need not be physically linked to an analyte when the reporter is determined. Rather, the unique gross mass of the reporter can, for example, be determined in a second mass analysis of a tandem mass analyzer, after ions of the labeled analyte are fragmented to thereby produce daughter fragment ions and detectable reporters. The determined reporter can be used to identify the sample from which a determined analyte originated. Further, the amount of the unique reporter, either relative to the amount of other reporters or relative to a calibration standard (e.g. an analyte labeled with a specific reporter), can be used to determine the relative or absolute amount (often expressed as a concentration and/or quantity) of analyte in the sample or samples. Therefore information, such as the amount of one or more analytes in a particular sample, can be associated with the reporter moiety that is used to label each particular sample. Where the identity of the analyte or analytes is also determined, that information can be correlated with information pertaining to the different reporters to thereby facilitate the determination of the identity and amount of each labeled analyte in one or a plurality of samples.

The reporter either comprises a fixed charge or is capable of becoming ionized. Because the reporter either comprises a fixed charge or is capable of being ionized, the labeling reagent might be isolated or used to label the reactive analyte in a salt or zwitterionic form. Ionization of the reporter facilitates its determination in a mass spectrometer. Accordingly, the reporter can be determined as an ion, sometimes referred to as a signature ion. When ionized, the reporter can comprise one or more net positive or negative charges. Thus, the reporter can comprise one or more acidic groups or basic groups since such groups can be easily ionized in a mass spectrometer. For example, the reporter can comprise one or more basic nitrogen atoms (positive charge) or one or more ionizable acidic groups such as a carboxylic acid group, sulfonic acid group or phosphoric acid group (negative charge). Non-limiting examples of reporters comprising a basic nitrogen include, substituted or unsubstituted, morpholines, piperidines or piperazines.

The reporter can be a 5, 6 or 7 membered heterocyclic ring comprising a ring nitrogen atom that is N-alkylated with a substituted or unsubstituted acetic acid moiety to which the analyte is linked through the carbonyl carbon of the N-alkyl acetic acid moiety, wherein each different label comprises one or more heavy atom isotopes. The heterocyclic ring can be substituted or unsubstituted. The heterocyclic ring can be aliphatic or aromatic. Possible substituents of the heterocylic moiety include alkyl, alkoxy and aryl groups. The substituents can comprise protected or unprotected groups, such as amine, hydroxyl or thiol groups, suitable for linking the analyte to a support. The heterocyclic ring can comprise additional heteroatoms such as one or more nitrogen, oxygen or sulfur atoms.

The reporter can be selected so that it does not substantially sub-fragment under conditions typical for the analysis of the analyte. The reporter can be chosen so that it does not substantially sub-fragment under conditions of dissociative energy applied to cause fragmentation of both bonds X and Y of at least a portion of selected ions of a labeled analyte in a mass spectrometer. By "does not substantially sub-fragment" we mean that fragments of the reporter are difficult or impossible to detect above background noise when applied to the successful analysis of the analyte of interest. The gross mass of a reporter can be intentionally selected to be different as compared with the mass of the analyte sought to be determined or any of the expected fragments of the analyte. For example, where proteins or peptides are the analytes, the reporter's gross mass can be chosen to be different as compared with any naturally occurring amino acid or peptide, or expected fragments thereof. This can facilitate analyte determination since, depending on the analyte, the lack of any possible components of the sample having the same coincident mass can add confidence to the result of any analysis.

Figure 6:
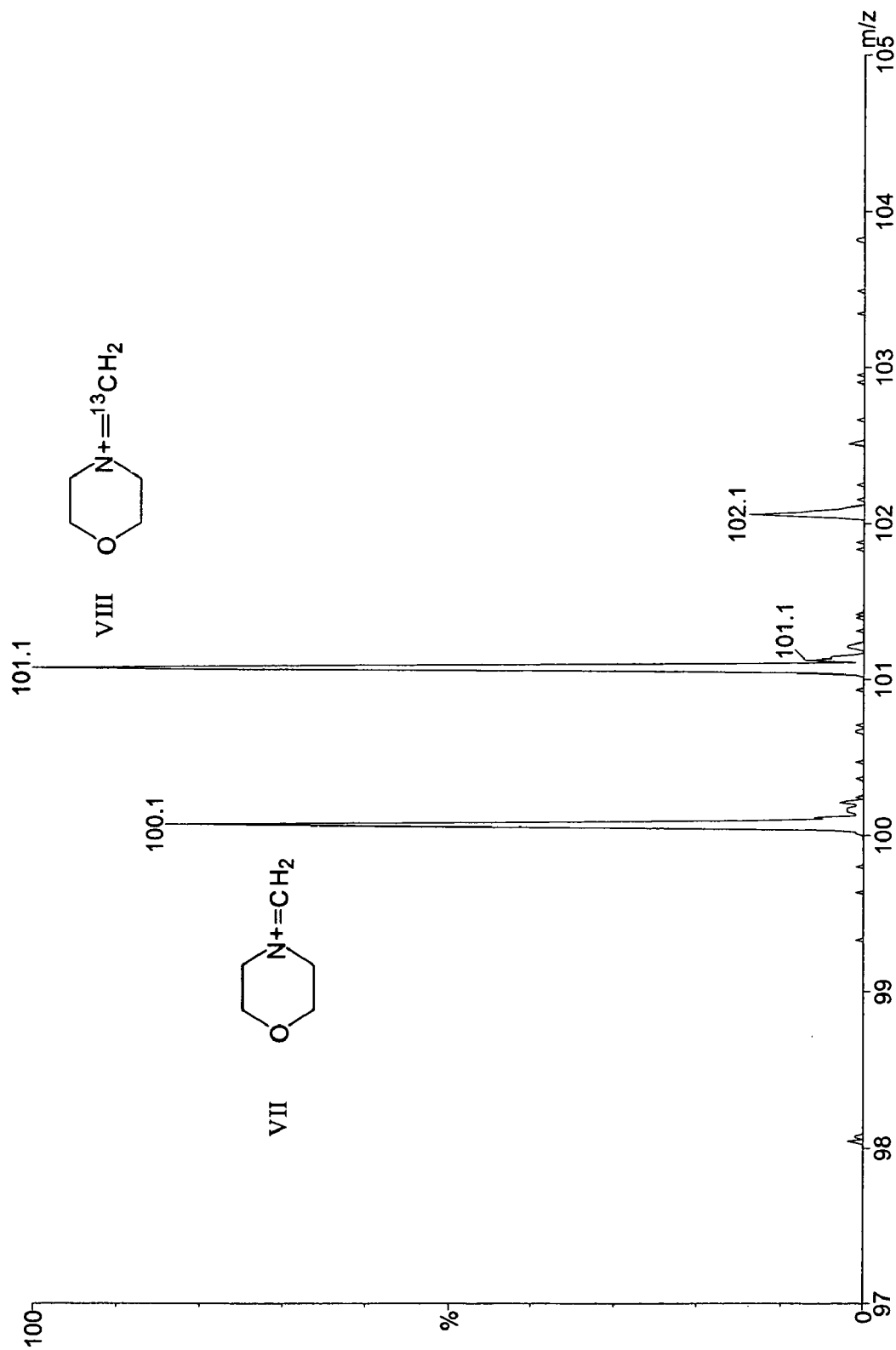
FIG. 6 is an expansion plot of a mass spectrum of two reporters (i.e. signature ions) as determined in the second mass analysis.

The reporter can be a small molecule that is non-polymeric. The reporter does not have to be a biopolymer (e.g. a peptide, a protein or a nucleic acid) or a component of a biopolymer (e.g. an amino acid, a nucleoside or a nucleotide). The gross mass of a reporter can be less than 250 Daltons. Such a small molecule can be easily determined in the second mass analysis, free from other components of the sample having the same coincident mass in the first mass analysis. In this context, the second mass analysis can be performed, typically in a tandem mass spectrometer, on selected ions that are determined in the first mass analysis. Because ions of a particular mass to charge ratio can be specifically selected out of the first mass analysis for possible fragmentation and further mass analysis, the non-selected ions from the first mass analysis are not carried forward to the second mass analysis and therefore do not contaminate the spectrum of the second mass analysis. Furthermore, the sensitivity of a mass spectrometer and the linearity of the detector (for purposes of quantitation) can be quite robust in this low mass range. Additionally, the present state of mass spectrometer technology can allow for baseline mass resolution of less than one Dalton in this mass range (See for example: FIG. 6). These factors may prove to be useful advancements to the state of the art.

The Linker Moiety:

The linker moiety of the labeling reagent or reagents used with the method, mixture, kit and/or composition embodiments links the reporter to the analyte or the reporter to the reactive group depending on whether or not a reaction with the analyte has occurred. The linker can be selected to produce a neutral species when both bonds X and Y are fragmented (i.e. undergoes neutral loss upon fragmentation of both bonds X and Y). The linker can be a very small moiety such as a carbonyl or thiocarbonyl group. For example, the linker can comprise at least one heavy atom isotope and comprise the formula:

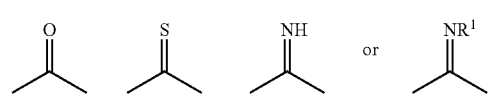

wherein R¹ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms. The linker can be a larger moiety. The linker can be a polymer or a biopolymer. The linker can be designed to sub-fragment when subjected to dissociative energy levels; including sub-fragmentation to thereby produce only neutral fragments of the linker.

The linker moiety can comprise one or more heavy atom isotopes such that its mass compensates for the difference in gross mass between the reporters for each labeled analyte of a mixture or for the reagents of set and/or kit. Moreover, the aggregate gross mass (i.e. the gross mass taken as a whole) of the reporter/linker combination can be the same for each labeled analyte of a mixture or for the reagents of set and/or kit. More specifically, the linker moiety can compensate for the difference in gross mass between reporters of labeled analytes from different samples wherein the unique gross mass of the reporter correlates with the sample from which the labeled analyte originated and the aggregate gross mass of the reporter/linker combination is the same for each labeled analyte of a sample mixture regardless of the sample from which it originated. In this way, the gross mass of identical analytes in two or more different samples can have the same gross mass when labeled and then mixed to produce a sample mixture.

For example, the labeled analytes, or the reagents of a set and/or kit for labeling the analytes, can be isomers or isobars. Thus, if ions of a particular mass to charge ratio (taken from the sample mixture) are selected (i.e. selected ions) in a mass spectrometer from an initial mass analysis of the sample mixture, identical analytes from the different samples that make up the sample mixture are represented in the selected ions in proportion to their respective concentration and/or quantity in the sample mixture. Accordingly, the linker not only links the reporter to the analyte, it also can serve to compensate for the differing masses of the unique reporter moieties to thereby harmonize the gross mass of the reporter/linker combination in the labeled analytes of the various samples.

Because the linker can act as a mass balance for the reporter in the labeling reagents, such that the aggregate gross mass of the reporter/linker combination is the same for all reagents of a set or kit, the greater the number of atoms in the linker, the greater the possible number of different isomeric/isobaric labeling reagents of a set and/or kit. Stated differently, generally the greater the number of atoms that a linker comprises, the greater number of potential reporter/linker combinations exist since isotopes can be substituted at most any position in the linker to thereby produce isomers or isobars of the linker portion wherein the linker portion is used to offset the differing masses of the reporter portion and thereby create a set of reporter/linker isomers or isobars. Such diverse sets of labeling reagents are particularly well suited for multiplex analysis of analytes in the same and/or different samples.

The total number of labeling reagents of a set and/or kit can be two, three, four, five, six, seven, eight, nine, ten or more. The diversity of the labeling reagents of a set or kit is limited only by the number of atoms of the reporter and linker moieties, the heavy atom isotopes available to substitute for the light isotopes and the various synthetic configurations in which the isotopes can be synthetically placed. As suggested above however, numerous isotopically enriched basic starting materials are readily available from manufacturers such as Cambridge Isotope Laboratories and Isotec. Such isotopically enriched basic starting materials can be used in the synthetic processes used to produce sets of isobaric and isomeric labeling reagents or be used to produce the isotopically enriched starting materials that can be used in the synthetic processes used to produce sets of isobaric and isomeric labeling reagents. Some examples of the preparation of isobaric labeling reagents suitable for use in a set of labeling reagents can be found in the Examples section, below.

The Reporter/Linker Combination:

The labeling reagents described herein comprise reporters and linkers that are linked through the bond X. As described above, the reporter/linker combination can be identical in gross mass for each member of a set and/or kit of labeling reagents. Moreover, bond X of the reporter/linker combination of the labeling reagents can be designed to fragment, in at least a portion of the selected ions, when subjected to dissociative energy levels thereby releasing the reporter from the analyte. Accordingly, the gross mass of the reporter (as a m/s ratio) and its intensity can be observed directly in MS/MS analysis.

The reporter/linker combination can comprise various combinations of the same or different heavy atom isotopes amongst the various labeling reagents of a set or kit. In the scientific literature this has sometimes been referred to as coding or isotope coding. For example, Abersold et al. has disclosed the isotope coded affinity tag (ICAT; see WO00/11208). In one respect, the reagents of Abersold et al. differ from the labeling reagents of this invention in that Abersold does not teach two or more same mass labeling reagents such as isomeric or isobaric labeling reagents.

Mass Spectrometers/Mass Spectrometry (MS):

The methods of this invention can be practiced using tandem mass spectrometers and other mass spectrometers that have the ability to select and fragment molecular ions. Tandem mass spectrometers (and to a lesser degree single-stage mass spectrometers) have the ability to select and fragment molecular ions according to their mass-to-charge (m/z) ratio, and then record the resulting fragment (daughter) ion spectra. More specifically, daughter fragment ion spectra can be generated by subjecting selected ions to dissociative energy levels (e.g. collision-induced dissociation (CID)). For example, ions corresponding to labeled peptides of a particular m/z ratio can be selected from a first mass analysis, fragmented and reanalyzed in a second mass analysis. Representative instruments that can perform such tandem mass analysis include, but are not limited to, magnetic four-sector, tandem time-of-flight, triple quadrupole, ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix-assisted laser desorption ionization (MALDI). Ionization sources can be used to generate charged species for the first mass analysis where the analytes do not already possess a fixed charge. Additional mass spectrometry instruments and fragmentation methods include post-source decay in MALDI-MS instruments and high-energy CID using MALDI-TOF(time of flight)-TOF MS. For a recent review of tandem mass spectrometers please see: R. Aebersold and D. Goodlett, *Mass Spectrometry in Proteomics. Chem. Rev.* 101: 269–295 (2001).

Fragmentation by Dissociative Energy Levels:

It is well accepted that bonds can fragment as a result of the processes occurring in a mass spectrometer. Moreover, bond fragmentation can be induced in a mass spectrometer by subjecting ions to dissociative energy levels. For example, the dissociative energy levels can be produced in a mass spectrometer by collision-induced dissociation (CID). Those of ordinary skill in the art of mass spectrometry will appreciate that other exemplary techniques for imposing dissociative energy levels that cause fragmentation include, but are not limited to, photo dissociation, electron capture and surface induced dissociation.

The process of fragmenting bonds by collision-induced dissociation involves increasing the kinetic energy state of selected ions, through collision with an inert gas, to a point where bond fragmentation occurs. For example, kinetic energy can be transferred by collision with an inert gas (such as nitrogen, helium or argon) in a collision cell. The amount of kinetic energy that can be transferred to the ions is proportional to the number of gas molecules that are allowed to enter the collision cell. When more gas molecules are present, a greater amount of kinetic energy can be transferred to the selected ions, and less kinetic energy is transferred when there are fewer gas molecules present.

It is therefore clear that the dissociative energy level in a mass spectrometer can be controlled. It is also well accepted that certain bonds are more labile than other bonds. The lability of the bonds in an analyte or the reporter/linker moiety depends upon the nature of the analyte or the reporter/linker moiety. Accordingly, the dissociative energy levels can be adjusted so that the analytes and/or the labels (e.g. the reporter/linker combinations) can be fragmented in a manner that is determinable. One of skill in the art will appreciate how to make such routine adjustments to the components of a mass spectrometer to thereby achieve the appropriate level of dissociative energy to thereby fragment at least a portion of ions of labeled analytes into ionized reporter moieties and daughter fragment ions.

For example, dissociative energy can be applied to ions that are selected/isolated from the first mass analysis. In a tandem mass spectrometer, the extracted ions can be subjected to dissociative energy levels and then transferred to a second mass analyzer. The selected ions can have a selected mass to charge ratio. The mass to charge ratio can be within a range of mass to charge ratios depending upon the characteristics of the mass spectrometer. When collision induced dissociation is used, the ions can be transferred from the first to the second mass analyzer by passing them through a collision cell where the dissociative energy can be applied to thereby produce fragment ions. For example the ions sent to the second mass analyzer for analysis can include some, or a portion, of the remaining (unfragmented) selected ions, as well as reporter ions (signature ions) and daughter fragment ions of the labeled analyte.

Analyte Determination by Computer Assisted Database Analysis:

In some embodiments, analytes can be determined based upon daughter-ion fragmentation patterns that are analyzed by computer-assisted comparison with the spectra of known or "theoretical" analytes. For example, the daughter fragment ion spectrum of a peptide ion fragmented under conditions of low energy CID can be considered the sum of many discrete fragmentation events. The common nomenclature differentiates daughter fragment ions according to the amide bond that breaks and the peptide fragment that retains charge following bond fission. Charge-retention on the N-terminal side of the fissile amide bond results in the formation of a b-type ion. If the charge remains on the C-terminal side of the broken amide bond, then the fragment ion is referred to as a y-type ion. In addition to b- and y-type ions, the CID mass spectrum may contain other diagnostic fragment ions (daughter fragment ions). These include ions generated by neutral loss of ammonia (−17 amu) from glutamine, lysine and arginine or the loss of water (−18 amu) from hydroxyl-containing amino acids such as seine and threonine. Certain amino acids have been observed to fragment more readily under conditions of low-energy CID than others. This is particularly apparent for peptides containing proline or aspartic acid residues, and even more so at aspartyl-proline bonds (Mak, M. et al., *Rapid Commun. Mass Spectrom.*, 12: 837–842) (1998). Accordingly, the peptide bond of a Z"-pro dimer or Z"-asp dimer, wherein Z" is any natural amino acid, pro is proline and asp is aspartic acid, will tend to be more labile as compared with the peptide bond between all other amino acid dimer combinations.

For peptide and protein samples therefore, low-energy CID spectra contain redundant sequence-specific information in overlapping b- and y-series ions, internal fragment ions from the same peptide, and immonium and other neutral-loss ions. Interpreting such CID spectra to assemble the amino acid sequence of the parent peptide de novo is challenging and time-consuming. The most significant advances in identifying peptide sequences have been the development of computer algorithms that correlate peptide CID spectra with peptide sequences that already exist in protein and DNA sequence databases. Such approaches are exemplified by programs such as SEQUEST (Eng, J. et al. *J. Am. Soc. Mass Spectrom.*, 5: 976–989 (1994)) and MASCOT (Perkins, D. et al. *Electrophoresis*, 20: 3551–3567 (1999)).

In brief, experimental peptide CID spectra (MS/MS spectra) are matched or correlated with 'theoretical' daughter fragment ion spectra computationally generated from peptide sequences obtained from protein or genome sequence databases. The match or correlation is based upon the similarities between the expected mass and the observed mass of the daughter fragment ions in MS/MS mode. The potential match or correlation is scored according to how well the experimental and 'theoretical' fragment patterns coincide. The constraints on databases searching for a given peptide amino acid sequence are so discriminating that a single peptide CID spectrum can be adequate for identifying any given protein in a whole-genome or expressed sequence tag (EST) database. For other reviews please see: Yates, J. R. Trends, *Genetics*, 16: 5–8 (2000) and Yates, J. R., *Electrophoresis* 19: 893–900 (1998).

Accordingly, daughter fragment ion analysis of MS/MS spectra can be used not only to determine the analyte of a labeled analyte, it can also be used to determine analytes from which the determined analyte originated. For example, identification of a peptide in the MS/MS analysis can be can be used to determine the protein from which the peptide was cleaved as a consequence of an enzymatic digestion of the protein. It is envisioned that such analysis can be applied to other analytes, such as nucleic acids.

Bonds X and Y:

X is a bond between an atom of the reporter and an atom of the linker. Y is a bond between an atom of the linker and an atom of either the reactive group or, if the labeling reagent has been reacted with a reactive analyte, the analyte. Bonds X and Y of the various labeling reagents (i.e. RP—X—LK—Y—RG) that can be used in the embodiments of this invention can fragment, in at least a portion of selected ions, when subjected to dissociative energy levels.

Therefore, the dissociative energy level can be adjusted in a mass spectrometer so that both bonds X and Y fragment in at least a portion of the selected ions of the labeled analytes (i.e. RP—X—LK—Y-Analyte). Fragmentation of bond X releases the reporter from the analyte so that the reporter can be determined independently from the analyte. Fragmentation of bond Y releases the reporter/linker combination from the analyte, or the linker from the analyte, depending on whether or not bond X has already been fragmented. Bond Y can be more labile than bond X. Bond X can be more labile than bond Y. Bonds X and Y can be of the same relative lability.

When the analyte of interest is a protein or peptide, the relative lability of bonds X and Y can be adjusted with regard to an amide (peptide) bond. Bond X, bond Y or both bonds X and Y can be more, equal or less labile as compared with a typical amide (peptide) bond. For example, under conditions of dissociative energy, bond X and/or bond Y can be less prone to fragmentation as compared with the peptide bond of a Z"-pro dimer or Zr"-asp dimer, wherein Z" is any natural amino acid, pro is proline and asp is aspartic acid. In some embodiments, bonds X and Y will fragment with approximately the same level of dissociative energy as a typical amide bond. In some embodiments, bonds X and Y will fragment at a greater level of dissociative energy as compared with a typical amide bond.

Bonds X and Y can also exist such that fragmentation of bond Y results in the fragmentation of bond X, and vice versa. In this way, both bonds X and Y can fragment essentially simultaneously such that no substantial amount of analyte, or daughter fragment ion thereof, comprises a partial label in the second mass analysis. By "substantial amount of analyte" we mean that less than 25%, and preferably less than 10%, partially labeled analyte can be determined in the MS/MS spectrum.

Because there can be a clear demarcation between labeled and unlabeled fragments of the analyte in the spectra of the second mass analysis (MS/MS), this feature can simplify the identification of the analytes from computer assisted analysis of the daughter fragment ion spectra. Moreover, because the fragment ions of analytes can, in some embodiments, be either fully labeled or unlabeled (but not partially labeled) with the reporter/linker moiety, there can be little or no scatter in the masses of the daughter fragment ions caused by isotopic distribution across fractured bonds such as would be the case where isotopes were present on each side of a single labile bond of a partially labeled analyte routinely determined in the second mass analysis.

Sample Processing:

In certain embodiments of this invention, a sample can be processed prior to, as well as after, labeling of the analytes. The processing can facilitate the labeling of the analytes. The processing can facilitate the analysis of the sample components. The processing can simplify the handling of the samples. The processing can facilitate two or more of the foregoing.

For example, a sample can be treated with an enzyme. The enzyme can be a protease (to degrade proteins and peptides), a nuclease (to degrade nucleic acids) or some other enzyme. The enzyme can be chosen to have a very predictable degradation pattern. Two or more proteases and/or two or more nuclease enzymes may also be used together, or with other enzymes, to thereby degrade sample components.

For example, the proteolytic enzyme trypsin is a serine protease that cleaves peptide bonds between lysine or arginine and an unspecific amino acid to thereby produce peptides that comprise an amine terminus (N-terminus) and lysine or arginine carboxyl terminal amino acid (C-terminus). In this way the peptides from the cleavage of the protein are predictable and their presence and/or quantity, in a sample from a trypsin digest, can be indicative of the presence and/or quantity of the protein of their origin. Moreover, the free amine termini of a peptide can be a good nucleophile that facilitates its labeling. Other exemplary proteolytic enzymes include papain, pepsin, ArgC, LysC, V8 protease, AspN, pronase, chymotrypsin and carboxypeptid[e]ase C.

For example, a protein (e.g. protein Z''') might produce three peptides (e.g. peptides B, C and D) when digested with a protease such as trypsin. Accordingly, a sample that has been digested with a proteolytic enzyme, such as trypsin, and that when analyzed is confirmed to contain peptides B, C and D, can be said to have originally comprised the protein Z'''. The quantity of peptides B, C and D will also correlate with the quantity of protein Z''' in the sample that was digested. In this way, any determination of the identity and/or quantify of one or more of peptides B, C and D in a sample (or a fraction thereof), can be used to identify and/or quantify protein Z'''in the original sample (or a fraction thereof).

Because activity of the enzymes is predictable, the sequence of peptides that are produced from degradation of a protein of known sequence can be predicted. With this information, "theoretical" peptide information can be generated. A determination of the "theoretical" peptide fragments in computer assisted analysis of daughter fragment ions (as described above) from mass spectrometry analysis of an actual sample can therefore be used to determine one or more peptides or proteins in one or more unknown samples.

Separation of the Sample Mixture:

In some embodiments the processing of a sample or sample mixture of labeled analytes can involve separation. For example, a sample mixture comprising differentially labeled analytes from different samples can be prepared. By differentially labeled we mean that each of the labels comprises a unique property that can be identified (e.g. comprises a unique reporter moiety that produces a unique "signature ion" in MS/MS analysis). In order to analyze the sample mixture, components of the sample mixture can be separated and mass analysis performed on only a fraction of the sample mixture. In this way, the complexity of the analysis can be substantially reduced since separated analytes can be individually analyzed for mass thereby increasing the sensitivity of the analysis process. Of course the analysis can be repeated one or more time on one or more additional fractions of the sample mixture to thereby allow for the analysis of all fractions of the sample mixture.

Separation conditions under which identical analytes that are differentially labeled co-elute at a concentration, or in a quantity, that is in proportion to their abundance in the sample mixture can be used to determine the amount of each labeled analyte in each of the samples that comprise the sample mixture provided that the amount of each sample added to the sample mixture is known. Accordingly, in some embodiments, separation of the sample mixture can simplify the analysis whilst maintaining the correlation between signals determined in the mass analysis (e.g. MS/MS analysis) with the amount of the differently labeled analytes in the sample mixture.

The separation can be performed by chromatography. For example, liquid chromatography/mass spectrometry (LC/

MS) can be used to effect such a sample separation and mass analysis. Moreover, any chromatographic separation process suitable to separate the analytes of interest can be used. For example, the chromatographic separation can be normal phase chromatography, reversed-phase chromatography, ion-exchange chromatography, size exclusion chromatography or affinity chromatorgraphy.

The separation can be performed electrophoretically. Non-limiting examples of electrophoretic separations techniques that can be used include, but are not limited to, 1D electrophoretic separation, 2D electrophoretic separation and/or capillary electrophoretic separation.

An isobaric labeling reagent or a set of reagents can be used to label the analytes of a sample. Isobaric labeling reagents are particularly useful when a separation step is performed because the isobaric labels of a set of labeling reagents are structurally and chemically indistinguishable (and can be indistinguishable by gross mass until fragmentation removes the reporter from the analyte). Thus, all analytes of identical composition that are labeled with different isobaric labels can chromatograph in exactly the same manner (i.e. co-elute). Because they are structurally and chemically indistinguishable, the eluent from the separation process can comprise an amount of each isobarically labeled analyte that is in proportion to the amount of that labeled analyte in the sample mixture. Furthermore, from the knowledge of how the sample mixture was prepared (portions of samples, an other optional components (e.g. calibration standards) added to prepare the sample mixture), it is possible to relate the amount of labeled analyte in the sample mixture back to the amount of that labeled analyte in the sample from which it originated.

The labeling reagents can also be isomeric. Although isomers can sometimes be chromatographically separated, there are circumstances, that are condition dependent, where the separation process can be operated to co-elute all of the identical analytes that are differentially labeled wherein the amount of all of the labeled analytes exist in the eluent in proportion to their concentration and/or quantity in the sample mixture.

As used herein, isobars differ from isomers in that isobars are structurally and chemically indistinguishable compounds (except for isotopic content and/or distribution) of the same nominal gross mass (See for example, FIG. 1) whereas isomers are structurally and/or chemically distinguishable compounds of the same nominal gross mass.

Relative and Absolute Quantitation of Analytes:

In some embodiments, the relative quantitation of differentially labeled identical analytes of a sample mixture is possible. Relative quantitation of differentially labeled identical analytes is possible by comparison of the relative amounts of reporter (e.g. area or height of the peak reported) that are determined in the second mass analysis for a selected, labeled analyte observed in a first mass analysis. Put differently, where each reporter can be correlated with information for a particular sample used to produce a sample mixture, the relative amount of that reporter, with respect to other reporters observed in the second mass analysis, is the relative amount of that analyte in the sample mixture. Where components combined to form the sample mixture are known, the relative amount of the analyte in each sample used to prepare the sample mixture can be back calculated based upon the relative amounts of reporter observed for the ions of the labeled analyte selected from the first mass analysis. This process can be repeated for all of the different labeled analytes observed in the first mass analysis. In this way, the relative amount (often expressed in terms of concentration and/or quantity) of each reactive analyte, in each of the different samples used to produce the sample mixture, can be determined.

In other embodiments, absolute quantitation of analytes can be determined. For these embodiments, a known amount of one or more differentially labeled analytes (the calibration standard or calibration standards) can be added to the sample mixture. The calibration standard can be an expected analyte that is labeled with an isomeric or isobaric label of the set of labels used to label the analytes of the sample mixture provided that the reporter for the calibration standard is unique as compared with any of the samples used to form the sample mixture. Once the relative amount of reporter for the calibration standard, or standards, is determined with relation to the relative amounts of the reporter for the differentially labeled analytes of the sample mixture, it is possible to calculate the absolute amount (often expressed in concentration and/or quantity) of all of the differentially labeled analytes in the sample mixture. In this way, the absolute amount of each differentially labeled analyte (for which there is a calibration standard in the sample from which the analyte originated) can also be determined based upon the knowledge of how the sample mixture was prepared.

Notwithstanding the foregoing, corrections to the intensity of the reporters (signature ions) can be made, as appropriate, for any naturally occurring, or artificially created, isotopic abundance within the reporters. An example of such a correction can be found in Example 3. A more sophisticated example of these types of corrections can also be found in copending and co-owned U.S. Provisional Patent Application Ser. No. 60/524,844, entitled: "Method and Apparatus For De-Convoluting A Convoluted Spectrum", filed on Nov. 26, 2003. The more care taken to accurately quantify the intensity of each reporter, the more accurate will be the relative and absolute quantification of the analytes in the original samples.

Proteomic Analysis:

The methods, mixtures, kits and/or compositions of this invention can be used for complex analysis because samples can be multiplexed, analyzed and reanalyzed in a rapid and repetitive manner using mass analysis techniques. For example, sample mixtures can be analyzed for the amount of individual analytes in one or more samples. The amount (often expressed in concentration and/or quantity) of those analytes can be determined for the samples from which the sample mixture was comprised. Because the sample processing and mass analyses can be performed rapidly, these methods can be repeated numerous times so that the amount of many differentially labeled analytes of the sample mixture can be determined with regard to their relative and/or absolute amounts in the sample from which the analyte originated.

One application where such a rapid multiplex analysis is useful is in the area of proteomic analysis. Proteomics can be viewed as an experimental approach to describe the information encoded in genomic sequences in terms of structure, function and regulation of biological processes. This may be achieved by systematic analysis of the total protein component expressed by a cell or tissue. Mass spectrometry, used in combination with the method, mixture, kit and/or composition embodiments of this invention is one possible tool for such global protein analysis.

For example, with a set of four isobaric labeling reagents, it is possible to obtain four time points in an experiment to determine up or down regulation of protein expression, for example, based upon response of growing cells to a particular stimulant. It is also possible to perform fewer time points but to incorporate one or two controls. In all cases, up or down regulation of the protein expression, optionally with respect to the controls, can be determined in a single multiplex experiment. Moreover, because processing is performed in parallel the results are directly comparable, since there is no risk that slight variations in protocol may have affected the results.

4. DESCRIPTION OF VARIOUS EMBODIMENTS OF THE INVENTION

A. Methods

According to the methods of this invention, the analyte to be determined is labeled. The labeled analyte, the analyte itself, one or more fragments of the analyte and/or fragments of the label, can be determined by mass analysis. In some embodiments, methods of this invention can be used for the analysis of different analytes in the same sample as well as for the multiplex analysis of the same and/or different analytes in two or more different samples. The two or more samples can be mixed to form a sample mixture. In the multiplex analysis, labeling reagents can be used to determine from which sample of a sample mixture an analyte originated. The absolute and/or relative (with respect to the same analyte in different samples) amount (often expressed in concentration or quantity) of the analyte, in each of two or more of the samples combined to form the sample mixture, can be determined. Moreover, the mass analysis of fragments of the analyte (e.g. daughter fragment ions) can be used to identify the analyte and/or the precursor to the analyte; such as where the precursor molecule to the analyte was degraded.

One distinction of the described approach lies in the fact that analytes from different samples can be differentially isotopically labeled (i.e. isotopically coded) with unique labels that are chemically isomeric or isobaric (have equal mass) and that identify the sample from which the analyte originated. The differentially labeled analytes are not distinguished in MS mode of a mass spectrometer because they all have identical (gross) mass to charge ratios. However, when subjected to dissociative energy levels, such as through collision induced dissociation (CID), the labels can fragment to yield unique reporters that can be resolved by mass (mass to charge ratio) in a mass spectrometer. The relative amount of reporter observed in the mass spectrum can correlate with the relative amount of a labeled analyte in the sample mixture and, by implication, the amount of that analyte in a sample from which it originated. Thus, the relative intensities of the reporters (i.e. signature ions) can be used to measure the relative amount of an analyte or analytes in two or more different samples that were combined to form a sample mixture. From the reporter information, absolute amounts (often expressed as concentration and/or quantity) of an analyte or analytes in two or more samples can be derived if calibration standards for the each analyte, for which absolute quantification is desired, are incorporated into the sample mixture.

For example, the analyte might be a peptide that resulted from the degradation of a protein using an enzymatic digestion reaction to process the sample. Protein degradation can be accomplished by treatment of the sample with a proteolytic enzyme (e.g. trypsin, papain, pepsin, ArgC, LysC, V8 protease, AspN, pronase, chymotrypsin or carboxypeptid[e]ase C). By determination of the identity and amount of a peptide in a sample mixture and identifying the sample from which it originated, optionally coupled with the determination of other peptides from that sample, the precursor protein to the degraded peptide can be identified and/or quantified with respect to the sample from which it originated. Because this method allows for the multiplex determination of a protein, or proteins, in more than one sample (i.e. from a sample mixture), it is a multiplex method.

In some embodiments, this invention pertains to a method comprising reacting each of two or more samples, each sample containing one or more reactive analytes, with a different labeling reagent of a set of labeling reagents wherein the different labeling reagents of the set each comprise the formula: RP—X—LK—Y—RG. Consequently, one or more analytes of each sample are labeled with the moiety "RP—X—LK—Y—" by reaction of a nucleophile or electrophile of the analyte with the electrophilic or nucleophilic reactive group (RG), respectively, of the different labeling reagents. The labeling process can produce two or more differentially labeled samples each comprising one or more labeled analytes. The labeling reagents of the set can be isomeric or isobaric. The reporter of each labeling reagent can be identified with, and therefore used to identify, the sample from which each labeled analyte originated.

RG is a reactive group the characteristics of which have been previously described. RP is a reporter moiety the characteristics of which have been previously described. The gross mass of each reporter can be different for each reagent of the set. LK is a linker moiety the characteristics of which have been previously described. The gross mass of the linker can compensate for the difference in gross mass between the reporters for the different labeling reagents such that the aggregate gross mass of the reporter/linker combination is the same for each reagent of the set. X is a bond between an atom of the reporter and an atom of the linker. Y is a bond between an atom of the linker and an atom of the reactive group (or after reaction with an analyte, Y is a bond between the an atom of the linker and an atom of the analyte). Bonds X and Y fragment in at least a portion of the labeled analytes when subjected to dissociative energy levels in a mass spectrometer. The characteristics of bonds X and Y have been previously described.

Once the analytes of each sample are labeled with the labeling reagent that is unique to that sample, the two or more differentially labeled samples, or a portion thereof, can be mixed to produce a sample mixture. Where quantitation is desired, the volume and/or quantity of each sample combined to produce the sample mixture can be recorded. The volume and/or quantity of each sample, relative to the total sample volume and/or quantity of the sample mixture, can be used to determine the ratio necessary for determining the amount (often expressed in concentration and/or quantity) of an identified analyte in each sample from the analysis of the sample mixture. The sample mixture can therefore comprise a complex mixture wherein relative amounts of the same and/or different analytes can be identified and/or quantitated, either by relative quantitation of the amounts of analyte in each of the two or more samples or absolutely where a calibration standard is also added to the sample mixture.

The mixture can then be subjected to spectrometry techniques wherein a first mass analysis can be performed on the sample mixture, or fraction thereof, using a first mass analyzer. Ions of a particular mass to charge ratio from the first mass analysis can then be selected. The selected ions can then be subjected to dissociative energy levels (e.g.

collision-induced dissociation (CID)) to thereby induce fragmentation of the selected ions. By subjecting the selected ions, of a particular mass to charge ratio, of the labeled analytes to dissociative energy levels, both bonds X and Y can be fragmented in at least a portion of the selected ions. Fragmentation of both bonds X and Y can cause fragmentation of the reporter/linker moiety as well as cause release the charged or ionized reporter from the analyte. Ions subjected to dissociative energy levels can also cause fragmentation of the analyte to thereby produce daughter fragment ions of the analyte. The ions (remaining selected ions, daughter fragment ions and charged or ionized reporters), or a fraction thereof, can then be directed to a second mass analyzer.

In the second mass analyzer, a second mass analysis can be performed on the selected ions, and the fragments thereof. The second mass analysis can determine the gross mass (or m/z) and relative amount of each unique reporter that is present at the selected mass to charge ratio as well as the gross mass of the daughter fragment ions of at least one reactive analyte of the sample mixture. For each analyte present at the selected mass to charge ratio, the daughter fragment ions can be used to identify the analyte or analytes present at the selected mass to charge ratio. For example, this analysis can be done as previously described in the section entitled: "Analyte Determination By Computer Assisted Database Analysis".

In some embodiments, certain steps of the process can be repeated one or more times. For example, in some embodiments, ions of a selected mass to charge ratio from the first mass spectrometric analysis, different from any previously selected mass to charge ratio, can be treated to dissociative energy levels to thereby form ionized reporter moieties and ionized daughter fragment ions of at least some of the selected ions, as previously described. A second mass analysis of the selected ions, the ionized reporter moieties and the daughter fragment ions, or a fraction thereof, can be performed. The gross mass and relative amount of each reporter moiety in the second mass analysis and the gross mass of the daughter fragment ions can also be determined. In this way, the information can be made available for identifying and quantifying one or more additional analytes from the first mass analysis.

In some embodiments, the whole process can be repeated one or more times. For example, it may be useful to repeat the process one or more times where the sample mixture has been fractionated (e.g. separated by chromatography or electrophoresis). By repeating the process on each sample, it is possible to analyze eli the entire sample mixture. It is contemplated that in some embodiments, the whole process will be repeated one or more times and within each of these repeats, certain steps will also be repeated one or more times such as described above. In this way, the contents of sample mixture can be interrogated and determined to the fullest possible extent.

Those of ordinary skill in the art of mass spectrometry will appreciate that the first and second mass analysis can be performed in a tandem mass spectrometer. Instruments suitable for performing tandem mass analysis have been previously described herein. Although tandem mass spectrometers are preferred, single-stage mass spectrometers may be used. For example, analyte fragmentation may be induced by cone-voltage fragmentation, followed by mass analysis of the resulting fragments using a single-stage quadrupole or time-of-flight mass spectrometer. In other examples, analytes may be subjected to dissociative energy levels using a laser source and the resulting fragments recorded following post-source decay in time-of-flight or tandem time-of-flight (TOF-TOF) mass spectrometers.

According to the preceding disclosed multiplex methods, in some embodiments, bond X can be more or less prone to, or substantially equal to, fragmentation as compared with fragmentation of bonds of the analyte (e.g. an amide (peptide) bond in a peptide backbone). In some embodiments, bond Y can be more or less prone to fragmentation as compared with fragmentation of bonds of the analyte (e.g. an amide (peptide) bond in a peptide backbone). In some embodiments, the linker for each reagent of the set is neutral in charge after the fragmentation of bonds X and Y (i.e. the linker fragments to produce a neutral loss of mass and is therefore not observed in the MS/MS spectrum). In still some other embodiments, the position of bonds X and Y does not vary within the labeling reagents of a set, within the labeled analytes of a mixture or within the labeling reagents of a kit. In yet some other embodiments, the reporter for each reagent of the set does not substantially sub-fragment under conditions that are used to fragment the analyte (e.g. an amide (peptide) bond of a peptide backbone). In yet some other embodiments, bond X is less prone to fragmentation as compared with bond Y. In still some other embodiments, bond Y is less prone to fragmentation as compared with bond X. In still some other embodiments, bonds X and Y are of approximately the same lability or otherwise are selected such that fragmentation of one of bonds X or Y results in the fragmentation of the other of bonds X or Y. Other characteristics of the groups that for the RP—X—LK—Y— moiety of labeled analytes have previously been described.

In some embodiments, the label of each isobarically labeled analyte can be a 5, 6 or 7 membered heterocyclic ring comprising a ring nitrogen atom that is N-alkylated with a substituted or unsubstituted acetic acid moiety to which the analyte is linked through the carbonyl carbon of the N-alkyl acetic acid moiety, wherein each different label can comprise one or more heavy atom isotopes. The heterocyclic ring can be substituted or unsubstituted. The heterocyclic ring can be aliphatic or aromatic. Possible substituents of the heterocyclic moiety include alkyl, alkoxy and aryl groups. The substituents can comprise protected or unprotected groups, such as amine, hydroxyl or thiol groups, suitable for linking the analyte to a support. The heterocyclic ring can comprise additional heteroatoms such as one or more nitrogen, oxygen or sulfur atoms.

In some embodiments, labeled analytes in the sample mixture can be isobars and each comprise the general formula:

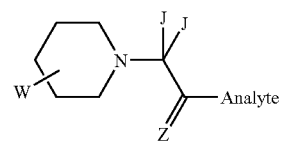

wherein: Z is O, S, NH or NR$^1$; each J is the same or different and is H, deuterium (D), R$^1$, OR$^1$, SR$^1$, NHR$^1$, N(R$^1$)$_2$, fluorine, chlorine, bromine or iodine; W is an atom or group that is located ortho, meta or para to the ring nitrogen and is NH, N—R$^1$, N—R$^2$, P—R$^1$, P—R$^2$, O or S; each carbon of the heterocyclic ring has the formula CJ$_2$; each R$^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms; and R² is an amino alkyl, hydroxy alkyl, thio alkyl group or a cleavable linker that cleavably links the reagent to a solid support wherein the amino alkyl, hydroxy alkyl or thio alkyl group comprises one to eight carbon atoms, which may optionally contain a heteroatom or a substituted or unsubstituted aryl group, and wherein the carbon atoms of the alkyl and aryl groups independently comprise linked hydrogen, deuterium and/or fluorine atoms.

For example, the sample mixture can comprise one or more isobarically labeled analytes of the general formula:

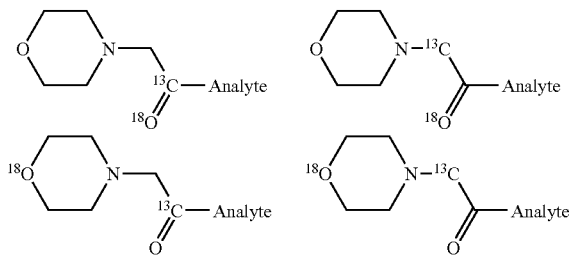

wherein isotopes of carbon 13 and oxygen 18 are used to balance the gross mass between the morpholine reporter and the carbonyl linker of the different labeling reagents.

Morpholine labeling reagents suitable to produce labeled analytes of this general structure can be prepared by numerous synthetic routes. For example, isotopically labeled or non-isotopically labeled morpholine compounds can be reacted with isotopically labeled or non-isotopically labeled bromoacetic acid compounds as described in Example 1. It should likewise be apparent that a ring-substituted morpholine and/or substituted bromoacetic acid starting materials can also be selected and used by one of skill in the art without the exercise of undue experimentation (with little or no change to the above described procedure or other procedures well-known in the art) to thereby produce various different morpholine based labeling reagents, of differing heavy atom isotope content (i.e. isotopically coded), that can be used in the sets or kits of this invention.

Instead of morpholine, it is possible to choose a substituted or unsubstituted piperidine of desired isotopic distribution. When piperidine is chosen, the isotopes D (deuterium) $^{13}C$ or $^{15}N$ can be substituted for H, $^{12}C$ and $^{14}N$, respectively, and used to alter the gross mass of the reagents of a set of labeling reagents in a manner similar to that illustrated for morpholine except that in the case of piperidine, $^{18}O$ is not used in the ring atoms. An exemplary synthesis of a piperidine, optionally using isotopically enriched starting materials, is described in Example 6.

The sample mixture can comprise one or more isobarically labeled analytes of the formula:

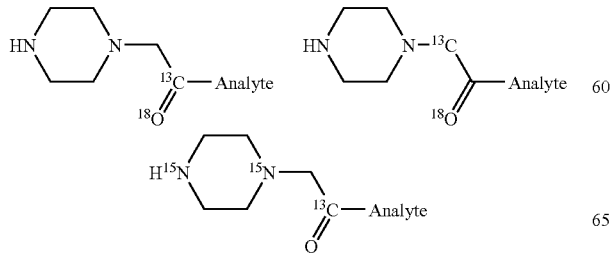

-continued

Figure 9A:
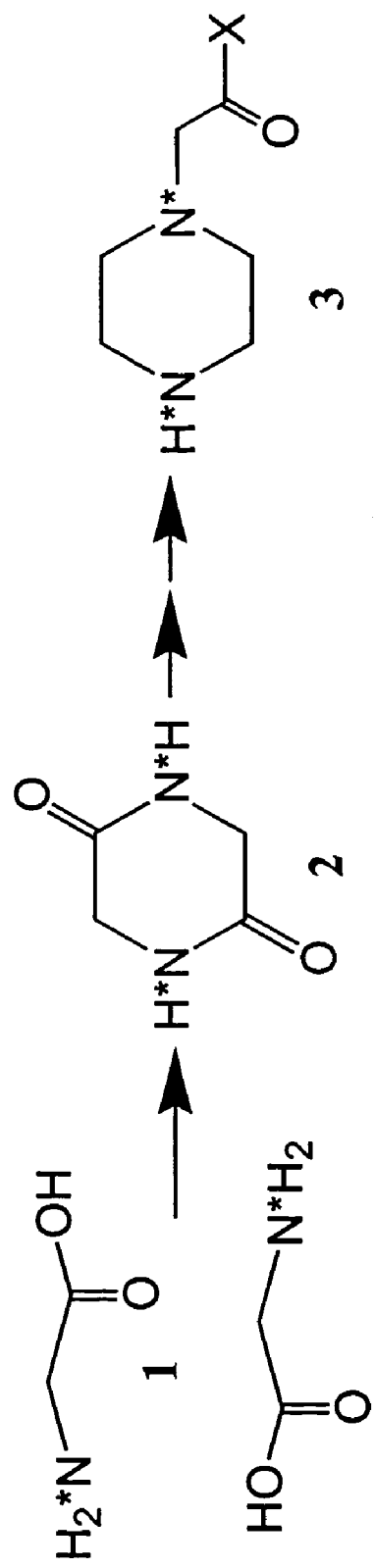
FIGS. 9A and 9B are an illustration of synthetic routes to isotopically labeled piperazine labeling reagents from basic starting materials. The route can also be used to prepare non-isotopically labeled piperazine reagents wherein non-isotopically labeled starting materials are used.
Figure 9B:
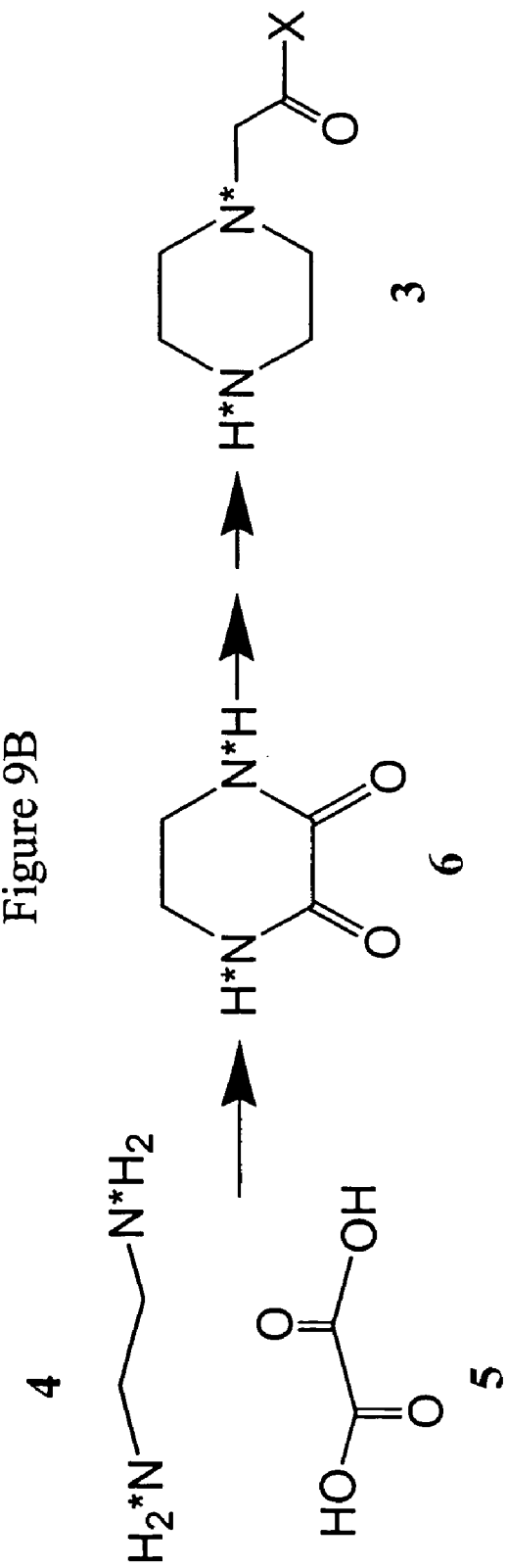

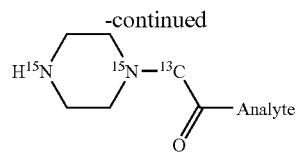

wherein isotopes of carbon 13, oxygen 18 and nitrogen 15 are used to balance the gross mass between the reporter and the carbonyl linker of the different labeling reagents. Piperazine labeling reagents suitable to produce labeled analytes of this general structure can be prepared by numerous synthetic routes. For example, heavy or light piperazine compounds can be reacted with heavy or light labeled bromoacetic acid compounds as described in Example 7. With reference to FIGS. 9A and 9B, a general schematic is shown for two different synthetic routes to isotopically enriched piperazines using readily available heavy or light starting materials.

Specifically with reference to FIG. 9A, two equivalents of $^{15}N$-labeled glycine 1 can be condensed to form the bis-isotopically labeled di-ketopiperazine 2 (the isotopic label is represented by the * in the Figure). The di-ketopiperazine can then be reduced to an isotopically labeled piperazine. The isotopically labeled piperazine can then be reacted with bromoacetic acid and converted to an active ester 3 as described in Example 7.

Specifically with reference to FIG. 9B, bis-$^{15}N$-labeled ethylenediamine 4 can be condensed with oxalic acid 5 to for the bis-isotopically labeled di-ketopiperazine 6 (the isotopic label is represented by the * in the Figure). The di-ketopiperazine can then be reduced to an isotopically labeled piperazine. The isotopically labeled piperazine can then be reacted with bromoacetic acid and converted to an active ester 3 as described in Example 7.

It should likewise be apparent that a ring-substituted piperazine can be made using the above-described methods by merely choosing appropriately substituted starting materials. Where appropriate, a substituted bromoacetic acid (either heavy or light) can likewise be used. By heavy we mean that the compound is isotopically enriched with one or more heave atom isotopes). By light we mean that it is not isotopically enriched. Accordingly, appropriately substituted starting materials can be selected to thereby produce various different piperazine based labeling reagents that can be used in the sets of this invention.

For example, the sample mixture can comprise one or more isobarically labeled analytes of the formula:

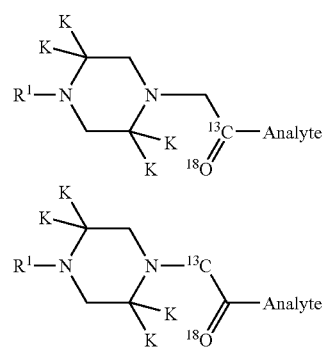

-continued

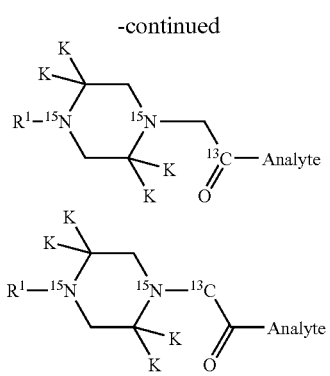

wherein: isotopes of carbon 13, oxygen 18 and nitrogen 15 are used to balance the gross mass between the reporter and the carbonyl linker of the different labeling reagents and wherein; 1) each $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms; and 2) each K is independently selected as hydrogen or an amino acid side chain. Substituted piperazine labeling reagents suitable to produce labeled analytes of this general structure can be prepared by numerous synthetic routes.

Figure 10:
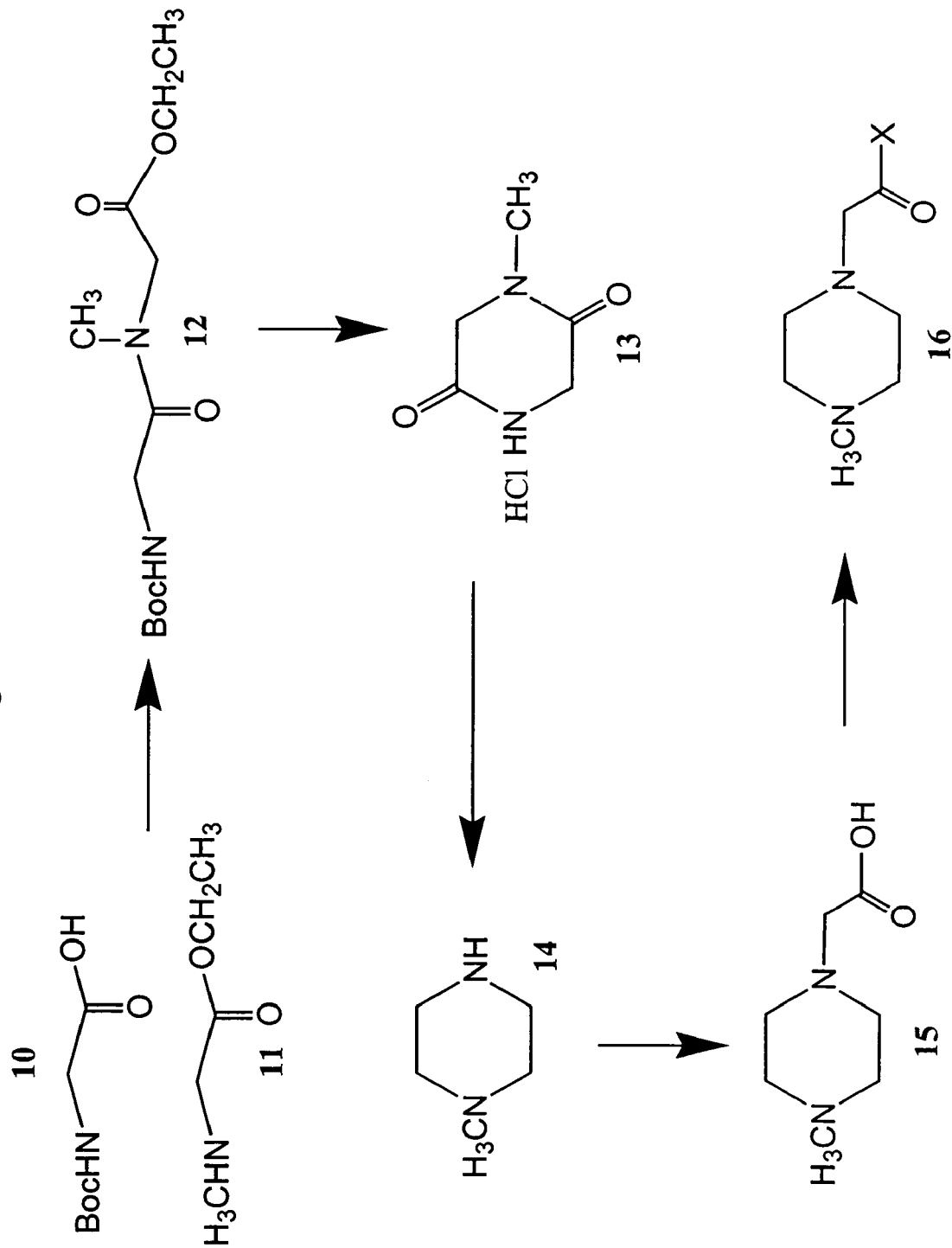
FIG. 10 is an illustration of a synthetic route to isotopically labeled and non-isotopically labeled N-alkyl piperazine labeling reagents from basic starting materials.

For example, with reference to FIG. 10, N-alkyl substituted piperazine reagents can be prepared in accordance with the illustrated procedure. The tert-butyloxycarbonyl (t-boc) protected glycine 10 can be condensed with the ester (e.g. ethyl ester) of N-methyl-glycine 11 to thereby form the ester of the t-boc protected glycine-N-methyl-glycine dimer 12. The gly-gly dimer 12 can then be cyclized by removal of the t-boc protecting group followed by condensation to thereby form the acid salt of the N-methyl-di-ketopiperazine 13. The acid salt of 13 can be neutralized and reduced to form the N-methyl-piperazine 14. The N-methyl-piperazine 14, can then be reacted with bromoacetic acid 15 (or substituted versions thereof and converted to an active ester 16 as described in Example 7.

It should be apparent that a ring-substituted piperazine can be made using the above-described method by merely choosing an amino acid or N-methyl amino acid (or ester thereof other than glycine (e.g. alanine, phenylalanine, leucine, isoleucine, valine, asparagine, apartic acid, etc). It should likewise be apparent that the amino acids can be isotopically labeled in a manner suitable for preparing ring substituted piperazines having the desired distribution of isotopes necessary to prepare sets of isobaric labeling reagents.

Figure 11:
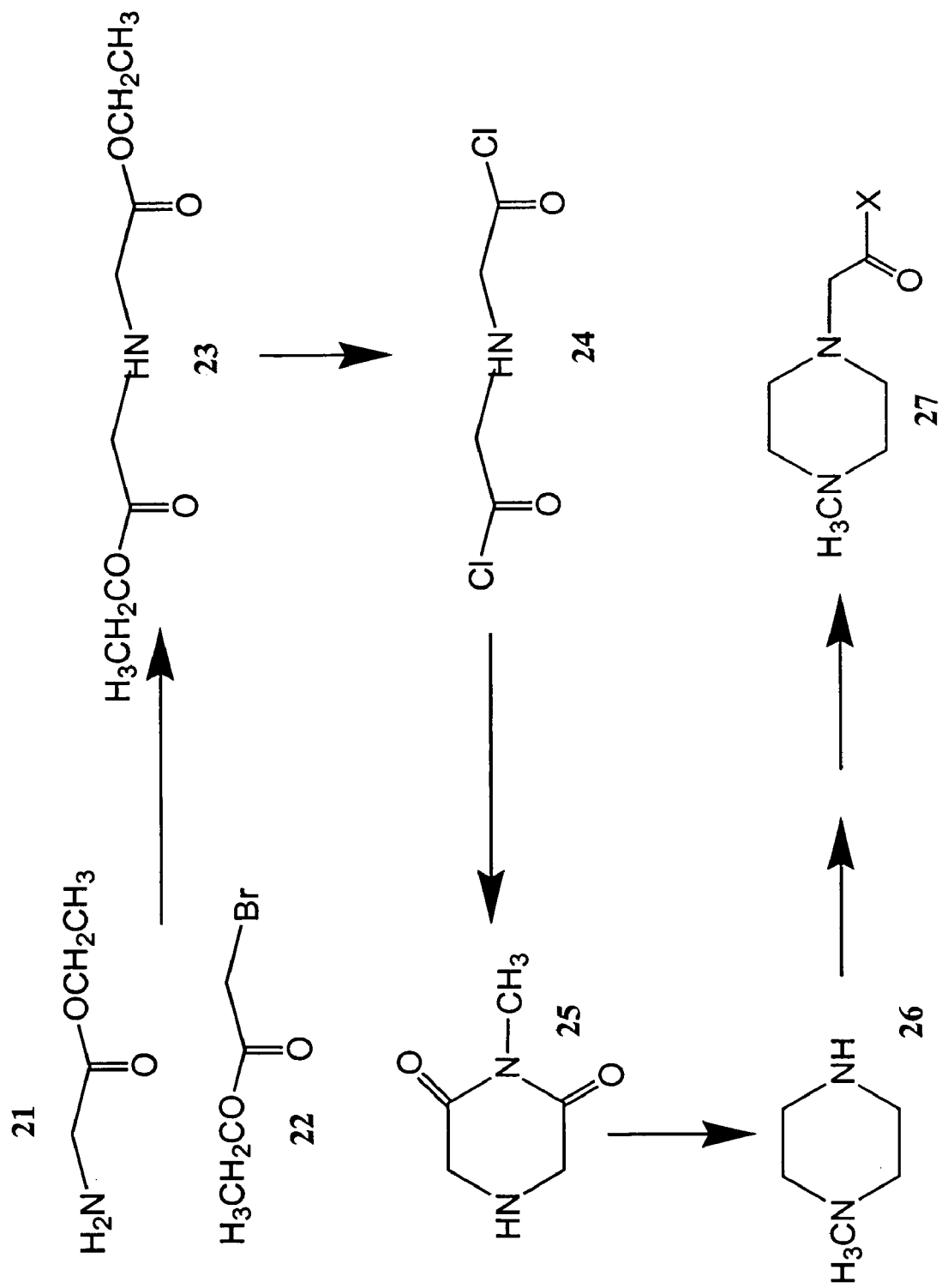
FIG. 11 is an illustration of a synthetic route to isotopically labeled and non-isotopically labeled N-alkyl piperazine labeling reagents from basic starting materials.
Figure 12:
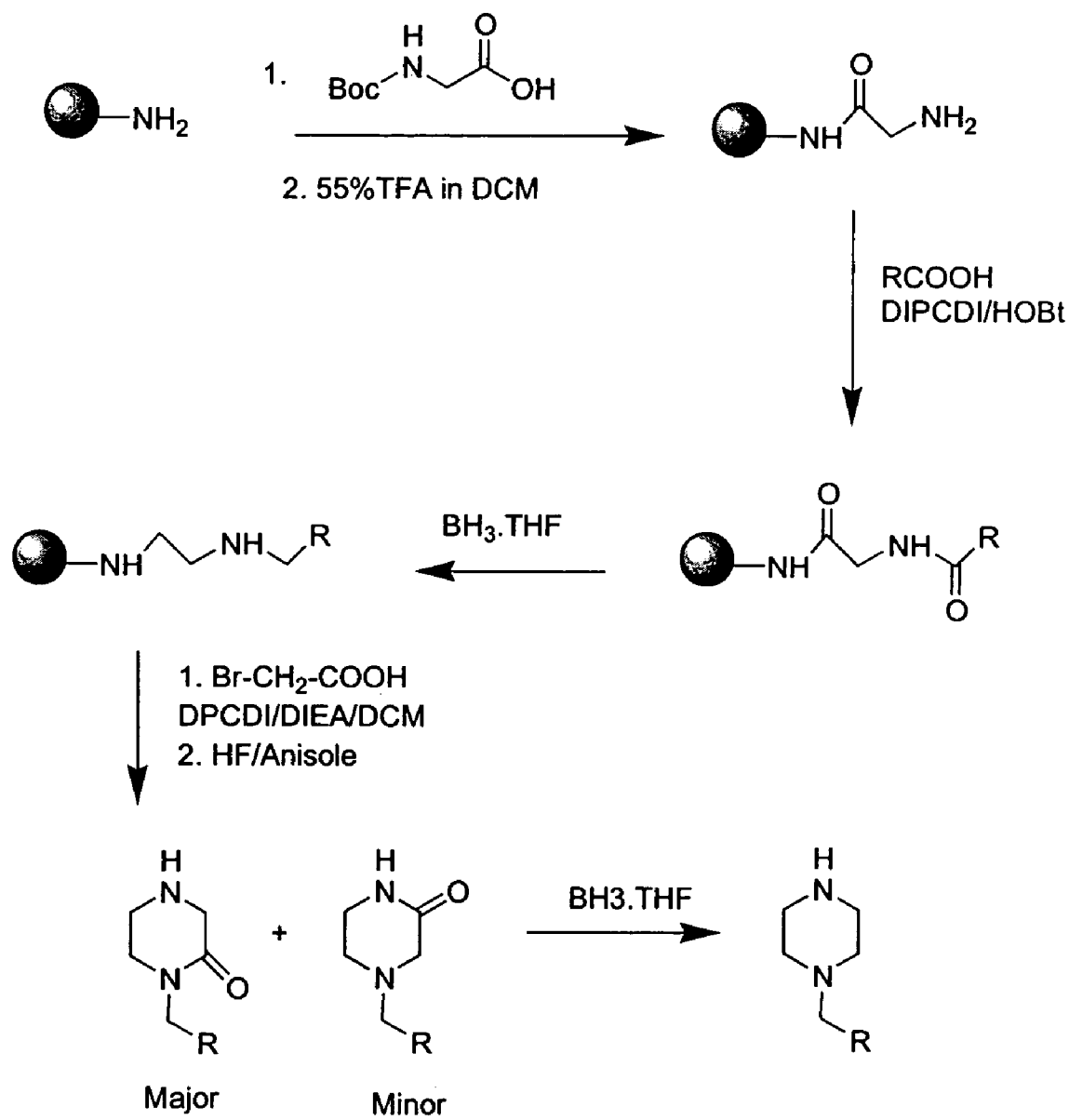
FIG. 12 is an illustration of a solid phase based synthetic route to isotopically labeled and non-isotopically labeled piperazine labeling reagents from basic starting materials.

N-alkyl substituted piperazine reagents can be prepared in accordance by still another illustrated procedure. With reference to FIG. 11, glycine methyl ester 21 can be reacted with the ethyl ester of bromoacetic acid 22 to form the diethyl iminodiacetate 23. The diester of the diethyl iminodiacetate 23 can be converted to a di-acid chloride 24 by treatment an appropriate reagent (e.g. thionyl chloride). The di-acid chloride 24 can then be reacted with, for example, an alkyl amine (e.g. methyl amine) to form an N-alkyl-di-ketopiperazine 25. The N-alkyl-di-ketopiperazine 25 can then be reduced to form the N-alkyl-piperazine 26. The N-alkyl-piperazine can then be reacted with bromoacetic acid and converted to an active ester 27 as described in Example 7.

It should be apparent that a ring-substituted piperazine can be made using the above-described method by merely choosing an ester of an amino acid other than glycine (e.g. alanine, phenylalanine, leucine, isoleucine, valine, asparagine, apartic acid, etc) or a substituted version of bromoacetic acid. It should likewise be apparent that the amino acids and bromoacetic acid (and its substituted derivatives) can be isotopically labeled in a manner suitable for preparing ring substituted piperazines having the desired distribution of isotopes necessary to prepare sets of isobaric labeling reagents. It should be further apparent that choosing an alkyl diamine, hydroxyalkyl amine or thioalkylamine, or isotopically labeled version thereof, instead of an alkyl amine can be used to produce the support bound labeling reagents as described in more detail below.

In yet some other embodiments of the method, labeled analytes in the sample mixture are isobars and each comprise the formula:

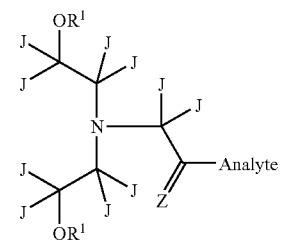

wherein: Z is O, S, NH or $NR^1$; each J is the same or different and is selected from the group consisting of: H, deuterium (D), $R^1$, $OR^1$, $SR^1$, $NHR^1$, $N(R^1)_2$, fluorine, chlorine, bromine and iodine; each $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms.

For example, the sample mixture can comprise two or more isobarically labeled analytes of the formula:

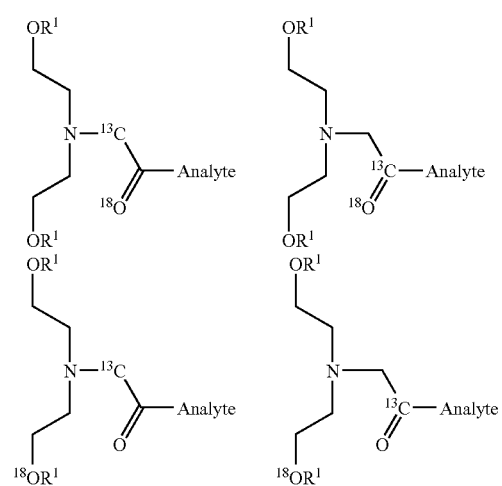

wherein isotopes of carbon 13 and oxygen 18 are used to balance the gross mass between the reporter and the carbonyl linker of the different labeling reagents. Substituted labeling reagents suitable to produce labeled analytes of this general structure can be prepared by the general process described in Example 8.

In still some other embodiments of this invention, each different labeling reagent of a set or kit of labeling reagents can be linked to a support through a cleavable linker such that each different sample can be reacted with a support carrying a different labeling reagent. In some embodiments, the supports can themselves be used for the labeling of reactive analytes. In some embodiments, the labeling reagents can be removed from the supports and then used, in some cases after subsequent processing (e.g. protection of reactive groups), for the labeling of reactive analytes.

According to some embodiments, the analytes from a sample can be reacted with the solid support (each sample being reacted with a different solid support and therefore a different reporter) and the resin bound components of the sample that do not react with the reactive group can be optionally washed away. The labeled analyte or analytes can then be removed from each solid support by treating the support under conditions that cleave the cleavable linker and thereby release the reporter/linker/analyte complex from the support. Each support can be similarly treated under conditions that cleave the cleavable linker to thereby obtain two or more different samples, each sample comprising one or more labeled analytes wherein the labeled analytes associated with a particular sample can be identified and/or quantified by the unique reporter linked thereto. The collected samples can then be mixed to form a sample mixture, as previously described.

For example, each different labeling reagent of the set used in the previously described method can be a solid support of the formula: E—F—RP—X—LK—Y—RG, wherein; RG, X, Y, RP and LK have been described previously. E is a solid support and F is a cleavable linker linked to the solid support and cleavably linked to the reporter. Supports of this general formula can be prepared as described in Example 9.

In some embodiments, a set of support bound labeling reagents can be based on labeled N-(aminoalkyl), N-(thioalkyl) or N-(hydroxyalkyl)-piperazine derivatives. Both heavy and light piperazine derivatives can be prepared. The labeled N-(aminoalkyl), N-(thioalkyl) or N-(hydroxyalkyl)-piperazine derivatives can be formed, for example, by using the procedure illustrated in FIG. 11 starting with an alkyl diamine, thioalkyl amine or hydroxyalkyl amine as the N-alkyl amine (see the discussion of FIG. 11, above). The alkyl diamine, thioalkyl amine or hydroxyalkyl amine can be heavy or light where appropriate for synthesis of a desired N-(aminoalkyl), N-(thioalkyl) or N-(hydroxyalkyl)-piperazine derivative. The amino, hydroxyl or thiol group of the N-(aminoalkyl), N-(thioalkyl) or N-(hydroxyalkyl)-piperazine derivatives can be protected as appropriate. When an alkyl diamine, thioalkylamine or hydroxyalkyl amine is used, the piperazine can comprise an N-aminoalkyl, N-thioalkyl or N-hydroxyalkyl moiety wherein the amino, hydroxyl or thiol group of the moiety can be reacted with the cleavable linker on a support to thereby cleavably link the piperazine, prepared from the N-(aminoalkyl), N-(thioalkyl) or N-(hydroxyalkyl)-piperazine derivative, to the support.

The support comprising a labeling reagent can be prepared by any of several methods. In some embodiments, the amino, hydroxyl or thiol group of the N-(aminoalkyl), N-(thioalkyl) or N-(hydroxyalkyl)-piperazine can be reacted with the cleavable linker of a suitable support. The cleavable linker can be a "sterically hindered cleavable linker" (See: Example 9). The piperazine can be reacted with isotopically labeled or non-isotopically labeled haloacetic acid (substituted or unsubstituted) depending on the nature of the labeling reagent desired for the set of labeling reagents. Thereafter the carboxylic acid can be converted to an active ester. The active ester can be reacted with analytes of a sample to thereby label the analytes with the labeling reagent of the support. Cleavage of the cleavable linker will release the labeled analyte from the support. This process can be repeated with an unique piperazine based labeling reagent for the preparation of the different supports of a set of labeling supports.

In some embodiments, the N-(aminoalkyl), N-(thioalkyl) or N-(hydroxyalkyl)-piperazine can be first reacted with isotopically labeled or non-isotopically labeled haloacefic acid (substituted or unsubstituted), or an ester thereof. Preferably, the amino, hydroxyl or thiol group of the N-(aminoalkyl), N-(thioalkyl) or N-(hydroxyalkyl)-piperazine can be protected with a suitable protecting reagent (For a list of suitable protecting groups See: Green et al., Protecting Groups In Organic Synthesis, Third Edition, John Wiley & Sons, Inc. New York, 1999). The unprotected amino, thiol or hydroxyl group of the resulting bis-alkylated piperazine can then be reacted with the cleavable linker of a suitable support. Thereafter the carboxylic acid can be converted to an active ester. If the haloacetic acid compound was an ester, the ester can be saponified prior to conversion to an active ester. The active ester can be reacted with analytes of a sample to thereby label the analytes with the labeling reagent of the support. Cleavage of the cleavable linker will release the labeled analyte from the support. This process can be repeated with a unique piperazine based labeling reagent for the preparation of the different supports of a set of labeling supports.

Therefore, in some embodiments, the set of labeling reagents can comprise one or more of the following support bound labeling reagents:

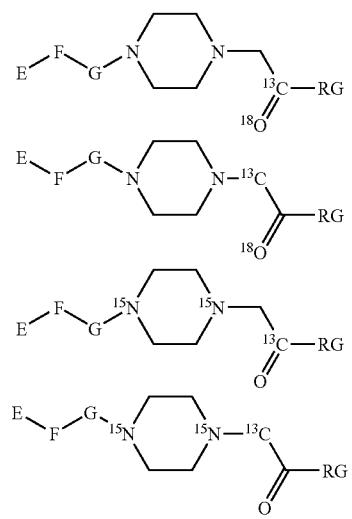

wherein RG, E and F have been previously described. According to the method, G can be an amino alkyl, hydroxy alkyl or thio alkyl group, cleavably linked to the cleavable linker wherein the amino alkyl, hydroxy alkyl or thio alkyl group comprises one to eight carbon atoms, which may optionally contain a heteroatom or a substituted or unsubstituted aryl group, and wherein the carbon atoms of the alkyl and aryl groups independently comprise linked hydrogen, deuterium and/or fluorine atoms. Each carbon of the heterocyclic ring can have the formula $CJ_2$, wherein each J is the same or different and is selected from the group consisting of H, deuterium (D), $R^1$, $OR^1$, $SR^1$, $NHR^1$, $N(R^1)_2$, fluorine, chlorine, bromine and iodine. Each $R^1$ can be the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms.

In some embodiments, the labeled analytes can be generated by first reacting the analyte with a support comprising the labeling reagent, cleavably linked to the support through a cleavable linker, and then cleaving the labeled analyte from the support. Accordingly, a sample mixture can comprise one or more isobarically labeled analytes of the formula:

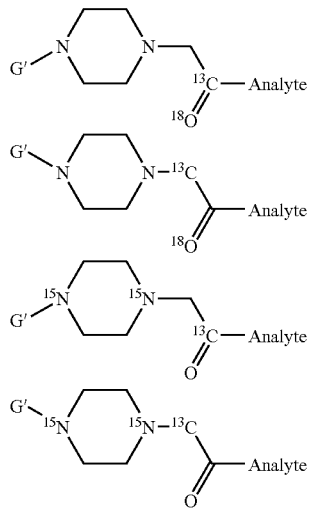

wherein: G' can be an amino alkyl, hydroxy alkyl or thio alkyl group comprising one to eight carbon atoms which may optionally contain a heteroatom or a substituted or unsubstituted aryl group wherein the carbon atoms of the alkyl and aryl groups independently comprise linked hydrogen and/or deuterium atoms. Each carbon of the heterocyclic ring can have the formula $CJ_2$, wherein each J is the same or different and is selected from the group consisting of: H, deuterium (D), $R^1$, $OR^1$, $SR^1$, $NHR^1$, $N(R^1)_2$, fluorine, chlorine, bromine and iodine. Each $R^1$ can be the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms. Here the alkyl amine group, hydroxy alkyl group or thio alkyl group can be the moiety that was linked to the cleavable linker of the solid support. The product of each cleavage reaction can be combined to produce a sample mixture suitable for analysis of labeled analytes by the methods described herein.

In some embodiments, methods of the invention can further comprise digesting each sample with at least one enzyme to partially, or fully, degrade components of the sample prior to performing the labeling of the analytes of the sample (Also see the above section entitled: "Sample Processing"). For example, the enzyme can be a protease (to degrade proteins and peptides) or a nuclease (to degrade nucleic acids). The enzymes may also be used together to thereby degrade sample components. The enzyme can be a proteolytic enzyme such as trypsin, papain, pepsin, ArgC, LysC, V8 protease, AspN, pronase, chymotrypsin or carboxypeptid[e]ase C.

In some embodiments, methods can further comprise separating the sample mixture prior to performing the first mass analysis (Also see the above section entitled: "Separation Of The Sample Mixture"). In this manner the first mass analysis can be performed on only a fraction of the sample mixture. The separation can be performed by any separations method, including by chromatography or by electrophoresis. For example, liquid chromatography/mass spectrometry (LC/MS) can be used to effect such a sample separation and mass analysis. Moreover, any chromatographic separation process suitable to separate the analytes of interest can be used. Non-limiting examples of suitable chromatographic and electrophoretic separations processes have been described herein.

In still other embodiments, the methods of the invention can comprise both an enzyme treatment to degrade sample components and a separations step.

As described previously, it is possible to determine the analyte associated with the selected ions by analysis of the gross mass of the daughter fragment ions. One such method of determination is described in the section entitled: "Analyte Determination By Computer Assisted Database Analysis".

Once the analyte has been determined, information regarding the gross mass and relative amount of each reporter moiety in the second mass analysis and the gross mass of daughter fragment ions provides the basis to determine other information about the sample mixture. The amount of reporter can be determined by peak intensity in the mass spectrum. In some embodiments, the amount of reporter can be determined by analysis of the peak height or peak width of the reporter (signature ion) signal obtained using the mass spectrometer. Because each sample can be labeled with a different labeling reagent and each labeling reagent can comprise a unique reporter that can be correlated with a particular sample, determination of the different reporters in the second mass analysis identifies the sample from which the ions of the selected analyte originated. Where multiple reporters are found (e.g. according to the multiplex methods of the invention), the relative amount of each reporter can be determined with respect to the other reporters. Because the relative amount of each reporter determined in the second mass analysis correlates with the relative amount of an analyte in the sample mixture, the relative amount (often expressed as concentration and/or quantity) of the analyte in each sample combined to form the sample mixture can be determined. As appropriate, a correction of peak intensity associated with the reporters can be performed for naturally occurring, or artificially created, isotopic abundance, as previously discussed. More specifically, where the volume and/or quantity of each sample that is combined to the sample mixture is known, the relative amount (often expressed as concentration and/or quantity) of the analyte in each sample can be calculated based upon the relative amount of each reporter determined in the second mass analysis.

This analysis can be repeated one or more times on selected ions of a different mass to charge ratio to thereby obtain the relative amount of one or more additional analytes in each sample combined to form the sample mixture. As appropriate, a correction of peak intensity associated with the reporters can be performed for naturally occurring, or artificially created, isotopic abundance.

Alternatively, where a calibration standard comprising a unique reporter linked to an analyte, having the selected mass to charge ratio, has been added to the sample mixture in a known amount (often expressed as a concentration and/or quantity), the amount of the unique reporter associated with the calibration standard can be used to determine the absolute amount (often expressed as a concentration and/or quantity) of the analyte in each of the samples combined to form the sample mixture. This is possible because the amount of analyte associated with the reporter for the calibration standard is known and the relative amounts of all other reporters can be determined for the labeled analyte associated with the selected ions. Since the relative amount of reporter, determined for each of the unique reporters (including the reporter for the calibration standard), is proportional to the amount of the analyte associated with each sample combined to form the sample mixture, the absolute amount (often expressed as a concentration and/or quantity) of the analyte in each of the samples can be determined based upon a ratio calculated with respect to the formulation used to produce the sample mixture. As appropriate, a correction of peak intensity associated with the reporters can be performed for naturally occurring, or artificially created, isotopic abundance.

This analysis can be repeated one or more times on selected ions of a different mass to charge ratio to thereby obtain the absolute amount of one or more additional analytes in each sample combined to form the sample mixture. As appropriate, a correction of peak intensity associated with the reporters can be performed for naturally occurring, or artificially created, isotopic abundance.

In some embodiments, the methods can be practiced with digestion and/or separation steps. In some embodiments, the steps of the methods, with or without the digestion and/or separation steps, can be repeated one or more times to thereby identify and/or quantify one or more other analytes in a sample or one or more analytes in each of the two or more samples (including samples labeled with support bound labeling reagents). Depending of whether or not a calibration standard is present in the sample mixture for a particular analyte, the quantitation can be relative to the other labeled analytes, or it can be absolute. Such an analysis method can be particularly useful for proteomic analysis of multiplex samples of a complex nature, especially where a preliminary separation of the labeled analytes (e.g. liquid chromatography or electrophoretic separation) precedes the first mass analysis.

In some embodiments, the analytes can be peptides in a sample or sample mixture. Analysis of the peptides in a sample, or sample mixture, can be used to determine the amount (often expressed as a concentration and/or quantity) of identifiable proteins in the sample or sample mixture wherein proteins in one or more samples can be degraded prior to the first mass analysis. Moreover, the information from different samples can be compared for the purpose of making determinations, such as for the comparison of the effect on the amount of the protein in cells that are incubated with differing concentrations of a substance that may affect cell growth. Other, non-limiting examples may include comparison of the expressed protein components of diseased and healthy tissue or cell cultures. This may encompass comparison of expressed protein levels in cells, tissues or biological fluids following infection with an infective agent such as a bacteria or virus or other disease states such as cancer. In other examples, changes in protein concentration over time (time-course) studies may be undertaken to examine the effect of drug treatment on the expressed protein component of cells or tissues. In still other examples, the information from different samples taken over time may be used to detect and monitor the concentration of specific proteins in tissues, organs or biological fluids as a result of disease (e.g. cancer) or infection.

In some embodiments, the analyte can be a nucleic acid fragment in a sample or sample mixture. The information on the nucleic acid fragments can be used to determine the amount (often expressed as a concentration and/or quantity) of identifiable nucleic acid molecules in the sample or sample mixture wherein the sample was degraded prior to the first mass analysis. Moreover, the information from the different samples can be compared for the purpose of making determinations as described above.

B. Mixtures

In some embodiments, this invention pertains to mixtures (i.e. sample mixtures). The mixtures can comprise at least two differentially labeled analytes, wherein each of the two-labeled analytes can originate from a different sample and comprise the formula: RP—X—LK—Y-Analyte. For each different label, some of the labeled analytes of the mixture can be the same and some of the labeled analytes can be different. The atoms, moieties or bonds, X, Y, RP and LK have been previously described and their characteristics disclosed. The mixture can be formed by mixing all, or a part, of the product of two or more labeling reactions wherein each labeling reaction uses a different labeling reagent of the general formula: RP—X—LK—Y—RG, wherein atoms, moieties or bonds X, Y, RP, LK RG have been previously described and their characteristics disclosed. The labeling reagents can be isotopically coded isomeric or isobaric labeling reagents. The unique reporter of each different labeling reagent can indicate from which labeling reaction each of the two or more labeled analytes is derived. The labeling reagents can be isomeric or isobaric. Hence, two or more of the labeled analytes of a mixture can be isomeric or isobaric. The mixture can be the sample mixture as disclosed in any of the above-described methods. Characteristics of the labeling reagents and labeled analytes associated with those methods have been previously discussed.

The analytes of the mixture can be peptides. The analytes of the mixture can be proteins. The analytes of the mixture can be peptides and proteins. The analytes of the mixture can be nucleic acid molecules. The analytes of the mixture can be carbohydrates. The analytes of the mixture can be lipids. The analytes of the mixture can be steroids. The analytes of the mixture can be small molecules of less than 1500 daltons. The analytes of the mixture comprise two or more analyte types. The analyte types can, for example, be selected from peptides, proteins, nucleic acids carbohydrates, lipids, steroids and/or small molecules of less than 1500 daltons.

In some embodiments, the label of each isobarically labeled analyte can be a 5, 6 or 7 membered heterocyclic ring comprising a ring nitrogen atom that is N-alkylated with a substituted or unsubstituted acetic acid moiety to which the analyte is linked through the carbonyl carbon of the N-alkyl acetic acid moiety, wherein each different label comprises one or more heavy atom isotopes. The heterocyclic ring can be substituted or unsubstituted. The heterocyclic ring can be aliphatic or aromatic. Possible substituents of the heterocylic moiety include alkyl, alkoxy and aryl groups. The substituents can comprise protected or unprotected groups, such as amine, hydroxyl or thiol groups, suitable for linking the analyte to a support. The heterocyclic ring can comprise additional heteroatoms such as one or more nitrogen, oxygen or sulfur atoms.

In some embodiments, the labeled analytes of the mixture are isobars and each comprise the formula:

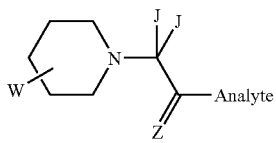

wherein Z, J and W have been previously described and their characteristics disclosed. For example, the sample mixture can comprise one or more isobarically labeled analytes of the formula:

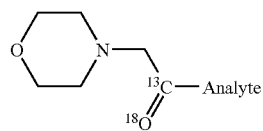 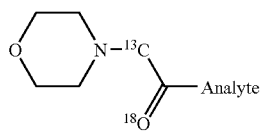

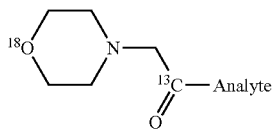 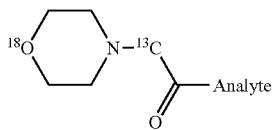

wherein isotopes of carbon 13 and oxygen 18 are used to balance the gross mass between the morpholine reporter and the carbonyl linker of the different labeling reagents.

In some embodiments, the sample mixture can comprise one or more isobarically labeled analytes of the formula:

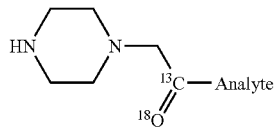 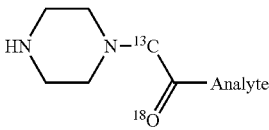

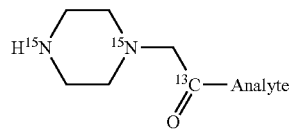

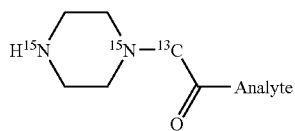

wherein isotopes of carbon 13, oxygen 18 and nitrogen 15 are used to balance the gross mass between the reporter and the carbonyl linker of the different labeling reagents. In some embodiments, the sample mixture can comprise one or more isobarically labeled analytes of the formula:

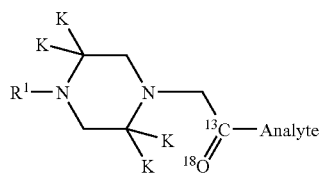

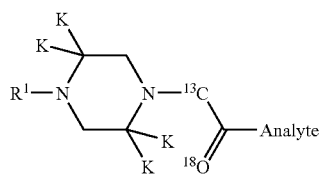

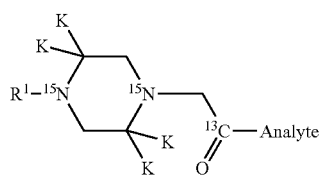

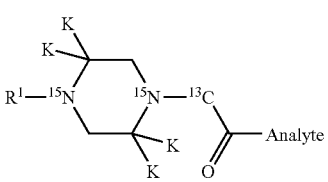

wherein: isotopes of carbon 13, oxygen 18 and nitrogen 15 are used to balance the gross mass between the reporter and the carbonyl linker of the different labeling reagents and wherein; 1) each $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms; and 2) each K is independently selected as hydrogen or an amino acid side chain.

In some embodiments, the labeled analytes of the mixture are isobars and each comprise the formula:

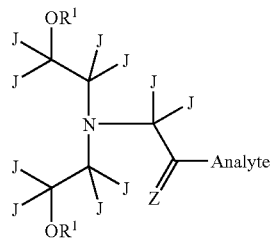

wherein: Z, J and $R^1$ have been previously described and their characteristics disclosed. For example, the sample mixture can comprise one or more isobarically labeled analytes of the formula:

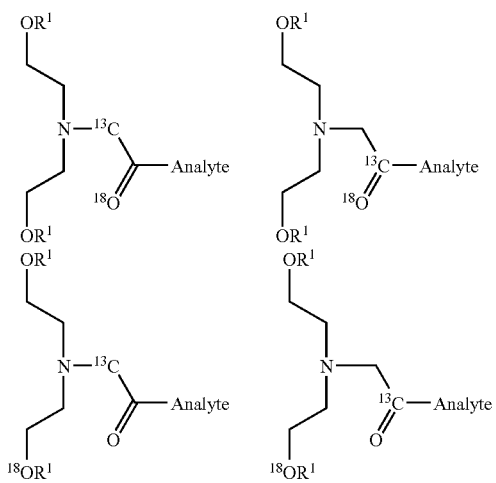

wherein isotopes of carbon 13 and oxygen 18 are used to balance the gross mass between the reporter and the carbonyl linker of the different labeling reagents.

In other embodiments, the labeled analytes can be generated by first reacting the analyte with a support comprising the labeling reagent, cleavably linked to the support through a cleavable linker, and then cleaving the labeled analyte from the support. For example the labeled analytes of the mixture can be one or more isobars comprising the general formula:

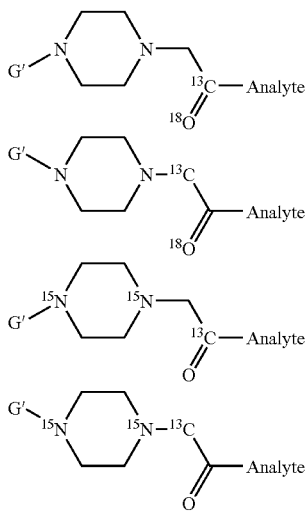

wherein: G' has been previously described and its characteristics disclosed.

C. Kits

In some embodiments, this invention pertains to kits. The kits can comprise a set of two or more labeling reagents of the formula: RP—X—LK—Y—RG and one or more reagents, containers, enzymes, buffers and/or instructions. The atoms, moieties or bonds X, Y, RP, LK RG have been previously described and their characteristics disclosed. The labeling reagents of a kit can be isomeric or isobaric. Other properties of the labeling reagents of the kits have likewise been disclosed. For example, the kits can be useful for the multiplex analysis of one or more analytes in the same sample, or in two or more different samples.

In some embodiments, the label of each isobarically labeled analyte can be a 5, 6 or 7 membered heterocyclic ring comprising a ring nitrogen atom that is N-alkylated with a substituted or unsubstituted acetic acid moiety to which the analyte is linked through the carbonyl carbon of the N-alkyl acetic acid moiety, wherein each different label comprises one or more heavy atom isotopes. The heterocyclic ring can be substituted or unsubstituted. The heterocyclic ring can be aliphatic or aromatic. Possible substituents of the heterocyclic moiety include alkyl, alkoxy and aryl groups. The substituents can comprise protected or unprotected groups, such as amine, hydroxyl or thiol groups, suitable for linking the analyte to a support. The heterocyclic ring can comprise additional heteroatoms such as one or more nitrogen, oxygen or sulfur atoms.

In some embodiments, the different reagents of a kit are isobars and each comprise the formula:

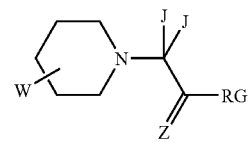

wherein RG, Z, J and W have been previously described and their characteristics disclosed. For example, the reagents of a kit can comprise one or more isobarically labeled reagents of the formula:

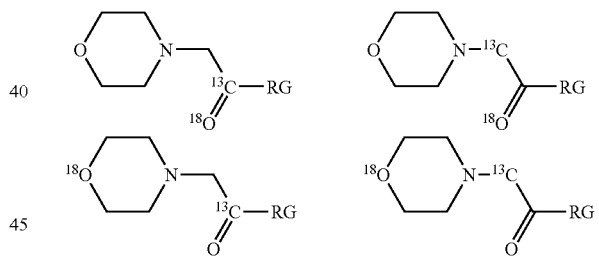

wherein RG is the reactive group and isotopes of carbon 13 and oxygen 18 are used to balance the gross mass between the morpholine reporter and the carbonyl linker of the different labeling reagents.

In some embodiments, the kit can comprise one or more isobarically labeled reagents of the formula:

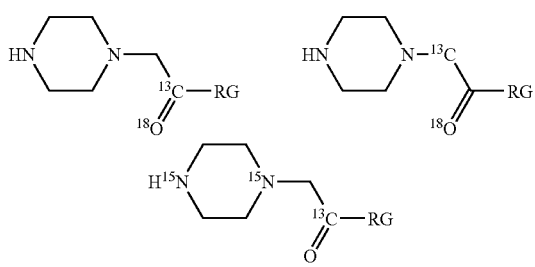

-continued

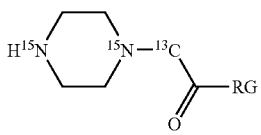

wherein RG is the reactive group and isotopes of carbon 13, oxygen 18 and nitrogen 15 are used to balance the gross mass between the reporter and the carbonyl linker of the different labeling reagents. In some embodiments, the reagents of a kit can comprise one or more isobarically labeled reagents of the formula:

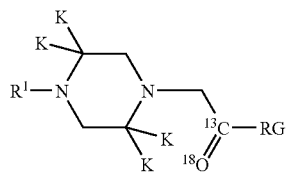

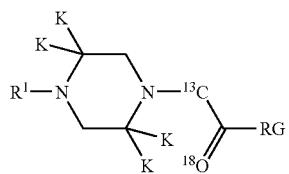

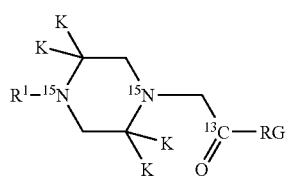

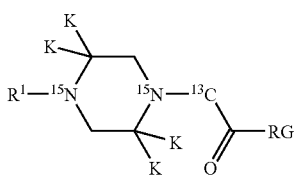

wherein: isotopes of carbon 13, oxygen 18 and nitrogen 15 are used to balance the gross mass between the reporter and the carbonyl linker of the different labeling reagents and wherein; 1) each $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms; and 2) each K is independently selected as hydrogen or an amino acid side chain. In yet other embodiments, the labeled analytes of the kit are isobars and each comprises the formula:

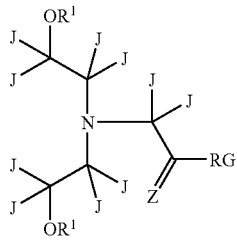

wherein: RG Z, J and $R^1$ have been previously described and their characteristics disclosed. For example, the reagents of a kit can comprise one or more isobarically labeled analytes of the formula:

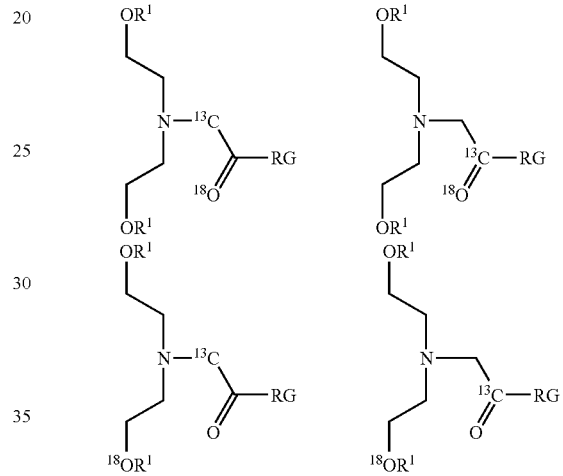

wherein RG has been previously described and disclosed and isotopes of carbon 13 and oxygen 18 are used to balance the gross mass between the reporter and the carbonyl linker of the different labeling reagents.

In some embodiments, this invention pertains to kits comprising one or more sets of supports, each support comprising a different labeling reagent, cleavably linked to the support through a cleavable linker. For example, the cleavable linker can be chemically or photolytically cleavable. The supports can be reacted with different samples thereby labeling the analytes of a sample with the same reporter/linker, and analytes of different samples with different reporter/linker combinations. Supports of a set that can be used in embodiments of this invention have the general formula: E—F—G—RP—X—LK—Y—RG, wherein E, F, G, RP, X, LK, Y and RG have been previously defined herein and their characteristics disclosed. Each different support of the set can comprise a unique reporter.

For example the supports of a kit can comprise two or more of the reagent supports of the formula:

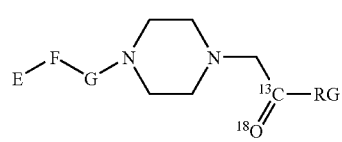

-continued

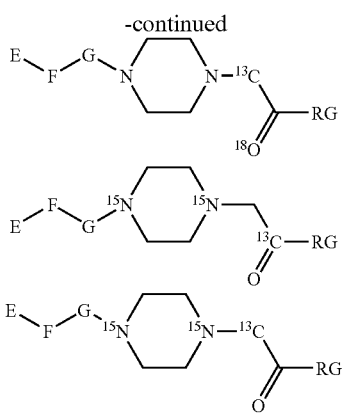

wherein: E, F, G and RG have been previously described and their characteristics disclosed.

In some embodiments, the kit comprises a proteolytic enzyme. The proteolytic enzyme can be trypsin, papain, pepsin, ArgC, LysC, V8 protease, AspN, pronase, chymotrypsin or carboxypeptid[e]ase C. In some embodiments, the kit can comprise instructions for using the labeling reagents to differentially label the analytes of different samples.

D. Compositions

In some embodiments, this invention pertains to compositions that can be used as labeling reagents. The compositions can be labeling reagents of the formula: RP—X—LK—Y—RG, wherein the atoms, moieties or bonds X, Y, RP, LK RG have been previously described and their characteristics disclosed. The labeling reagents can be isomeric or isobaric. Other properties of the labeling reagents have likewise been disclosed. For example, the labeling reagents can be useful for the multiplex analysis of one or more analytes in the same sample, or in two or more different samples.

The labeling reagents can be isotopically enriched (coded) with at least one heavy atom isotope. The labeling reagents can be isotopically enriched to comprise two or more heavy atom isotopes. The labeling reagents can be isotopically enriched to comprise three or more heavy atom isotopes. The labeling reagents can be isotopically enriched to comprise four or more heavy atom isotopes. In some embodiments, at least one heavy atom isotope is incorporated into a carbonyl or thiocarbonyl group of the labeling reagent and at least one other heavy atom isotope is incorporated into the reporter group of the labeling reagent.

Each incorporated heavy atom isotope can be present in at least 80 percent isotopic purity. Each incorporated heavy atom isotope can be present in at least 93 percent isotopic purity. Each incorporated heavy atom isotope can be present in at least 96 percent isotopic purity.

The labeling reagents comprise a reporter group that contains a fixed charge or that is ionizable. The reporter group therefore can include basic or acidic moieties that are easily ionized. In some embodiments, the reporter can be a morpholine, piperidine or piperazine compound. In some embodiments, the reporter can be a carboxylic acid, sulfonic acid or phosphoric acid group containing compound. Accordingly, is some embodiments, the labeling reagents can be isolated in their salt form. For example, piperazine containing labeling reagents can be obtained as a mono-TFA salt, a mono-HCl salt, a bis-TFA salt or a bis-HCl salt. The number of counterions present in the labeling reagent can depend in the number of acidic and/or basic groups present in the labeling reagent.

In some embodiments, the labeling reagents can comprise a carbonyl or thiocarbonyl linker. Labeling reagents comprising a carbonyl or thiocarbonyl linker can be used in active ester form for the labeling of analytes. In an active ester, an alcohol group forms a leaving group (LG). In some embodiments, the alcohol (LG) of the active ester can have the formula:

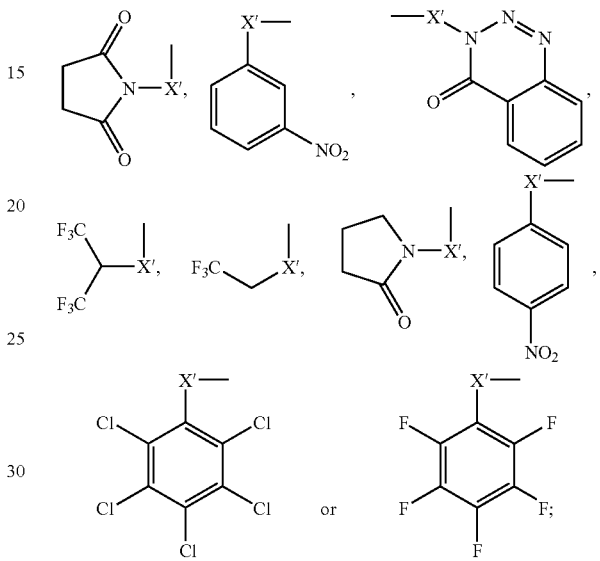

wherein X' is O or S. The active ester can be an N-hydroxysuccinimidyl ester.

In some embodiments, the active ester compound can be a 5, 6 or 7 membered heterocyclic ring comprising a ring nitrogen atom that is N-alkylated with a substituted or unsubstituted acetic acid moiety to which the alcohol moiety of the active ester is linked through the carbonyl carbon of the N-alkyl acetic acid moiety, wherein the compound is isotopically enriched with one or more heavy atom isotopes. The heterocyclic ring of the active ester can be substituted with one or more substituents. The one or more substituents can be alkyl, alkoxy or aryl groups. The one or more substituents can be alkylamine, alkylhydroxy or alkylthio groups. The one or more substituents can be protected or unprotected amine groups, hydroxyl groups or thiol groups. The heterocyclic ring can be aliphatic. The heterocyclic ring can be aromatic. The heterocyclic ring can comprise one or more additional nitrogen, oxygen or sulfur atoms.

In some embodiments, the active ester compound can be an N-substituted morpholine acetic acid active ester compound of the formula:

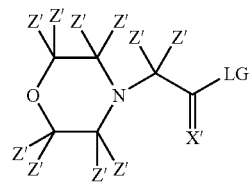

or a salt thereof, wherein; LG is the leaving group of an active ester; X' is O or S; each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms. In some embodiments, Z' independently can be hydrogen, deuterium, fluorine, chlorine, bromine or iodine. In some embodiments, Z' independently can be hydrogen, methyl or methoxy. In some embodiments, X' is $^{16}O$ or $^{18}O$. The nitrogen atom of the morpholine ring can be $^{14}N$ or $^{15}N$. In some embodiments, the active ester is a compound comprising the formula:

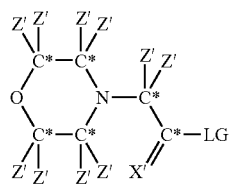

wherein each C* is independently $^{12}C$ or $^{13}C$; LG is the leaving group of an active ester; X' is O or S; and each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms.

In some embodiments, the active ester compound can be an N-substituted piperidine acetic acid active ester compound of the formula:

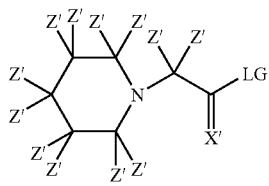

or a salt thereof, wherein; LG is the leaving group of an active ester; X' is O or S; each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms. In some embodiments, Z' independently can be hydrogen, deuterium, fluorine, chlorine, bromine or iodine. In some embodiments, Z' independently can be hydrogen, methyl or methoxy. In some embodimefits X' is $^{16}O$ or $^{18}O$. The nitrogen atom of the piperidine ring can be $^{14}N$ or $^{15}N$. In some embodiments, the active ester is a compound comprising the formula:

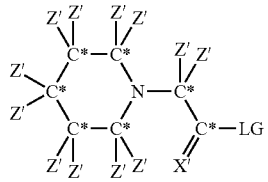

wherein each C* is independently $^{12}C$ or $^{13}C$; LG is the leaving group of an active ester; X' is O or S; and each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms.

In some embodiments, the active ester compound can be an N-substituted piperidine acetic acid active ester compound of the formula:

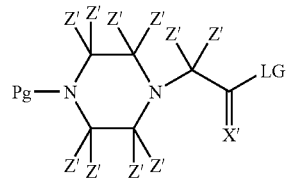

or a salt thereof, wherein; LG is the leaving group of an active ester; X' is O or S; Pg is an amine protecting group; and each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms. In some embodiments, Z' independently can be hydrogen, deuterium, fluorine, chlorine, bromine or iodine. In some embodiments, Z' independently can be hydrogen, methyl or methoxy. In some embodiments X' is $^{16}O$ or $^{18}O$. In some embodiments, each nitrogen atom of the piperazine ring is $^{14}N$ or $^{15}N$. In some embodiments, the active ester is a compound comprising the formula:

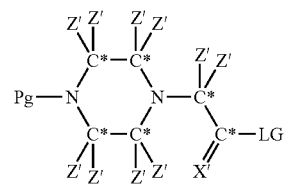

wherein each C* is independently $^{12}C$ or $^{13}C$; LG is the leaving group of an active ester; X' is O or S; Pg is an amine protecting group and each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms.

Having described embodiments of the invention, it will now become apparent to one of skill in the art that other embodiments incorporating the concepts may be used. It is felt, therefore, that these embodiments should not be limited to disclosed embodiments but rather should be limited only by the spirit and scope of the invention.

EXAMPLES

This invention is now illustrated by the following examples that are not intended to be limiting in any way.

Example 1

Synthesis of Morpholine Acetic Acid

Bromoacetic acid (2 g, 14.4 mole) was dissolved in tetrahydrofuran (50 mL) and added dropwise to a stirred solution of morpholine (3.76 g, 43.2 mole) in tetrahydrofuran (THF, 20 mL). The solution was stirred at room temperature for three days. The white solid (4.17 g) was filtered, washed with THF (100 mL), and recrystallised from hot ethanol (EtOH), Yield: 2.59 g: IR:1740 cm-1. For the two different isobaric versions of morpholine acetic acid, either bromoacetic-1-$^{13}$C acid (Aldrich PN 27,933-1) or bromoacetic-2-$^{13}$C acid (Aldrich PN 27,935-8) was substituted for bromoacetic acid.

Example 2

Synthesis of Morpholine Acetic Acid N-Hydroxysucciniimide Ester

Dimethylformamide (dry, 1.75 g, 0.024M) was dissolved in tetrahydrofuran (dry, 30 mLs). This solution was added dropwise to a stirred solution of thionyl chloride (2.85 g, 0.024M) dissolved in tetrahydrofuran(dry, 20 mLs) and cooled in an ice bath. After complete addition and 30 minutes on ice, the ice bath was removed and solid N-hydroxysuccinimide (2 g, 0.017 M) was added (which completely dissolved) immediately followed by solid pre-powdered morpholine acetic acid [or -1-$^{13}$C or -2-$^{13}$C morpholine acetic acid] (3.64 g, 0.016M). The morpholine acetic acid dissolved slowly giving a homogeneous solution that rapidly became cloudy. The reaction was left vigorously stirring over night at room temperature. The white solid was washed with tetrahydrofuran and dried under vacuum, weight 3.65 g (67%), IR spectrum 1828.0 cm-1, 1790.0 cm-1, 1736.0 cm-1.

Example 3

Figure 1B:
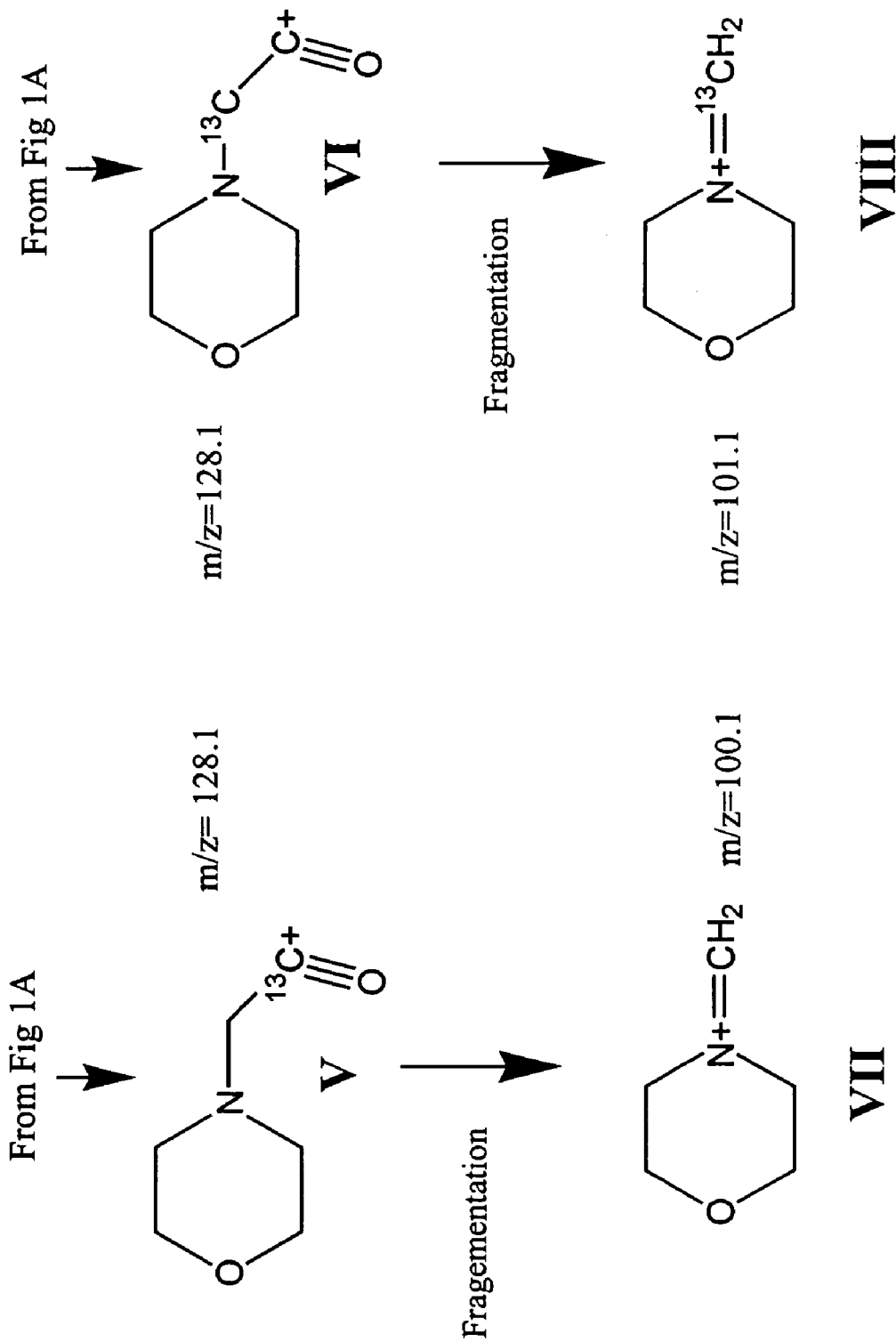
FIG. 1B illustrates the fragmentation of the labeled analyte illustrated in FIG. 1A to thereby produce reporter moieties (e.g. compounds VII and VIII as signature ions) of different masses from the isobarically labeled analytes.

Analyte Determination and Relative Quantitation in Two Samples 100 pmole amounts of freeze-dried Glu-Fibrinopeptide B (Sigma) were reacted with 200 µl of freshly-made 2% w/v solutions of either I or II (See: FIG. 1A for structure and Examples 1 & 2 for preparation) in ice-cold 0.5M MOPS buffer (pH 7.8 with NaOH) for 30 minutes on ice. The reaction was terminated by the addition of TFA to 0.5% v/v final concentration. The modified peptides were then mixed in various pre-determined proportions to approximately cover the range 1:10 to 10:1 of the differentially labeled peptides. Each peptide mixture was individually purified by reverse-phase de-salting using a Millipore C18 Zip-Tip. Excess reagent and buffer do not retain on the reverse-phase packings, and were thus efficiently removed prior to MS analysis. The mixtures (0.5 µl) were then spotted onto a MALDI target plate, over-spotted with 0.5 µl of 1% w/v α-cyano cinnamic acid in 50% aqueous acetonitrile and each sample was analyzed using a MALDI source fitted to a QTOF analyzer.

Figure 2:
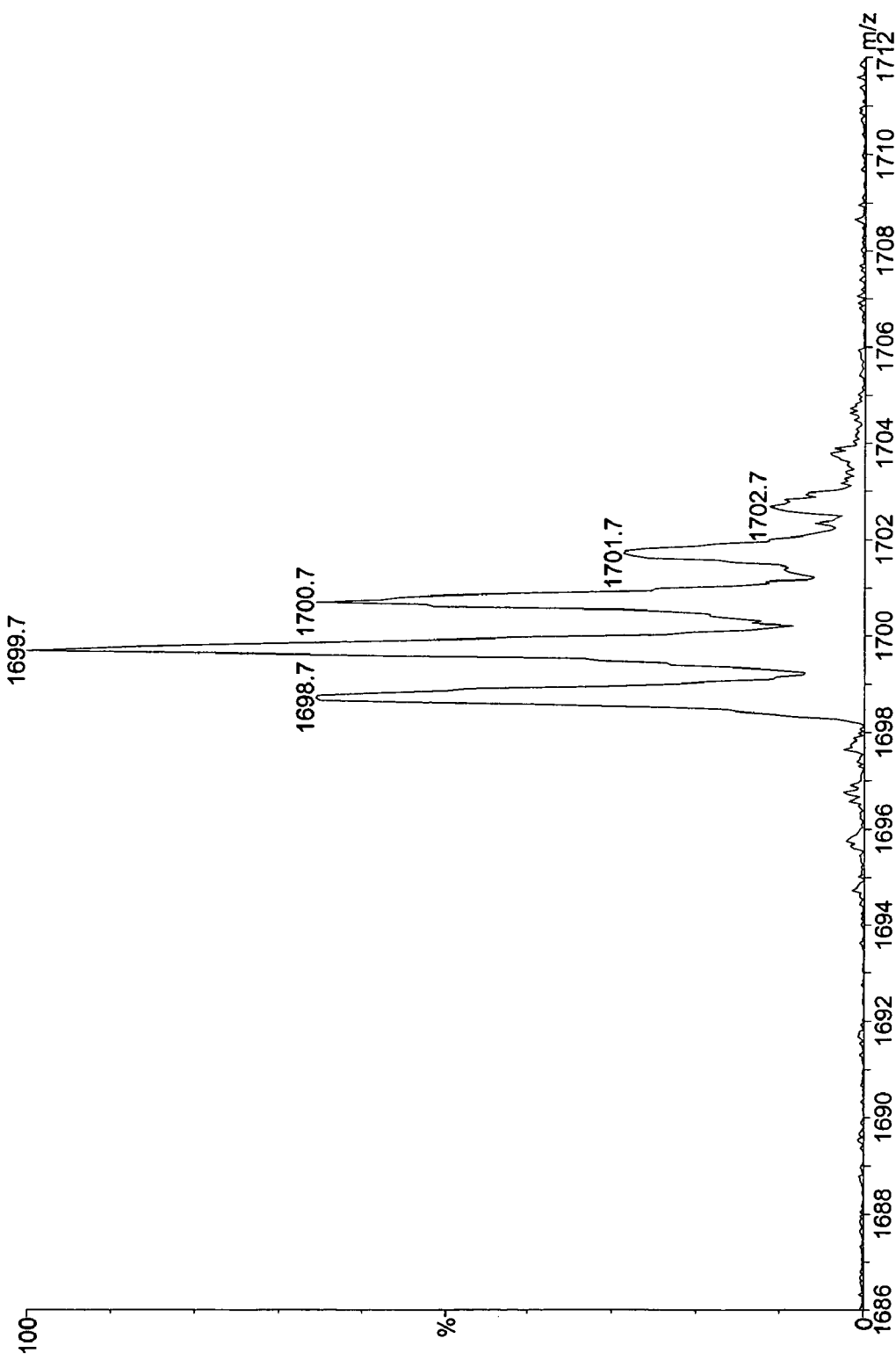
FIG. 2 is an expansion plot of a mass spectrum of a labeled analyte.

FIG. 2 is an expansion plot of the MS spectrum obtained from the 1:1 mix of Glu-fibrinopeptide as modified with reagents I and II. The peak at m/z 1699 represents the N-terminally modified mass of Glu-fibrinopeptide, and as expected, there is no observable difference in m/z of the two different forms of the peptide (See: FIGS. 1A(III) and 1A(IV). The modified peptides are isobaric. The isotopic cluster observed for the peak is exactly as expected for a single species.

Figure 3:
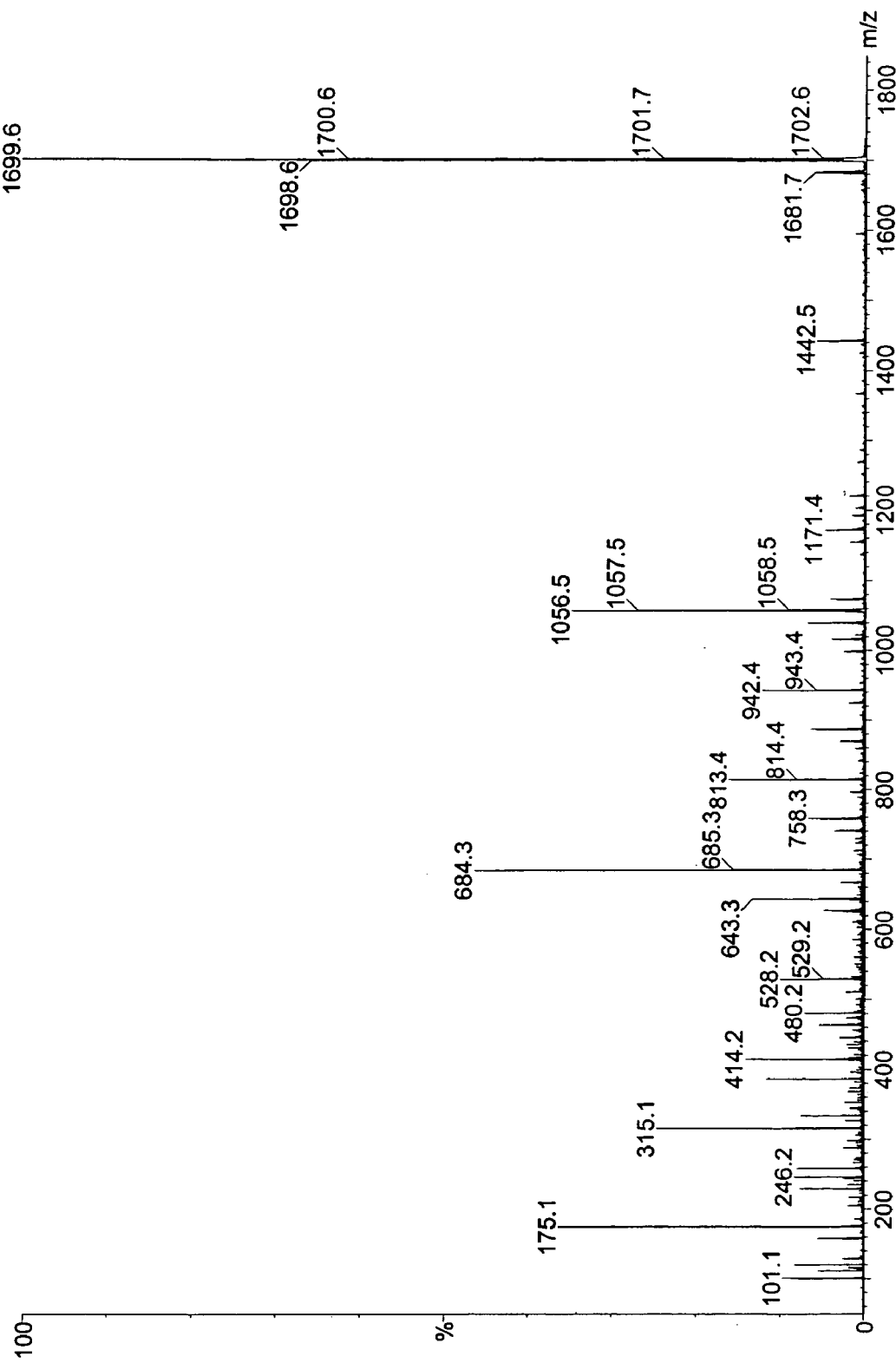
FIG. 3 is the complete mass spectrum obtained from a second mass analysis of the selected labeled analyte identified in the expansion plot of FIG. 2.
Figure 4:
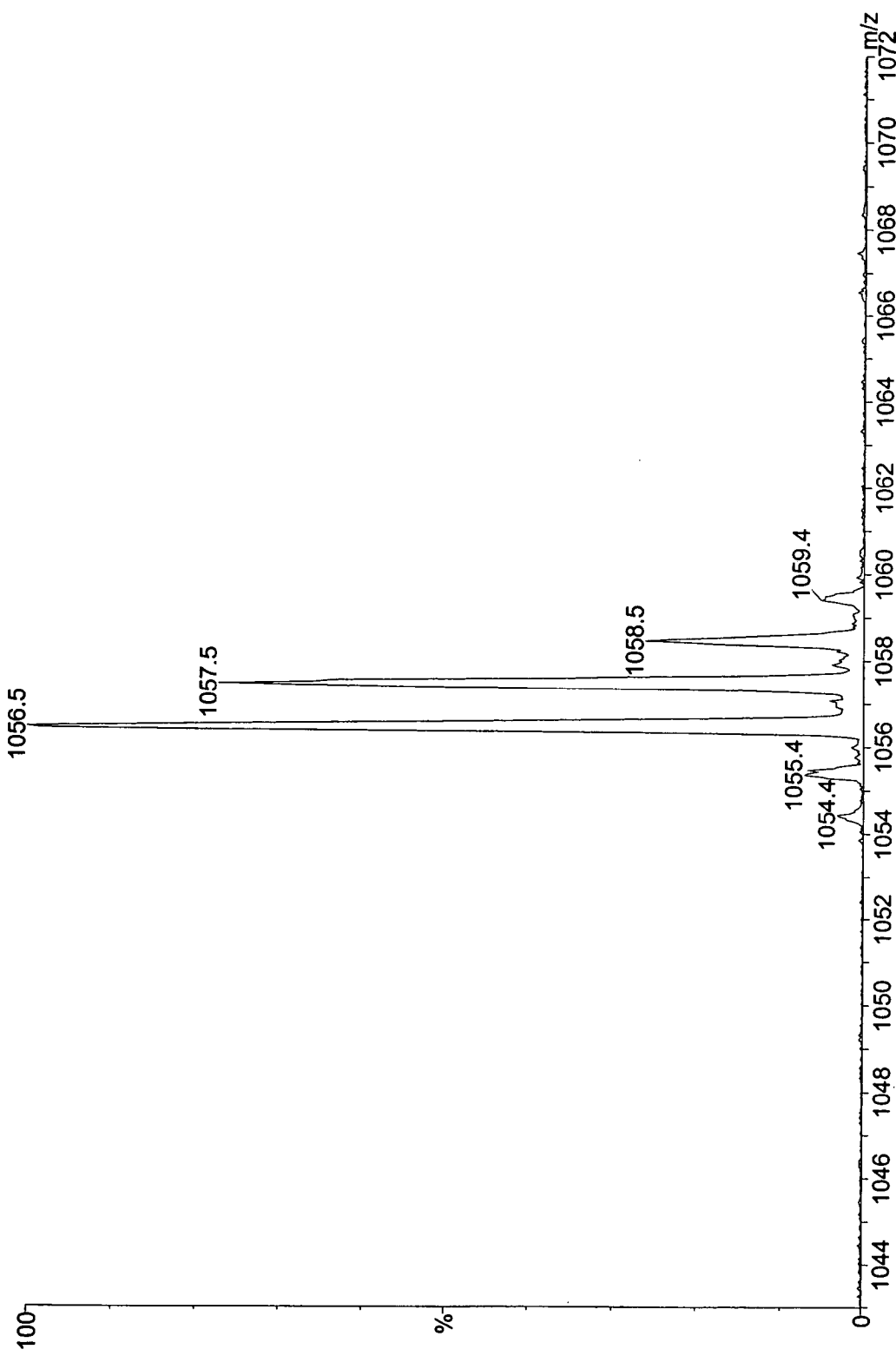
FIG. 4 is an expansion plot of a mass spectrum of the predominate y-ion daughter fragment ion of the analyte as determined in the second mass analysis.
Figure 5:
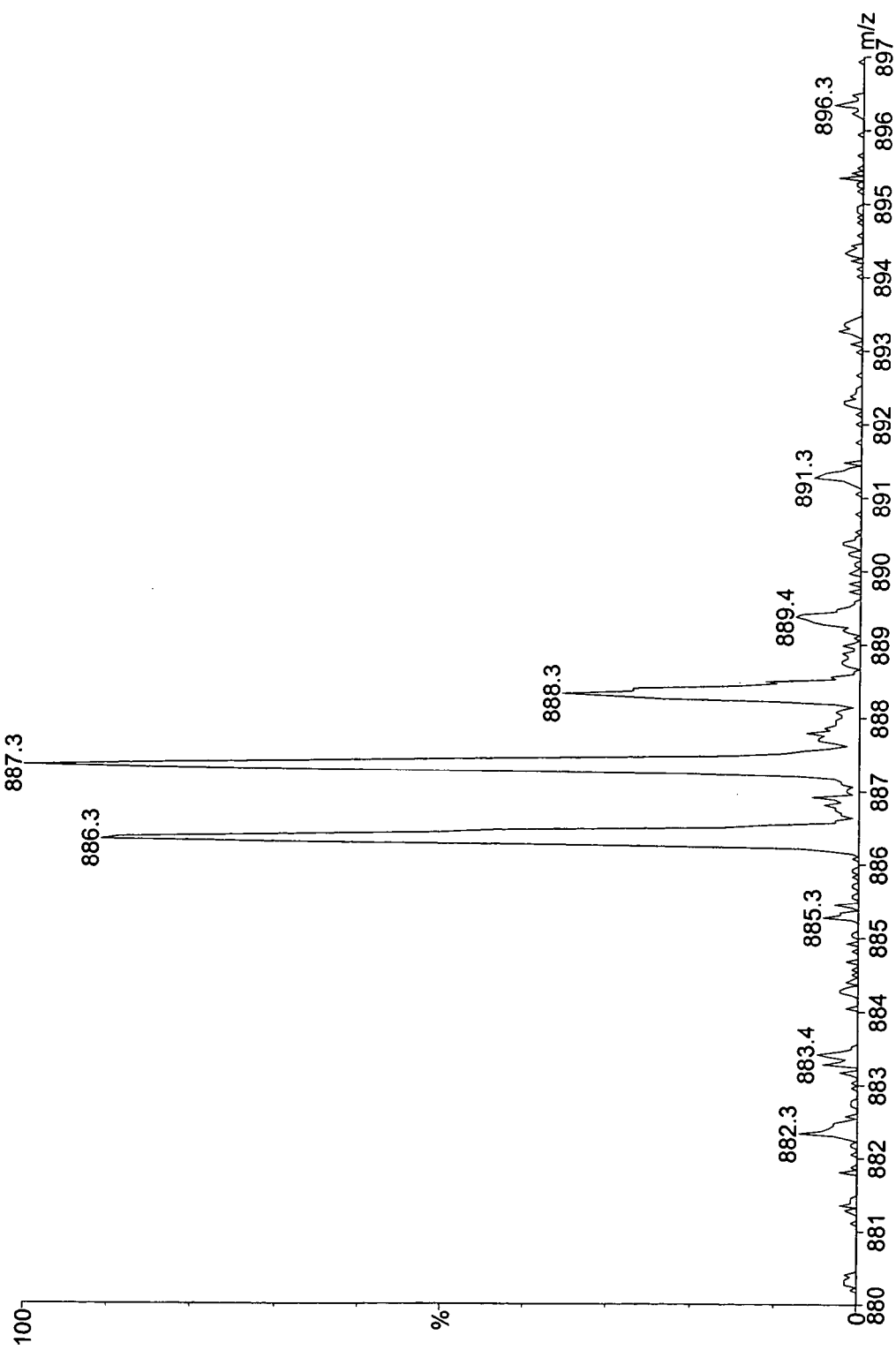
FIG. 5 is an expansion plot of a mass spectrum of the predominate b-ion daughter fragment ion of the analyte as determined in the second mass analysis.

The singly-charged precursor ion of m/z 1699 was then selected for fragmentation by low energy CID (collision offset of approximately −70V), yielding the MS/MS spectrum found in FIG. 3. As expected, the observed ion series was predominantly of types b- and y-. All these ions appeared as single species, with no indication that they comprised a 1:1 mixture of the differentially-labeled peptide species. For example, an expansion of the prominent y-ion at m/z 1056.5 is shown in the expansion plot as FIG. 4 and the prominent b-ion at m/z 886.3 is shown in the expansion plot as FIG. 5.

TABLE 1

| Observed | Predicted |
| --- | --- |
| 0.13 | 0.125 |
| 0.17 | 0.166 |
| 0.2 | 0.25 |
| 0.46 | 0.5 |
| 1.03 | 1 |
| 2.15 | 2 |
| 4.16 | 4 |
| 6.3 | 6 |
| 7.9 | 8 |

Figure 7:
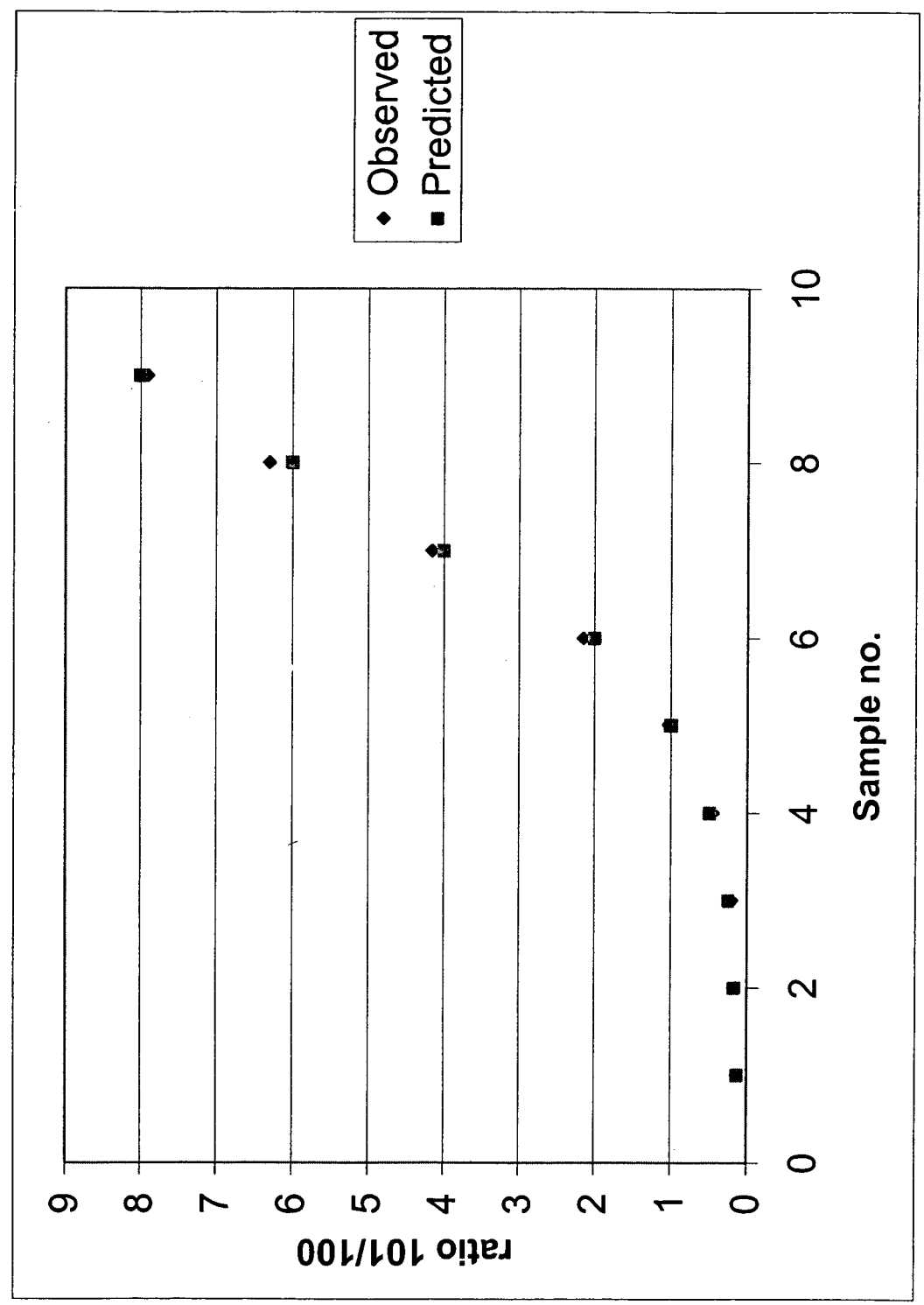
FIG. 7 is a plot of observed vs. predicted ratios of reporters determined by a second mass analysis for various mixtures of a labeled peptide, each peptide of the mixture comprising one of two different reporters.

Close examination of the spectrum at about 100 m/z (FIG. 6), however, reveals the presence of both species VII and VIII (FIG. 1B), which are the fragmentation products of species V and VI (FIG. 1B), respectively. No peaks are observed at m/z 128.1, thereby indicating that species V and VI are not stable enough to be observed. In this example, therefore, it may be that fragmentation of the amide bond between the carbonyl group and the amino-terminal amino acid of the peptide (e.g. bond Y) induced subsequent fragmentation of the reporter/linker moiety (bond X) and loss of the carbonyl moiety as neutral CO. Peak integration was performed using the instrumentation provided with the instrument. Following compensation for the naturally occurring second C-13 isotopic contribution of approximately 6 percent, the measured relative ratio of VIII/VII (101/100) was 1.03 (expected value 1.00). Table 1 shows actual versus observed ratios for additional experimental mixtures prepared (ratio expressed as intensity m/z 101/m/z 100), with correction for the naturally occurring second C-13 contribution. This data is also represented graphically in FIG. 7. There is excellent agreement between observed and predicted values, with mean error<10%.

Example 4

Proteomic Analysis

In practice, a representative proteomic analysis can be performed as follows. Total cellular protein extracts for comparison (e.g. samples A and B) are separately digested with trypsin, or another proteolytic enzyme. The resulting peptide mixtures are separately reacted with different isomeric of isobaric labeling reagents (for example, compounds I and II) to give complete modification of N-terminal and lysine amines of the peptides. For example, sample A can be reacted with compound I and sample B can be reacted with compound II. Each of the samples containing modified peptides/proteins are then be mixed together before chromatographic separation (often using multi-dimensional HPLC) and analyzed by MS and MS/MS techniques. The labeling can be performed with a single label treatment (no prior blocking of lysine groups with a second reagent required) as the groups are isobaric.

The mixture of labeled proteins/peptides is then chromatographically separated and the eluent, or fractions thereof, analyzed by mass spectrometry as described in Example 3, above. Effective sensitivity may also be significantly increased using triple-quadruople or Q-trap mass spectrometers, where the m/z region of 100 and 101 is monitored in precursor-ion mode. The relative ratios of the two "signature" peaks are directly correlated with the ratio of each peptide/protein analyte of interest in each of samples A and B. As used herein, the "signature" peaks are the peaks for the reporter.

Example 5

Analyte Determination and Quantitation Relative to An Internal Standard

Total cellular protein extracts for comparison (e.g. samples A and B) are separately digested with trypsin. The resulting peptide mixtures are separately reacted with X and XI (FIG. 8) to give substantially complete modification of N-terminal and lysine amines as described above. For example, sample A peptides are reacted with X and sample B peptides are reacted with XI. Known amounts or each of samples A and B, containing substantially modified peptides, are then mixed together. To the combined mixture of A and B is now added, in accurately determined amount, a set (one or more) of synthetic peptide(s) that correspond exactly in amino acid sequence and/or post-translational modification (e.g. phosphorylation) to peptide(s) that may be present in the mixture of samples A and B, and where the synthetic peptide(s) are labeled with another member of set of isobaric labeling reagents (e.g. compounds XII or XIII, see: FIG. 8). The combined mixture of peptides from sample A, sample B and synthetic internal standard peptides can optionally be subjected to chromatographic separation, for example by multi-dimensional HPLC, or electrophoretic separation and then analyzed by MS and MS/MS techniques as described previously. All equivalent labeled peptides from sample A, B and synthetic counterparts of identical sequence are isobaric and have substantially identical chromatographic properties. By "substantially identical chromatographic properties" we mean that there is very little, if any, separation of the differentially labeled but otherwise identical peptides. Following MS/MS analysis, the absolute concentration of peptides from sample A and B may be accurately determined by comparison of the relative intensity of the reporters for X (sample A) and for XI (sample B) with respect to the intensity of the reporter (the "signature peak") resulting from the standard peptide labeled with the additional member of the isobaric set (e.g. XII or XIII).

Although the foregoing is a description of two samples (i.e. Samples A and B), this process could be extended in many practical ways. For example, there may be many samples that are analyzed simultaneously provided there is a large enough set of labeling reagents.

There could be a double (or more where there are more samples to be analyzed) internal standard (e.g. sample A peptides may be 'spiked' with synthetic peptides labeled with reagent XII and sample B peptides may be spiked with synthetic peptides labeled with reagent XIII (of known absolute concentration)). When all are combined, separated and analyzed as described above, Sample A peptides can be quantitated relative to the signature peak for compound XII and sample B peptides can be quantitated relative to the signature peak for compound XIII.

Example 6

Exemplary Synthesis of Piperidine Acetic Acid N-hydroxysuccinimide Ester

Bromoacetic acid is dissolved in tetrahydrofuran (or another suitable non-nucleophilic solvent) and added dropwise to a stirred solution containing an excess of piperidine in tetrahydrofuran (THF, or another suitable non-nucleophilic solvent). The solution is stirred at room temperature for one to three days. The solid is filtered, washed with THF (or another suitable non-nucleophilic solvent), and optionally recrystallised. For the two different isobaric versions of piperidine acetic acid, either bromoacetic-1-$^{13}$C acid (Aldrich PN 27,933-1) or bromoacetic-2-$^{13}$C acid (Aldrich PN 27,935-8) can be substituted for bromoacetic acid. Isomer substituted piperidine can be prepared from suitable starting material or it can be obtained, on a custom order basis, from sources such as Cambridge Isotope Laboratories or Isotec.

To convert the acetic acid derivatives to active esters, such as an N-hydroxysuccinimidyl ester, dimethylformamide (DMF) is dissolved in tetrahydrofuran (or another suitable non-nucleophilic solvent). This solution is added dropwise to a stirred solution of an equal molar amount of thionyl chloride (based upon the molar quantity of DMF) dissolved in tetrahydrofuran (or another suitable non-nucleophilic solvent) and cooled in an ice bath. After complete addition and 30 minutes on ice, the ice bath is removed and solid N-hydroxysuccinimide is added immediately followed by piperidine acetic acid (or -1-$^{13}$C or -2-$^{13}$C piperidine acetic acid). The reaction is left vigorously stirring over night at room temperature. The product piperidine acetic acid N-hydroxysuccinimide ester is then isolated from the reaction mixture possibly by mere filtration. Recrystallization and/or chromatography can optionally be used to purify the crude product.

Example 7

Exemplary Synthesis of Piperazine Acetic Acid N-hydroxysuccinimide Ester

A solution containing two equivalents of piperazine dissolved in tetrahydrofuran (THF) is added dropwise to a solution containing one equivalent of bromoacetic acid (as compared with the amount of piperazine) dissolved in tetrahydrofuran. The two solutions should be as concentrated as is practical. The resulting reaction solution is stirred at room temperature for one to three days. The solid is filtered, washed with THF, and optionally recrystallised. For the two different isobaric versions of piperidine acetic acid, either bromoacetic-1-$^{13}$C acid (Aldrich PN 27,933-1) or bromoacetic-2-$^{13}$C acid (Aldrich PN 27,935-8) can be substituted for bromoacetic acid.

To convert the acetic acid derivatives to active esters, such as an N-hydroxysuccinimidyl ester, dry dimethylformamide (DMF, 1.75 g, 0.024M) can be dissolved in tetrahydrofuran. This solution can be added dropwise to a stirred solution of an equal molar amount of thionyl chloride (based upon the molar quantity of DMF) dissolved in tetrahydrofuran and cooled in an ice bath. After complete addition and 30 minutes on ice, the ice bath can be removed and solid N-hydroxysuccinimide added immediately followed by piperazine acetic acid (or -1-$^{13}$C or -2-$^{13}$C piperidine acetic acid). The reaction can be left vigorously stirring over night at room temperature. The product piperazine acetic acid N-hydroxysuccinimide ester can then be isolated from the reaction mixture possibly by mere filtration. Recrystallization or chromatography can then be used to purify the crude product.

Example 8

Exemplary Synthesis of N,N'-(2-methoxyethyl)-glycine Active Ester (Copied from U.S. Pat. No. 6,326,479

To 1.1 mole of bis(2-methoxyethyl)amine (Aldrich Chemical) was added dropwise 500 mmol of tert-butyl chloroacetate (Aldrich Chemical). The reaction was allowed to stir for three days and was then worked up. To the final reaction contents was added 250 mL of dichloromethane (DCM) and 200 mL of water. To this stirring solution was added portionwise, 300 mmol of solid potassium carbonate (K$_2$CO$_3$). After complete mixing, the layers were separated. The DCM layer was washed once with a volume of water, dried (Na$_2$SO$_4$), filtered and evaporated to yield 66.3 g of a very thin yellow oil. This crude product was Kugelrohr distilled at 60° C. (200–500 µM Hg) to yield 58.9 g of a clear colorless oil (238 mmol; 95%).

To the purified (stirring) N,N'-(2-methoxyethyl)-glycine-tert-butyl ester was slowly added 12.1 mL of concentrated hydrochloric acid. The reaction was allowed to stir overnight and then the byproducts (e.g. water, HCl, isobutylene) were removed by vacuum evaporation. $^1$H-MNR analysis indicated the t-butyl ester was hydrolyzed but it appeared that there was water and HCl still present. The crude product was co-evaporated 2× from acetonitrile (ACN) but water and HCl were still present. To eliminate impurities, a 4.4 g aliquot was removed from the crude product and Kugelrohr distilled at 135–155° C. (100–200 µM Hg with rapidly dropping pressure after distillation began). Yield 4.2 g (18.4 mmol; 95% recovery of thick, clear, colorless oil). The distilled product did not contain any water or HCl.

The active ester (e.g. N-hydroxysuccinimidyl ester) of any suitable isotopically labelled substituted or unsubstituted N,N'-(2-methoxyethyl)-glycine can then be prepared by methods known in the art, such as those described herein.

Example 9

Exemplary Method for Preparing a Solid Support Comprising Labelling/Tagging Reagents A commercially available peptide synthesis resin comprising a "sterically hindered cleavable linker" is reacted with at least two-fold excess of an aminoalkyl piperazine (e.g. 1-(2-aminoethyl)piperazine, Aldrich P/N A5,520-9;

isomeric versions can be made by the process illustrated in FIG. 11 in combination with the description in the specification). By "sterically hindered cleavable linker" we mean that the linker comprises a secondary or tertiary atom that forms the covalent cleavable bond between the solid support and the atom or group reacted with the cleavable linker. Non-limiting examples of sterically hindered solid supports include: Trityl chloride resin (trityl-Cl, Novabiochem, P/N 01-64-0074), 2-Chlorotrityl chloride resin (Novabiochem, P/N 01-64-0021), DHPP (Bachem, P/N Q-1755), MBHA (Applied Biosystems P/N 400377), 4-methyltrityl chloride resin (Novabiochem, P/N 01-64-0075), 4-methoxytrityl chloride resin (Novabiochem, P/N 01-64-0076), Hydroxy-(2-chorophnyl)methyl-PS (Novabiochem, P/N 01-64-0345), Rink Acid Resin (Novabiochem P/Ns 01-64-0380, 01-64-0202), NovaSyn TGT alcohol resin (Novabiochem, P/N 01-64-0074). Excess reagents are then removed by washing the support. The secondary amine of the support bound piperazine is then reacted with an excess of bromoacetic acid in the presence of a tertiary amine such as triethylamine. Excess reagents are then removed by washing the support. Depending on the method to be used to make an active ester of the carboxylic acid (e.g. whether or not a salt of the carboxylic acid is required for the active ester synthesis), the wash can be selected to have a pH that is adjusted to protonate the support bound carboxylic acid group of the bis-alkylated piperazine. The carboxylic acid group of the support bound piperazine is then converted to an active ester (e.g. N-hydroxysuccinimidyl ester) using procedures known in the art for the production of acid esters of a carboxylic acid, such as those described above. The resulting solid support can thereafter be used to label analytes of a sample (e.g. peptides) having nucleophilic functional groups. The labeled analytes can then be released from the support as described by the manufacturer's product instructions. The product of each cleavage reaction can then be combined to form a sample mixture.

We claim:

1. A compound of formula:

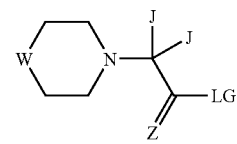

or a salt thereof, wherein,
each carbon of the heterocyclic ring has the formula C(J)$_2$;
W is NH, N—R$^1$, N—R$^2$, P—R$^1$, P—R$^2$, O, C or S;
each J is the same or different and is H, deuterium (D), R$^1$, OR$^1$, SR$^1$, NHR$^1$, N(R$^1$)$_2$, fluorine, chlorine, bromine or iodine;
Z is O, S, NH or NR$^1$; and
LG is an alcohol or thiol leaving group selected from the group consisting of:

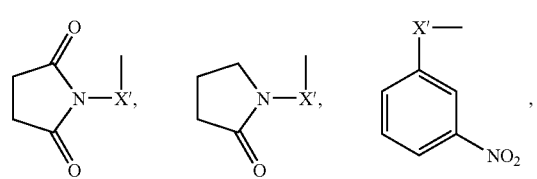

-continued

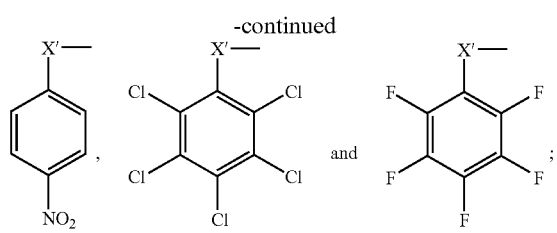

wherein,

X' is O or S;

R¹ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms; and R² is an amino alkyl, hydroxy alkyl, thio alkyl group or a cleavable linker that cleavably links the reagent to a solid support wherein the amino alkyl, hydroxy alkyl or thio alkyl group comprises one to eight carbon atoms, which may optionally contain a heteroatom or a substituted or unsubstituted aryl group, and wherein the carbon atoms of the alkyl and aryl groups independently comprise linked hydrogen, deuterium and/or fluorine atoms; and wherein the compound is isotopically enriched with one or more heavy atom isotopes.

2. The compound of claim 1, wherein the compound is isotopically enriched with three or more heavy atom isotopes.

3. The compound of claim 1, wherein the six-membered heterocydlic ring is substituted with one or more substituents.

4. The compound of claim 3, wherein the one or more substituents are alkyl, alkoxy or aryl groups.

5. The compound of claim 1, wherein LG is N-hydroxysuccinimide.

6. The compound of claim 1, wherein the compound is a salt.

7. The compound of claim 1, wherein the compound is a mono-TFA salt, a mono-HCl salt, a bis-TFA salt or a bis-HCl salt.

8. The compound of claim 1, wherein each incorporated heavy atom isotope is present in at least 80 percent isotopic purity.

9. The compound of claim 1, wherein each incorporated heavy atom isotope is present in at least 93 percent isotopic purity.

10. The compound of claim 1, wherein each incorporated heavy atom isotope is present in at least 96 percent isotopic purity.

11. A method comprising:
a) reacting an analyte with the compound of claim 1 to thereby produce a labeled analyte; and
b) mixing the labeled analyte with one or more differentially labeled analytes.

12. The compound of claim 1 of the formula:

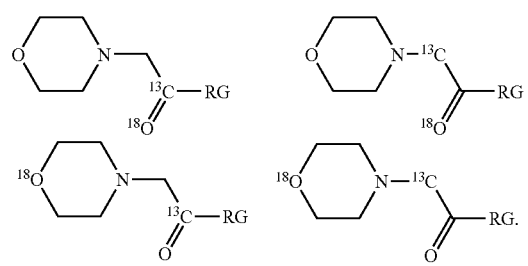

13. The compound of claim 1 of the formula:

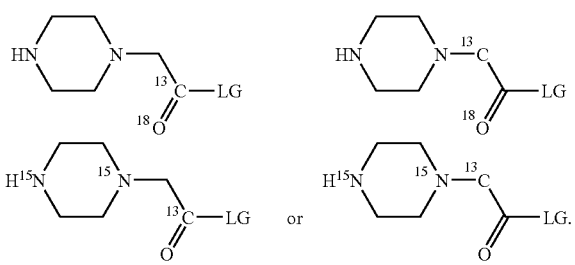

14. An N-substituted morpholine acetic acid active ester compound of the formula:

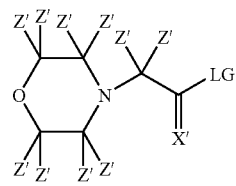

or a salt thereof, wherein;

LG is the Leaving group of an active ester selected from the group consisting of:

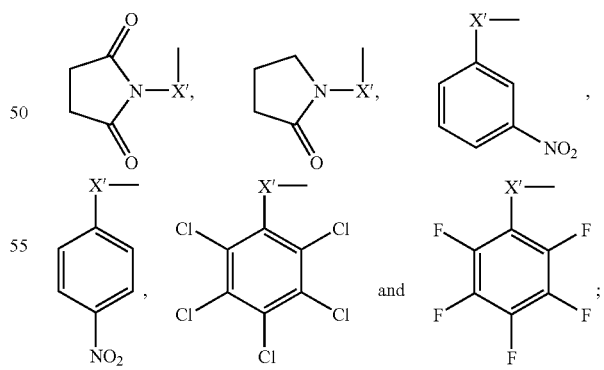

X' is O or S;

each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms; and
wherein the N-substituted morpholine acetic add active ester is isotopically enriched with one or more heavy atom isotopes.

15. The compound of claim 14, wherein the N-substituted morpholine acetic acid active ester is isotopically enriched with three or more heavy atom isotopes.

16. The compound of claim 14, wherein LG is N-hydroxysuccinimide.

17. The compound of claim 14, wherein each Z' is independently hydrogen, deuterium, fluorine, chlorine, bromine or iodine.

18. The compound of claim 14, wherein each Z' is independently hydrogen or methyl.

19. The compound of claim 14, wherein X' is $^{16}$O or $^{18}$O.

20. The compound of claim 14, wherein the nitrogen atom of the morpholine ring is $^{14}$N or $^{15}$N.

21. The compound of claim 14, of the formula:

[structure]

wherein;
each C* is independently $^{12}$C or $^{13}$C;
LG is the leaving group of an active ester as defined in claim 14;
X' is O or S; and
each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms.

22. The compound of claim 14, wherein the compound is a mono-TFA salt or a mono-HCl salt.

23. The compound of claim 14, wherein each incorporated heavy atom isotope is present in at least 80 percent isotopic purity.

24. The compound of claim 14, wherein each incorporated heavy atom isotope is present in at least 93 percent or isotopic purity.

25. The compound of claim 14, wherein each incorporated heavy atom isotope is present in at least 96 percent or isotopic purity.

26. An N-substituted piperidine acetic add active ester compound of the formula:

[structure]

or a salt thereof, wherein;

LG is the leaving group of an active ester selected from the group consisting of:

[structures]

X' is O or S;
each Z' is independently hydrogen, deuterium, fluorine, chlorine, bromine, iodine, an amino add side chain or a straight chain or branched C1–C6 allyl group that may optionally contain a substituted or unsubstituted aryl group wherein the carbon atoms of the alkyl and aryl groups each independently comprise linked hydrogen, deuterium or fluorine atoms; and
wherein the N-substituted piperidine acetic acid active ester is isotopically enriched with one or more heavy atom isotopes.

27. The compound of claim 26, wherein the N-substituted piperidine acetic acid active ester is isotopically enriched with three or more heavy atom isotopes.

28. The compound of claim 26, wherein LG is N-hydroxysuccinimide.

29. The compound of claim 26, wherein each Z' is independently hydrogen, deuterium, fluorine, chlorine, bromine or iodine.

30. The compound of claim 26, wherein each Z' is independently hydrogen or methyl.

31. The compound of claim 26, wherein X' is $^{16}$O or $^{16}$O.

32. The compound of claim 26, wherein the nitrogen atom of the piperidine ring is $^{14}$N or $^{15}$N.

33. The compound of claim 26, of the formula:

[structure]

wherein;
each C* is independently $^{12}$C or $^{13}$C;
LG is the leaving group of an active ester as defined in claim 26;
X' is O or S; and
each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms.

34. The compound of claim 26, wherein the compound is a mono-TFA salt or a mono-HCl salt.

35. The compound of claim 26, wherein each incorporated heavy atom isotope is present in at least 80 percent isotopic purity.

36. The compound of claim 26, wherein each incorporated heavy atom isotope is present in at least 93 percent or isotopic purity.

37. The compound of claim 26, wherein each incorporated heavy atom isotope is present in at least 96 percent or isotopic purity.

38. An N-substituted piperazine acetic acid active ester compound of the formula:

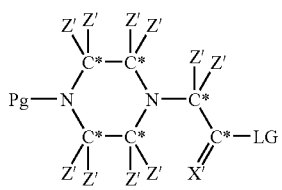

or a salt thereof, wherein;
LG is the leaving group of an active ester selected from the group consisting of:

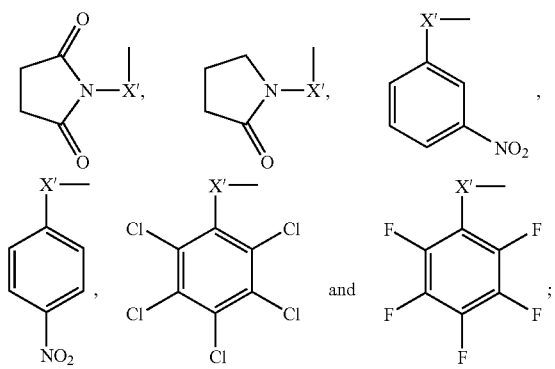

X' is O or S;
Pg is an amine-protecting group;
each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms; and
wherein the N-substituted piperazine acetic acid active ester is isotopically enriched with one or more heavy atom isotopes.

39. The compound of claim 38, wherein the N-substituted piperazine acetic acid active ester is isotopically enriched with three or more heavy atom isotopes.

40. The compound of claim 38, wherein LG is N-hydroxysuccinimide.

41. The compound of claim 38, wherein each Z' is independently hydrogen, deuterium, fluorine, chlorine, bromine or iodine.

42. The compound of claim 38, wherein each Z' is independently hydrogen or methyl.

43. The compound of claim 38, wherein X' is $^{16}O$ or $^{18}O$.

44. The compound of claim 38, wherein each nitrogen atom of the piperazine ring is $^{14}N$ or $^{15}N$.

45. The compound of claim 38, of the formula:

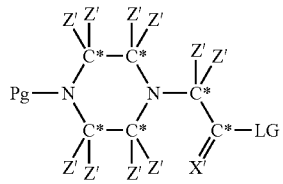

wherein,
each C* is independently $^{12}C$ or $^{13}C$;
LG is the leaving group of an active ester as defined in claim 38;
X' is O or S;
Pg is an amine protecting group; and
each Z' is independently hydrogen, deuterium, fluorine, chlorine, bromine, iodine, an amino acid side chain or a straight chain or branched C1–C6 alkyl group that may optionally contain a substituted or unsubstituted aryl group wherein the carbon atoms of the alkyl and aryl groups each independently comprise linked hydrogen, deuterium or fluorine atoms.

46. The compound of claim 38, wherein the compound is a mono-TFA salt, a mono-HCl salt, a bis-TFA salt or a bis-HCl salt.

47. The compound of claim 38, wherein each incorporated heavy atom isotope is present in at least 80 percent isotopic purity.

48. The compound of claim 38, wherein each incorporated heavy atom isotope is present in at least 93 percent or isotopic purity.

49. The compound of claim 38, wherein each incorporated heavy atom isotope is present in at least 96 percent or isotopic purity.

* * * * *

UNITED STATES PATENT AND TRADEMARK OFFICE
CERTIFICATE OF CORRECTION

PATENT NO. : 7,195,751 B2
APPLICATION NO. : 10/765267
DATED : March 27, 2007
INVENTOR(S) : Darryl J. C. Pappin and Michael Bartlet-Jones It is certified that error appears in the above-identified patent and that said Letters Patent is hereby corrected as shown below:

Column 48, lines 2-14, claim 12, the four formulae should appear as follows:

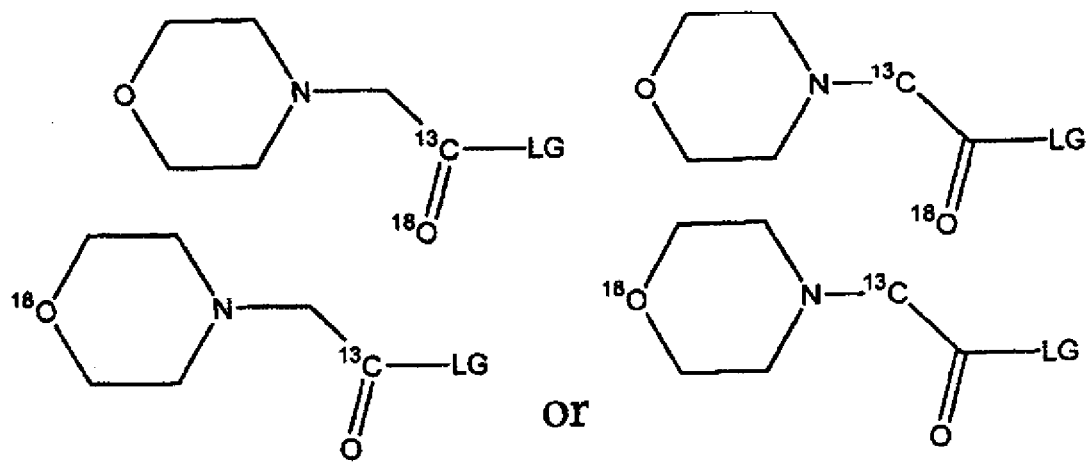

Column 52, line 2, claim 39, the word "add" should read --acid--.

Signed and Sealed this
Fifth Day of June, 2012

David J. Kappos
*Director of the United States Patent and Trademark Office*